United States Patent [19]
Dominiak et al.

[11] Patent Number: 5,478,211
[45] Date of Patent: Dec. 26, 1995

[54] AMBULATORY INFUSION PUMP

[75] Inventors: Mary C. Dominiak, Chicago, Ill.;
Sheri A. Baltzer, Golden, Colo.;
Jeffrey P. Castleberry, Boulder, Colo.;
Warren P. Heim, Boulder, Colo.

[73] Assignee: Baxter International Inc., Deerfield, Ill.

[21] Appl. No.: 208,355

[22] Filed: Mar. 9, 1994

[51] Int. Cl.⁶ ................................................. F04B 43/08
[52] U.S. Cl. ........................................ 417/234; 604/153
[58] Field of Search .................................. 417/234, 474, 417/476, 477.1, 477.2, 360; 604/403, 408, 151, 153; 224/252, 253, 904; 206/570, 572, 438, 320

[56] References Cited

U.S. PATENT DOCUMENTS

| | | | |
|---|---|---|---|
| 3,158,300 | 11/1964 | Withee | 224/253 |
| 4,386,642 | 6/1983 | Durbin | 206/570 |
| 4,397,639 | 8/1983 | Eschweiler et al. | 607/153 |
| 4,416,595 | 11/1983 | Cromie | 417/476 |
| 4,559,038 | 12/1985 | Berg et al. | 417/474 |
| 4,565,542 | 1/1986 | Berg | 607/153 |
| 4,657,486 | 4/1987 | Stempfle et al. | 604/153 |
| 4,770,328 | 9/1988 | Dickhunt et al. | 224/252 |
| 4,796,790 | 1/1989 | Hamilton | 224/253 |
| 5,106,374 | 4/1992 | Apperson | 128/DIG. 12 |
| 5,168,892 | 12/1992 | Sunderland | 604/153 |
| 5,170,817 | 12/1992 | Sunderland | 128/DIG. 12 |
| 5,181,910 | 1/1993 | Scanlon | 604/151 |
| 5,336,190 | 8/1994 | Moss et al. | 417/477.2 |

FOREIGN PATENT DOCUMENTS

| | | | |
|---|---|---|---|
| 0542401 | 5/1993 | European Pat. Off. | 604/153 |

Primary Examiner—Richard A. Bertsch
Assistant Examiner—Peter G. Korytnyk
Attorney, Agent, or Firm—Mark J. Buonaiuto; Paul C. Flattery; Jay C. Nichols

[57] ABSTRACT

An ambulatory infusion pump system provides a continuous source of liquid medication to an ambulatory patient. The ambulatory infusion pump system includes a liquid medication reservoir (64) and a conduit (16) for conveying liquid medication from the reservoir to the patient. An ambulatory infusion pump (10) pumps liquid medication from the reservoir (64) to the patient (14) by manipulation of the conduit (16). A case (12) is provided for the ambulatory infusion pump (10) and the liquid medication reservoir (64). The case (12) includes a first chamber (440) receiving the ambulatory pump (10) and a second chamber (442) receiving the liquid medication reservoir (64). The first and second chambers are maintained in a juxtaposed position. An outlet through the case receives the conduit (16). A structure (74) is provided on the exterior of one of the first and second chambers for attaching the case to an upright support, with the second chamber (442) disposed between the first chamber (440) and the upright support.

8 Claims, 39 Drawing Sheets

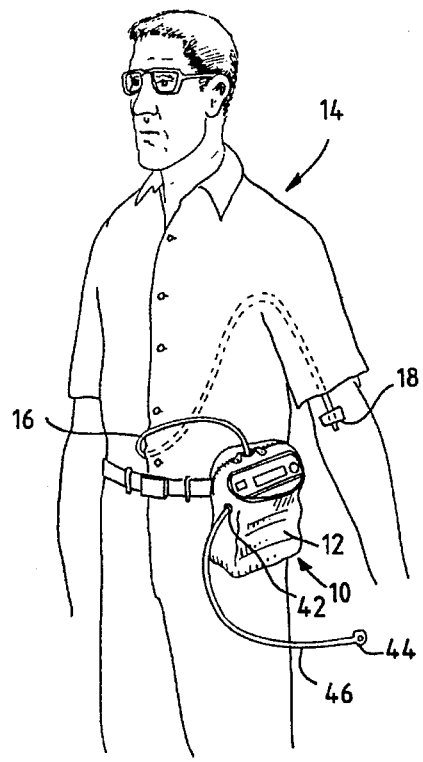
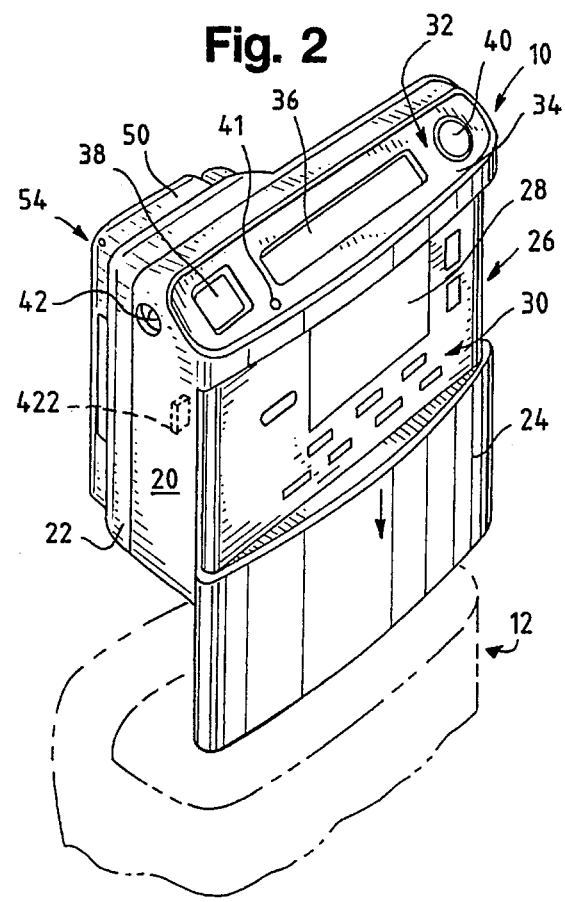
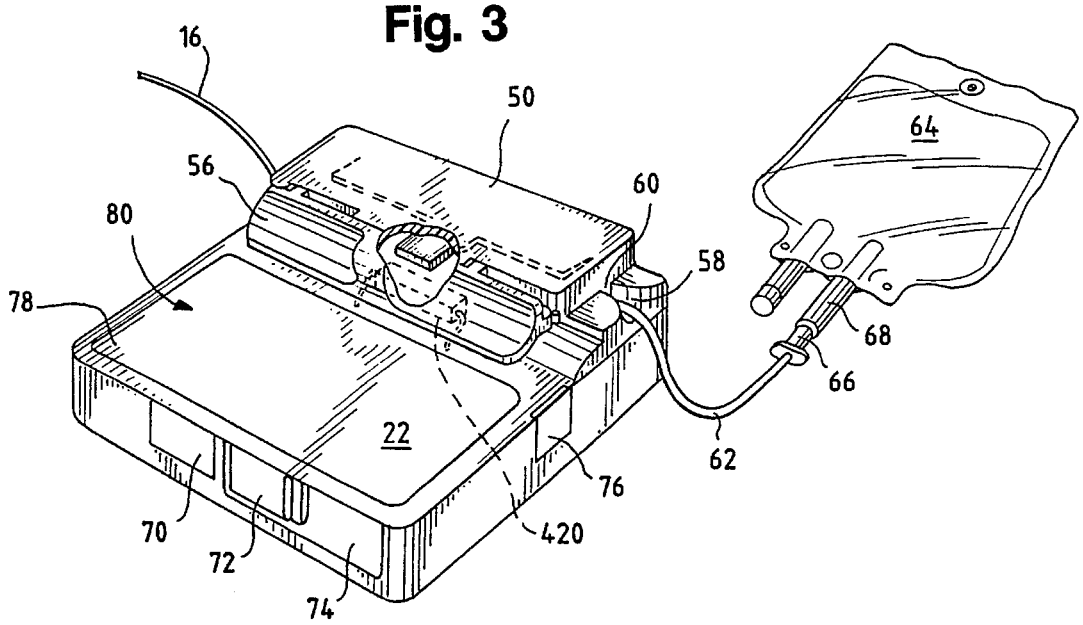

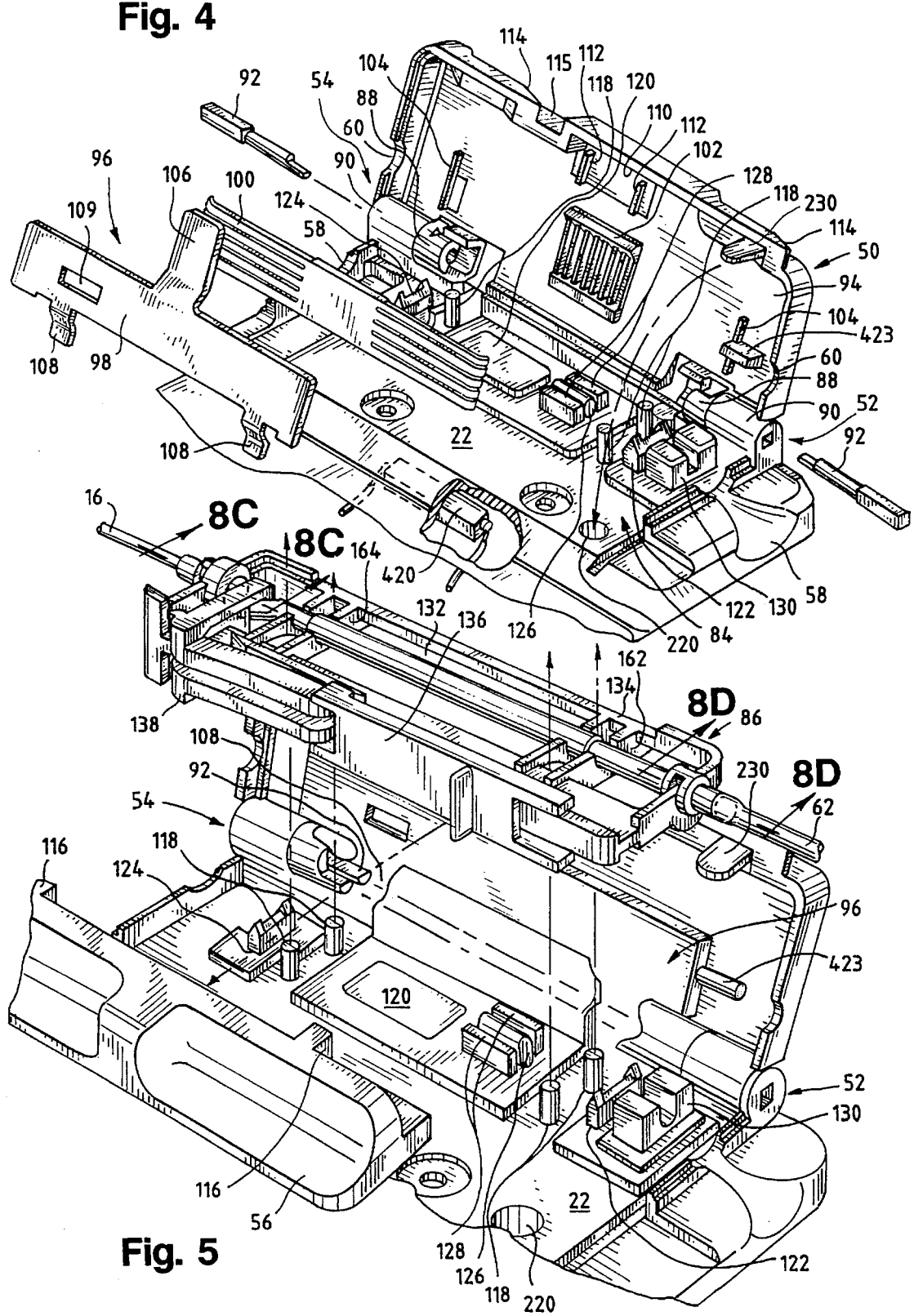

Fig. 38

| | | FLUID DELIVERY MODES | | | |
|---|---|---|---|---|---|
| | MODE 1 | MODE 2 | MODE 3 | MODE 4 | MODE 5 |
| | 0.1 - 0.4 mL/HR | 0.5 - 7.9 mL/HR | 8 - 49.9 mL/HR | 50 - 249 mL/HR | 250-390 mL/HR |
| | 20 -180 SEC/DELIVERY | 1.82 - 18 SEC/DELIVERY | 1.1 - 9 SEC/DELIVERY | 1.8 - 5.6 SEC/DELIVERY | 1.1 - 1.8 SEC/DELIVERY |
| | CLOSE DISTAL VALVE EACH DELIVERY 50µL STROKE | DELIVER IN 5 µL INCREMENTS | DELIVER IN 25 µL INCREMENTS | DELIVER IN 125 µL INCREMENTS | |
| | | DELIVERY FIRST FLUID INCREMENT BEFORE FILL TEST | | | |
| | DWELL BETWEEN VALVE CLOSURES | | | NO RETRACT ON FILL TEST | |
| | REFILL COMPENSATION | | | | CONCURRENT MOTOR OPERATIONS |

AMBULATORY INFUSION PUMP

BACKGROUND OF THE INVENTION

The present invention is directed toward a medical pump and, more particularly, toward an ambulatory infusion pump system.

BACKGROUND ART

Spiraling health care costs have led to the development of a variety of devices for facilitating administration of intravenous therapy to patients outside of a clinical setting. In addition, doctors have found that in many instances patients can return to substantially normal lives, provided that they can receive continuous intravenous administration of medication. These factors have combined to promote the development of lightweight, portable or ambulatory infusion pumps which can be worn by a patient and are capable of administering a continuous supply of medication at a desired rate.

A wide variety of ambulatory pumps in use in the medical field are intended to meet the need of a high degree of accuracy in the administration of fluids to maximize the effectiveness of medication and to protect the patient. Typically, these ambulatory infusion pumps include a pump control unit and drive mechanism including a variety of operating controls adapted to accept a disposable pump chamber assembly. The pump chamber assembly has an inlet end connected to a liquid reservoir and an outlet end connected to an I.V. tube which in turn is connected for intravenous administration to a patient by a cannula. One known pumping mechanism includes inlet and outlet valves and a single liquid displacement plunger, and will be referred to herein as a single plunger, two valve pump. Each pumping cycle in this type of pump begins with the outlet valve closed and the inlet valve open. Fluid flows from a source container into a section of tubing disposed between the inlet and outlet valve. After this section of tubing has filled with liquid, the inlet valve closes and the outlet valve opens. The plunger then compresses the short section of tubing between the valves, displacing the liquid contained therein and forcing it through the pump.

Known ambulatory infusion pumps provide a reservoir module and a pumping mechanism module which are attached together and, if desired, received within a carrying pouch which may be worn by an ambulatory patient. Such ambulatory infusion pump systems are known to be uncomfortable to the patient because they attach a rigid structure immediately adjacent to the patient. In addition, such systems provide little control to the temperature of the liquid within the fluid reservoir, which can have a deleterious effect upon a therapy being administered. Finally, the rigid reservoir module of such systems requires that, regardless of the amount of medication to be infused, the full weight and volume of the module must be borne by the patient.

The present invention is intended to overcome one or more of the problems discussed above.

SUMMARY OF THE INVENTION

An ambulatory infusion pump system provides a continuous source of liquid medication to an ambulatory patient. The ambulatory infusion pump system includes a liquid medication reservoir and a conduit for conveying liquid medication from the reservoir to the patient. An ambulatory infusion pump pumps liquid medication from the reservoir to the patient by manipulation of the conduit. A case is provided for the ambulatory infusion pump and the liquid medication reservoir. The case includes a first chamber receiving the ambulatory pump and a second chamber receiving the liquid medication reservoir. The first and second chambers are maintained in a juxtaposed position. An outlet through the case receives the conduit. A structure is provided on the exterior of one of the first and second chambers for attaching the case to an upright support, with the second chamber disposed between the first chamber and the upright support.

The system further provides the medication reservoir is a flexible solution bag defining a reservoir having a solution bag outlet connectable to the conduit at one end thereof. The flexible solution bag, when received in the second chamber, has the bag outlet folded over on the reservoir.

The ambulatory infusion pump system of the present invention maintains a flexible reservoir bag between the patient and the ambulatory infusion pump for increasing patient comfort when wearing the ambulatory infusion pump system. In addition, the system stabilizes the temperature of the liquid within the liquid reservoir by maintaining the liquid reservoir adjacent the body of the wearer and between the body of the wearer and the ambulatory infusion pump. Finally, the ambulatory infusion pump system of the present invention provides a case which is easily opened to receive the ambulatory infusion pump and a liquid reservoir and readily closable to secure the ambulatory infusion pump and the reservoir in the desired loaded position.

BRIEF DESCRIPTION OF THE DRAWINGS

FIG. 1 is a perspective view of a patient wearing an ambulatory infusion pump of the present invention;

FIG. 2 is a perspective view of the ambulatory infusion pump with the front cover slid to an open position;

FIG. 3 is a perspective view of the back of the ambulatory infusion pump with a solution bag in fluid communication with a pump cassette loaded into the ambulatory infusion pump;

FIG. 4 is an exploded perspective view of the pump cassette receptacle of the ambulatory infusion pump;

FIG. 5 is a perspective view of the pump cassette receptacle and a pump cassette illustrating loading of the pump cassette into the pump cassette receptacle;

FIG. 38 is a table summarizing pump operation during the five fluid delivery modes;

DESCRIPTION OF THE PREFERRED EMBODIMENT

Figure 6:
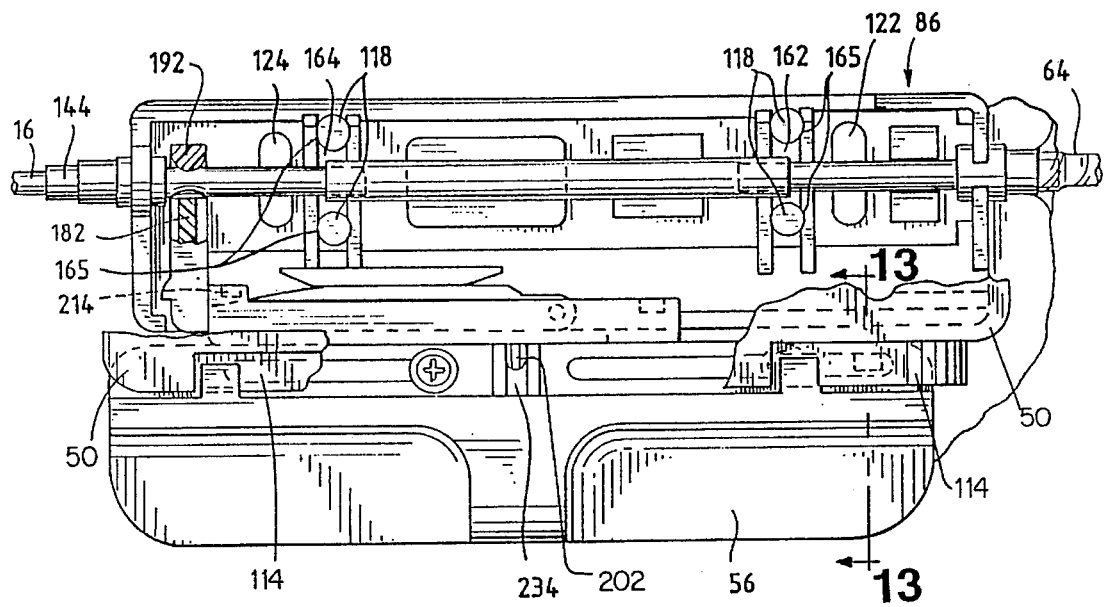
FIG. 6 is a partial plan view of the pump cassette received in the pump cassette receptacle of the present invention with a latch in a "closed" position and a cassette receptacle cover cut-away except by the latch.

FIG. 1 illustrates an ambulatory infusion pump (10) contained within a soft pump case (12) mounted to an ambulatory patient (14). The ambulatory infusion pump (10) is designed to provide a wide variety of drug delivery profiles so that a wide variety of therapies can be administered by the ambulatory infusion pump. The compact size and light weight of the pump facilitate a patient wearing the pump so that a continuous supply of medication can be delivered to the patient while the patient can engage in normal everyday activities. A flexible IV tube (16), which typically is made of PVC, extends between the pump (10) and a needle/catheter (18) for intravenous infusion of medication from the pump to the ambulatory patient. The ambulatory infusion pump (10) is usable in other applications where the distal end of the IV tube is connected to some other apparatus disposed downstream of the pump (10).

A. Pump Housing

The pump housing is designed for ease of patient and clinician use as well as patient comfort when the ambulatory pump (10) is worn. FIGS. 2 and 3 illustrate the pump housing. The ambulatory infusion pump (10) includes a rigid housing front (20) and a rigid housing back (22) which are preferably made of a high density rigid polymer such as polycarbonate and are joined by a continuous tongue and groove interface around their peripheries. A front cover (24) is slidably mounted to the rigid front housing (20) to selectively cover and uncover a control panel (26) on the rigid housing front (20). The control panel (26) includes an LCD programmer display (28) and a keyboard (30). The front cover (24) therefore protects and conceals the control panel to prevent inadvertent actuation of the keyboard (30). Detents (not shown) may be provided on the front cover (24) to maintain the front cover in a position coveting or not covering the control panel (26). The keyboard (30) are membrane switch panels. A user control panel (32) is located on a beveled front surface (34) of the rigid housing front (20). The user control panel (32) includes a patient display (36), a start/stop button (38) and a bolus dose control button (40). An LED (41) is provided on the user control panel (32) for providing a visual alarm or alert. Also on the rigid housing front (20) is a remote bolus switch contact (42) to which a remote bolus switch (44) can be coupled by means of electrical contact wire (46) (see FIG. 1). The pump is programmable so that a patient may use the bolus dose control button (40) or the remote bolus switch (44) to self-administer a bolus of medication, as for example in patient-controlled analgesic (PCA) therapies. Programming of the pump (10) will be discussed in greater detail below.

The rigid housing back (22) is best illustrated in FIG. 3. A cassette, door (50) made of a rigid polymer such as glass-filled polycarbonate is pivotably attached to the rigid housing back (22) by a pair of hinges (52,54) (see FIGS. 4 and 5). A latch (56) is slidably mounted to the rigid housing back (22) to selectively capture and release the cassette door (50) in a manner which will be discussed in detail below. A channel (58) in the rigid housing back (22) cooperates with a hemispherical slot (60) in the cassette door (50) to define a passage for receiving the IV tubing (62) in fluid communication with a fluid supply such as a solution bag (64). As illustrated in FIG. 3, the flexible tubing (62) is brought into fluid communication with the solution bag (64) by means of a spike (66) received in the solution bag outlet (68).

As seen in FIG. 3, between the rigid housing front (20) and the rigid housing back (22) is an infrared or IR window (70) made of molded tinted plastic which allows transmission of an IR signal to and from the ambulatory infusion pump (10). A sliding battery door (72) permits access to a cavity (74) which receives a 9 V battery (not shown) to provide electric power to the ambulatory infusion pump (10). An on/off switch (76) to power "on" or "off" the ambulatory infusion pump (10) is also provided. A rear panel (78) on the rigid housing back (22) bears an instruction label (80) consisting of an adhesive coated polyester. The polyester instruction label (80) also functions to cover mechanical access holes in the rigid housing back (22) so as to provide a moisture barrier.

FIG. 4 and 5 illustrates a portion of the rigid housing back (22) including the cassette door (50) pivoted open about the hinges (52,54) to reveal a pump cassette receptacle (84) for receiving a pump cassette (86) in a manner discussed below. As seen in FIG. 4, the cassette door (50) has a pair of hinge knuckles (88) laterally spaced from one another. The hinge knuckles (88) are received between a pair of hinge knuckles (90) on the rigid housing back (22). A pair of hinge pins (92) are received within lengthwise holes in the hinge knuckles (88,90) to pivotably secure the cassette door (50) to the rigid housing back (22).

The cassette door (50) defines an inner recess (94) which contains a floating platen assembly (96). The floating platen assembly (96) consists of a rigid metal platen (98) which is biased away from the cassette door (50) by a plurality of leaf springs (100) in lengthwise side-by-side relation. The leaf springs (100) are received between a lateral leaf spring bracket (102) and a pair of longitudinal leaf spring brackets (104) integrally formed with and extending from the door (50) which selectively restrain the leaf springs (100) from lateral or lengthwise movement relative to the cassette door (50). In the preferred embodiment, only four leaf springs are required for proper pump operation, although five are provided to provide a margin of safety in the event one or the springs fails.

The platen (98) has a tab (106), a pair of hinge hooks (108) and a lengthwise hole (109). The tab (106) is received within a cavity (110) in the inner recess (94) of the cassette door (50) and secured against lengthwise movement by a pair of posts (112). The hinge hooks (108) captively receive the hinge pins (92) in the manner best illustrated in FIG. 5 both to secure the platen (98) within the inner recess (94) and to confine the leaf springs (100) within the inner recess (94).

The cassette door (50) further includes at its front a pair of spaced lateral cam surfaces (114) each having a gap (115) at the bottom of the cam surface. A complementary pair of engagement pins (116) on the latch (56) are configured to engage the lateral cam surfaces (114) and drive the cassette door (50) toward the pump cassette receptacle (84) as the latch is moved from fight to left, as viewed in FIGS. 6 and 7, and to hold the cassette door (50) shut.

Extending into the pump cassette receptacle (84) through the rigid housing back (22) are four registration pins (118), a plunger (120), an inlet valve pincher (122), an outlet valve pincher (124), a pressure transducer button wedge (126) having an arcuate leading edge (127) received between a pair of guide posts (128) and an ultrasonic air detector (130). The registration pins (118) are made of a rigid material such as aluminum or steel and the plunger (120), the inlet and outlet valve pinchers (122,124) and pressure transducer button wedge (126) are preferably made of self-lubricating polymer to minimize potential binding and to maximize cleanability. At opposite ends of the leading edge of the inlet and outlet pincher valves are a pair of stops (131) (see FIGS. 9–11A).

The registration pins (118) are configured to engage the platen (98) and drive its against the bias of the leaf springs (100) into the inner recess (94) so as to position the platen (98) a select distance from the plunger (120) for reasons which will be discussed in greater detail below.

B. Pump Cassette

As seen in FIGS. 5–8D, the pump cassette (86) includes an elastomeric conduit or a pump chamber assembly (132), a rigid frame (134), a slider (136) and a pincher (138) which are snap fit together. The pump cassette (86) facilitates quick and easy positioning of the pump chamber assembly (132) relative to plunger (120) and inlet and outlet valve pinchers (122,124) as well as an anti-free flow structure.

Figure 8A:
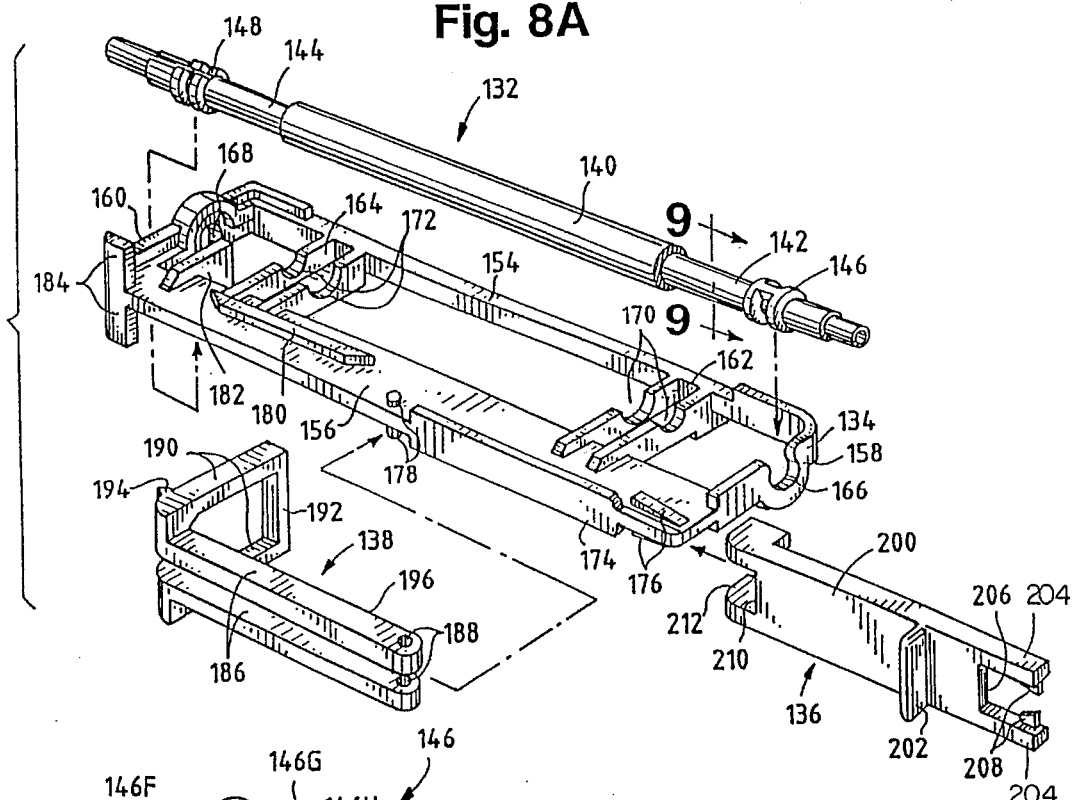
FIG. 8A is an exploded perspective view of the pump cassette.

Referring to FIG. 8A, the elastomeric conduit or pump chamber assembly (132) consists of a pump chamber (140) made of polyurethane robing, an inlet valve tube or adaptor (142) and an outlet valve tube or adaptor (144) both made of low durometer polyvinylchloride (PVC), and identical inlet and outlet clips (146,148). Polyurethane was selected for the pump chamber because of its ability to rebound and its stiffness. Low durometer PVC was selected for the inlet and outlet valve tubes because it requires relatively little energy to compress so as to completely occlude the inlet and outlet valve tubes. These material properties combine to optimize the pump chamber assembly (132) operation and to minimize battery power required to pump fluid through the pump chamber assembly (132).

The polyurethane pump chamber (140) exhibits greater rebound than PVC tubing typically used in ambulatory infusion pumps. The ability to rebound is particularly important with respect to the pump chamber because the pumping mechanism relies upon the resilience of the pump chamber material to return the pump chamber to an uncompressed state, thereby creating a negative pressure for refill of the pump chamber. The refill cycle is the limiting factor in the pumping sequence for volume output. If the material does not return to its natural state quick enough, then the pump chamber will be underfilled, causing a decrease in volumetric output which degrades pump accuracy. The polyurethane is also stiffer than convention PVC tubing, creating a hydraulically rigid section that resists volume changes due to system pressure variances. As a result, the pump chamber (140) resists "ballooning" with an increased back pressure which could affect output volumes and thus the accuracy of the pump. "Ballooning" refers to a condition where extension of the plunger into the pump chamber causes the non-compressed potion of the pump chamber to elastically expand, thereby resulting in a volume of liquid discharged from the pump chamber which is less than the volume of liquid displaced by the plunger. To compensate tier the stiffer material and the increased energy required to compress the stiff pump chamber, wall thickness of the tubing has been minimized. In the illustrated embodiment, the polyurethane pump chamber (140) has a durometer of 80 shore A, an inner diameter of 0.157 inches and an outer diameter of 0.193 inches. Polyurethane has the additional advantage of being readily solvent bonded to a variety of materials, including PVC.

The rebound of an elastomer is measured by its tan Δ, which is defined as the viscous response divided by the elastic response of the material at a select temperature. The smaller the tan Δ the greater the rebound propensity. A desirable material for a pump chamber has a tan Δ which remains relatively low through the range of operating temperatures. For the present invention, the range of operating temperatures is between approximately 32°–110° F. (0°–45° C).

Figure 42:
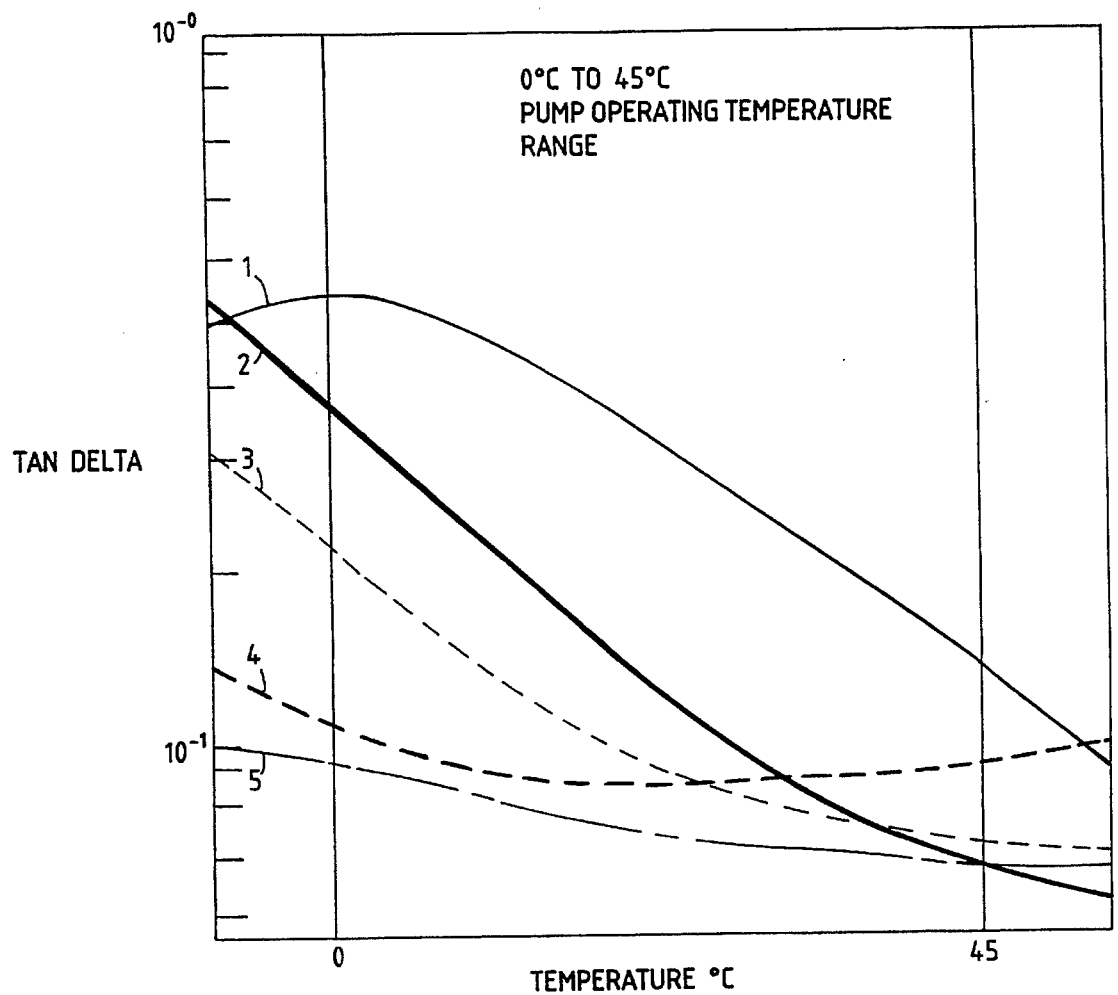
FIG. 42 is a graph of DMA tan Δ of a variety of pump tubing materials.

FIG. 42 is a graph of Dynamic Mechanical Analysis ("DMA") tan Δ versus temperature for a number of materials. PVC tubing is commonly used with peristaltic type pumps. Over the range of operating temperatures, DMA tan Δ of a low durometer PVC varies between about 0.4–0.07 and the DMA tan Δ of a high durometer PVC varies between about 0.4 to 0.2. As can be seen in FIG. 42, the DMA tan Δ of polyurethane ranges between about 0.2–0.08. Thus, polyurethane has a lower tan Δ than the tested PVC's over the range of operating temperatures.

In order to ensure a constant output volume, material stiffness should remain relatively constant over the range of operating temperatures. A constant stiffness provides a construct energy requirement for compressing the tubing over the range of operating temperatures and also ensures that the stiffness required to resist "ballooning" over the range of operating temperatures is maintained.

Figure 43:
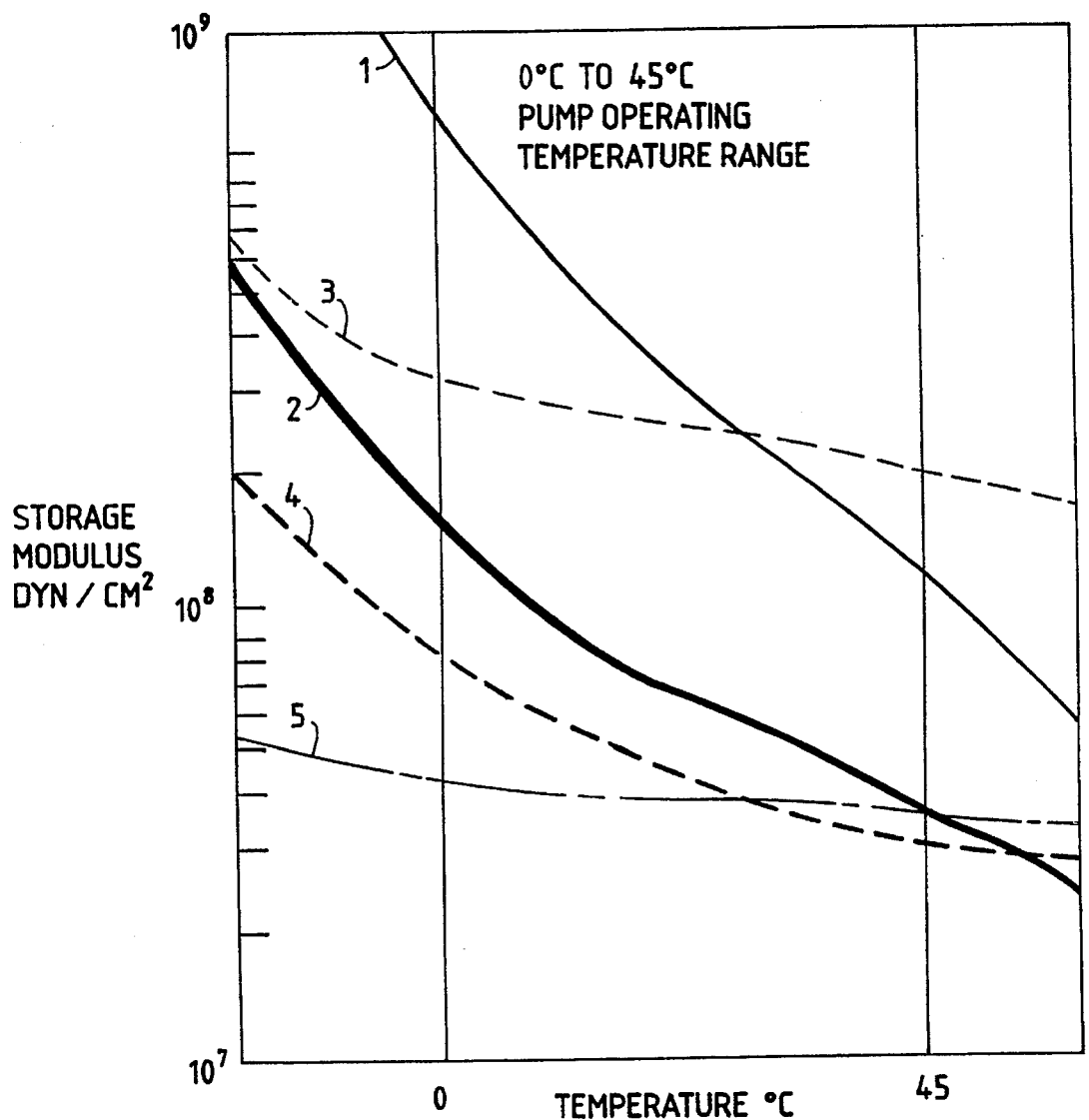
FIG. 43 is a graph of DMA stiffness of a variety of pump tubing materials.

As appreciated by those skilled in the art, "stiffness" is a function of storage modulus and tube geometry. FIG. 43 is a graph of DMA storage modulus of pump tubing versus temperature for five materials. As seen in FIG. 43, polyurethane has a relatively constant storage modulus of $10^8$ dyne/cm$^2$ over the range of operating temperatures, meaning it will have a relatively constant stiffness.

It can be observed from the tables that silicone has the desirable features of a relatively constant storage modulus or stiffness and a relatively low tan Δ over the range of operating temperatures. However, silicone is extremely difficult to solvent bond to other materials, and therefore is not suitable for use as a pump chamber with the present invention which requires a bond between the pump chamber (140) and the PVC inlet and outlet valve tubes (142,144), so as to provide pump chamber and valve tube materials which optimize pump performance.

The inlet valve tube (142) and outlet valve tube (144) each have a lesser inner and outer diameter than the pump chamber (140). As illustrated in FIG. 8A, the inlet valve tube (142) and outlet valve tube (144) are telescopically received within the opposite ends of the inner diameter of the pump chamber (140) and are solvent bonded thereto. The inlet and outlet valve tubes (142,144) are preferably made of a PVC having a durometer between 30 and 60 shore A, with a durometer of 50 shore A being preferred. Relatively thick walls and a lower durometer are preferred to lessen the energy required to pinch off the lumens of the inlet and outlet valve tubes (142, 144). In the illustrated embodiment, the inlet and outlet valve tubes (142, 144) have an outer diameter of about 0.163 inches and an inner diameter of about 0.083 inches.

Other elastomers which are chemically inert with respect to fluids to be delivered by the pump and which have similar physical characteristics to the polyurethane pump chamber (140) and the low durometer PVC inlet and outlet valve tubes may be suitable substitutes for these materials, and are considered to be within the scope of the invention.

Figure 9:
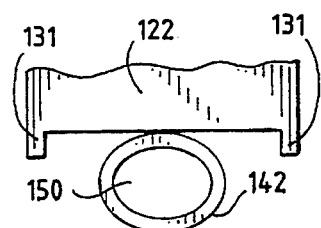
FIG. 9 is a sectional view of the inlet valve tube taken along line 9—9 of FIG. 8.
Figure 10:
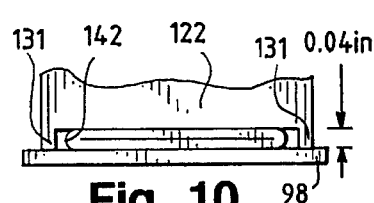
FIG. 10 is the inlet valve tube of FIG. 9 in a compressed state.
Figure 11B:
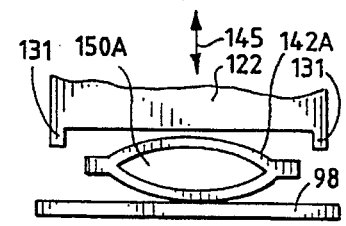
FIG. 11B is a section view of the alternative embodiment of the inlet valve tube taken along line 11B—11B of FIG. 11A including the platen and inlet pincher valve.

FIG. 9 illustrates a cross-section of the inlet valve tube (142) sandwiched between the inlet valve pincher (122) and the platen (98). The outlet valve tube (144) is identical and will not be separately discussed. During operation of the pump, the inlet valve robe (142) is repeatedly compressed to completely occlude the lumen (150), as illustrated in FIG. 10, and released to return to the partially deformed configuration shown in FIG. 9. Low durometer material is chosen for the inlet and outlet valve tubes to minimize the amount of energy required to fully close the lumen (150).

Figure 11A:
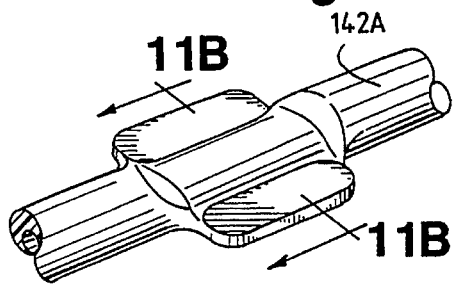
FIG. 11A is a perspective view of an alternative embodiment of the inlet valve tube.

FIG. 11A illustrates an alternative embodiment of the inlet valve tube (142A) with a deformed portion (143) intended to lie between the inlet pincher valve (122) and the platen (98). The deformed portion (143) has a football-shaped cross-section (150A), as best viewed in FIG. 11B. This shape removes the vertical wall of the tubing (142A) which must be crashed during the closure of the tubing. The tubing (142A) is mounted within the frame (134) with the minor axis aligned parallel to the directions of movement illustrated by arrow (145) between the valve pincher (122) and the platen (98). Thus, the inlet valve tube embodiment (142A) illustrated in FIGS. 11A and 11B further minimizes the energy required to occlude the lumen (150A). The inlet valve tube 142 (or 142A) is extruded or molded using conventional techniques. For example, standard tubing can be deformed by any known process such as RF welding, ultrasonic or pressure forming. The outlet valve robe (144) may be identical to the alternate embodiment of the inlet valve robe (142A) and will not be separately described.

Figure 7:
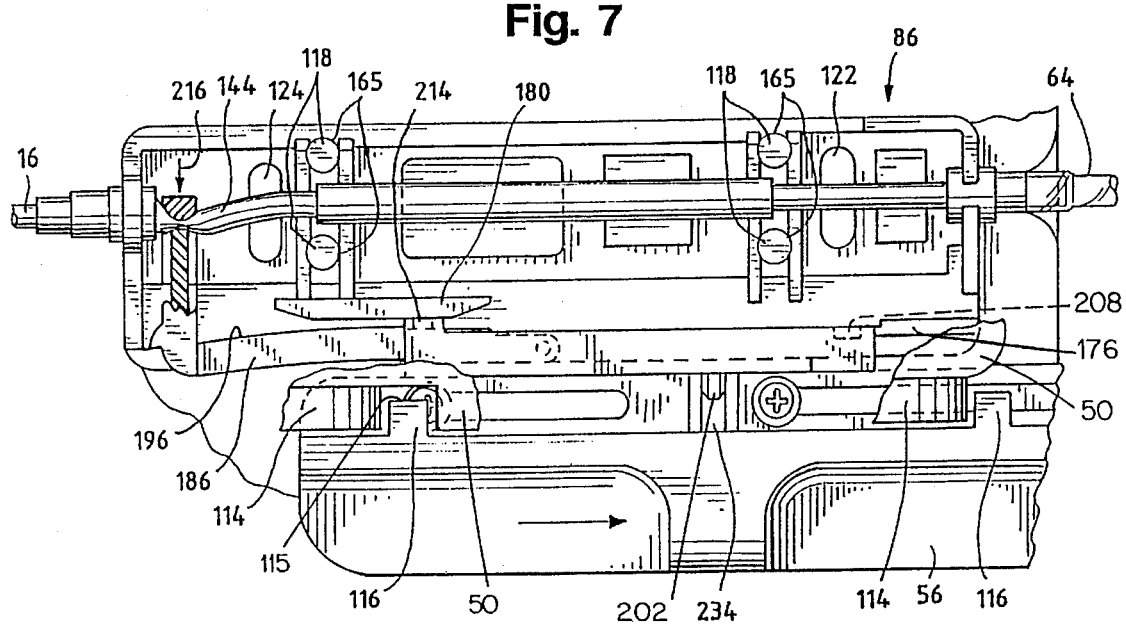
FIG. 7 differs from FIG. 6 only in that the latch is in an "open" position.
Figure 8B:
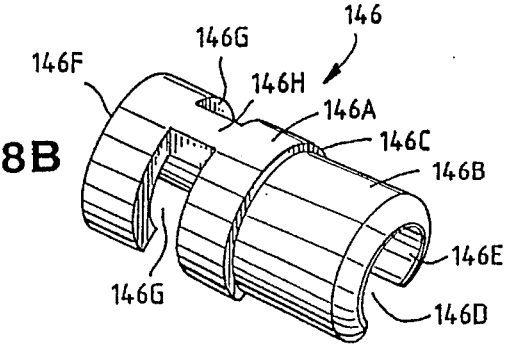
FIG. 8B is a perspective view of the clip of FIG. 8A.

An inlet clip (146) (which is identical to the outlet clip (148) which will not be separately described) is illustrated in detail in FIG. 8B. The inlet clip (146) includes a greater diameter cylindrical portion (146A) and a coaxial lesser diameter cylindrical portion (146B) with an arcuate step (146C) therebetween. The inlet clip further includes a lengthwise opening (146D) and open ends (146E) and (146F). Lastly, the inlet clip (146) includes a pair of arcuate gaps (146G) in the greater diameter portion separated by a land portion (146H). The arcuate gaps (146G) of the greater diameter cylindrical portion are received in the arcuate channels (166, 168) of the rigid frame (134) to secure the pump chamber assembly (132) to the rigid frame (134) (see FIGS. 6 and 7). The lesser diameter cylindrical portion (146B) provides a support to the inlet or outlet valve tubes (142,144) to prevent kinking thereof, as will be discussed below with reference to FIGS. 8C and 8D.

Figure 8C:
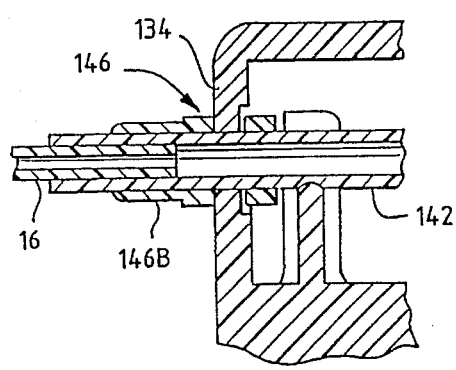
FIG. 8C is a cross-sectional view of the clip of FIG. 8B engaging the cassette frame taken along line 8C—8C of FIG. 5.

FIG. 8C illustrates bonding of a large bore tube (62) to the clip (146). The large bore tube (62) is axially slid over the valve tube (142) and the lesser diameter cylindrical portion (146B) and solvent bonded to the lesser diameter cylindrical portion (146B). In addition, the inlet valve tube (142) is solvent bonded to the interior of the inlet clip (146). Solvent bonding of the large bore tubing (62) to the lesser diameter cylindrical portion (146) not only provides strain relief in the event of axial or radial loads on the large bore tube (62), it also prevents kinking of the low durometer inlet vane tube (142) so as to decrease the risk of inadvertent occlusion of the inlet valve tube (142) lumen. In addition, engagement of the large bore diameter tube with the lesser diameter cylindrical portion in the manner described above provides a "Chinese finger trap" effect which helps to oppose axial removal of the large bore tube (62) from the clip (146).

Figure 8D:
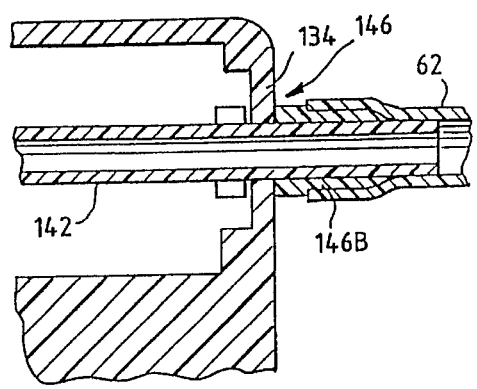
FIG. 8D is a cross-sectional view of the clip of FIG. 8B engaging the cassette frame taken along line 8D—8D of FIG. 5.

FIG. 8D illustrates connection of a small bore tube (16) to inlet valve tube (142). As illustrated in FIG. 8D, the small bore tube (16) is telescopingly received in the inlet valve tube (142) so as to extend into the inlet tube lumen at least as far as the small diameter cylindrical portion (146B) of the clip (146). In this manner, a strong solvent bond between the tubes (16, 142) is assured. In addition, insertion of the small bore tube (16) this amount assures the inlet valve tube (142) will not be subject to kinking if a tangential load is applied.

Referring to FIG. 8A, the rigid frame (134) is molded from a thermoplastic resin, preferably ABS. The frame (134) includes a first longitudinal member (154), a second longitudinal member (156), an inlet end wall (158) and an outlet end wall (160) integrally joined in a rectangular configuration. Integral first and second support webs (162,164) having alignment holes (165) (see FIGS. 6 and 7) extend between the first and second longitudinal members to improve the rigidity of the rigid frame (134). The inlet and outlet end walls (158,160) each define arcuate channels (166,168), respectively, which open in opposite directions. As illustrated in FIG. 8A, 8C, and 8D, the clips (146,148) are received within the arcuate slot (166,168) to secure the pump chamber assembly (132) to the rigid frame (134). Guide channels (170,172) are defined in the support webs (162,164), respectively, to further support the pump chamber assembly (132) within the rigid frame (134).

An integral guide rail (174) extends longitudinally along an outer edge of the second longitudinal member (156). Integrally formed on the second longitudinal member (156) proximate the inlet end wall (158) are a pair of ramped bumpers (176) extending in opposite directions from both sides of the second longitudinal member. A pair of integrally formed pivot pins (178) extend in opposite directions at approximately the center of the second longitudinal member (156). An integral pair of ramped cam rails (180) extend longitudinally from the second longitudinal member (156) proximate an inner edge and the inlet end wall (158) of the second longitudinal member (156). Proximate the outlet end wall (160) an integral anvil (182) extends from the second longitudinal member (156) toward the first longitudinal member (154). Finally, a pair of integral stops (184) extend in opposite directions transverse of the second longitudinal member adjacent to the outlet end wall (160).

The pincher (138) includes a pair of parallel spaced legs (186) each having a pivot hole (188) at one end and a pair of transverse legs (190) joined by a bridge (192) at their other end. A pair of stops (194) (one shown in FIG. 8) extend lengthwise from the pincher (138) at the base of each of the legs (190). Each leg (186) includes a cam surface (196).

The slider (136) has a generally rectangular body (200) having a transverse outwardly extending gripper bar (202) thereon. A pair of legs (204) extend lengthwise from a first end (206) of the rectangular body (200). At a distal end of each of the legs (204) is a ramped stop (208) which extends inwardly toward the other leg. At the second end (210) of the rectangular body (200) are a pair of lengthwise and inwardly extending legs (212) each having a camming pin (214) (see FIGS. 6 and 7) which extends inward toward the other of the inwardly extending legs (212).

Figure 12:
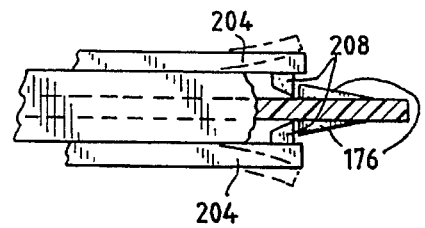
FIG. 12 is a sectional view of the slider stop of the pump cassette.

Assembly of the pump cassette (86) is best understood with reference to FIG. 8A. The pump cassette (86) is assembled by first aligning the pump chamber assembly (132) with the arcuate slots (166,168) of the end walls (158,160) and the guide channels (170,172) of the support webs (162,164). The inlet clip (146) is then force fit into the open end of the arcuate slot (166) of the inlet end wall (158) and the outlet clip (148) is tucked under the outlet wall (160) and force fit within the arcuate slot (168) of the end wall (160), and both the inlet and outlet clips (146,148) are solvent bonded in place. With the pump chamber assembly (132) so engaged to the rigid frame (134), any longitudinal strain on the pump chamber assembly (132) is borne by the clips (146,148) and transferred to the rigid frame (134), thus protecting the pump chamber assembly (132) from such strains. The pincher (138) is then attached to the frame (134) by feeding the outlet valve tube (144) between the legs (186) so that the outlet valve tube (144) rests between the transverse legs (190) and the bridge (192). The holes (188) are then positioned to receive the pivot pins (178) on the second longitudinal member (156). In this manner, the pincher (138) is allowed to pivot relative to the rigid frame (134). Finally, the slider (136) is fed onto the guide rail (174) as illustrated in FIG. 8A. More particularly, the second end (210) lies over the guide rail (174) with the camming pins (214) being received between the ramped cam rails (180) and the cam surface (196) of the legs (186) of the pincher (138). With reference to FIG. 12, as the slider (136) is further slid onto the guide rail (174), the ramped stops (208) engage the ramped bumpers (176), deflecting the legs (204) outwardly with respect to each other until the ramp stops (208) reach the end of the ramped bumpers (176), at which point the legs (204) snap inwardly with respect to each other, securing the slider (136) to the guide rail (174).

C. Anti-Free Flow

The pump cassette (88), the cooperation between the pump cassette (88) and the cassette receiving chamber (84), the door (50), the latch (56) and the inlet and outlet pincher valves (122,124) combine to prevent inadvertent free flow during loading and unloading of the pump cassette (86).

With the pump chamber/valve assembly assembled as discussed above, the slider (136) is free to slide back and forth on the guide rail (174) between an open position where the end of the longitudinally and inwardly extending legs (212) abut the base of the transverse legs (190) of the pincher (138) (see FIG. 6) and a closed position where the ramped stops (208) abut the ramped bumpers (176) (see FIG. 7). FIG. 6 illustrates the pump cassette. (86) with the slider (136) in the "open" position and FIG. 7 illustrates the pump cassette (86) with the slider (136) in the "closed" position. In both FIGS. 6 and 7 the cassette cover (50) is shown cut-away except in the vicinity of the latch (56) for clarity. With the slider (136) in the open position, the camming pin (214) is out of engagement with the cam surface (196) of the pincher (138) and the ramped cam rails (180) of the frame (134). The resilient properties of the outlet valve tube (144) are thus able to bias the pincher bridge (192) away from the anvil (182) to open the lumen of the outlet valve tube (144) so as to permit flow of fluid through the pump chamber assembly (132). As the slider (136) is moved from left to right toward the closed position as viewed in FIGS. 6 and 7, the camming pin (214) engages the camming surface (196) of the pincher legs (186) and then further engages the ramped cam rail (180) causing the pincher (138) to pivot downward as viewed in FIG. 7 and illustrated by the arrow (216) so as to pinch the outlet valve (144) and occlude its lumen (150), preventing flow of fluid through the pump chamber/valve assembly.

Figure 13:
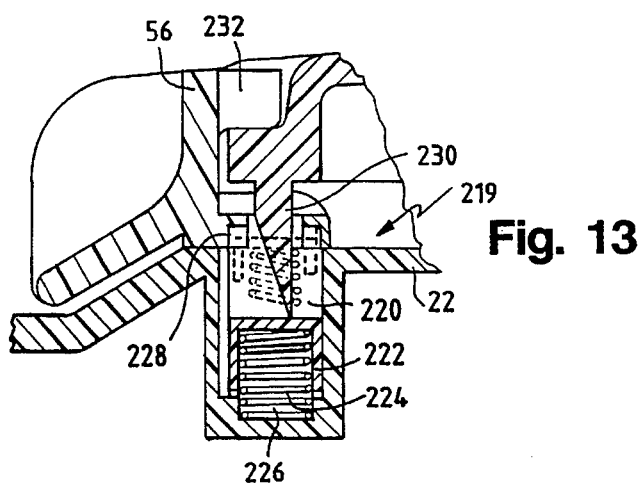
FIG. 13 is a sectional view of a latch detent of the present invention taken along line 13—13 of FIG. 6.
Figure 14:
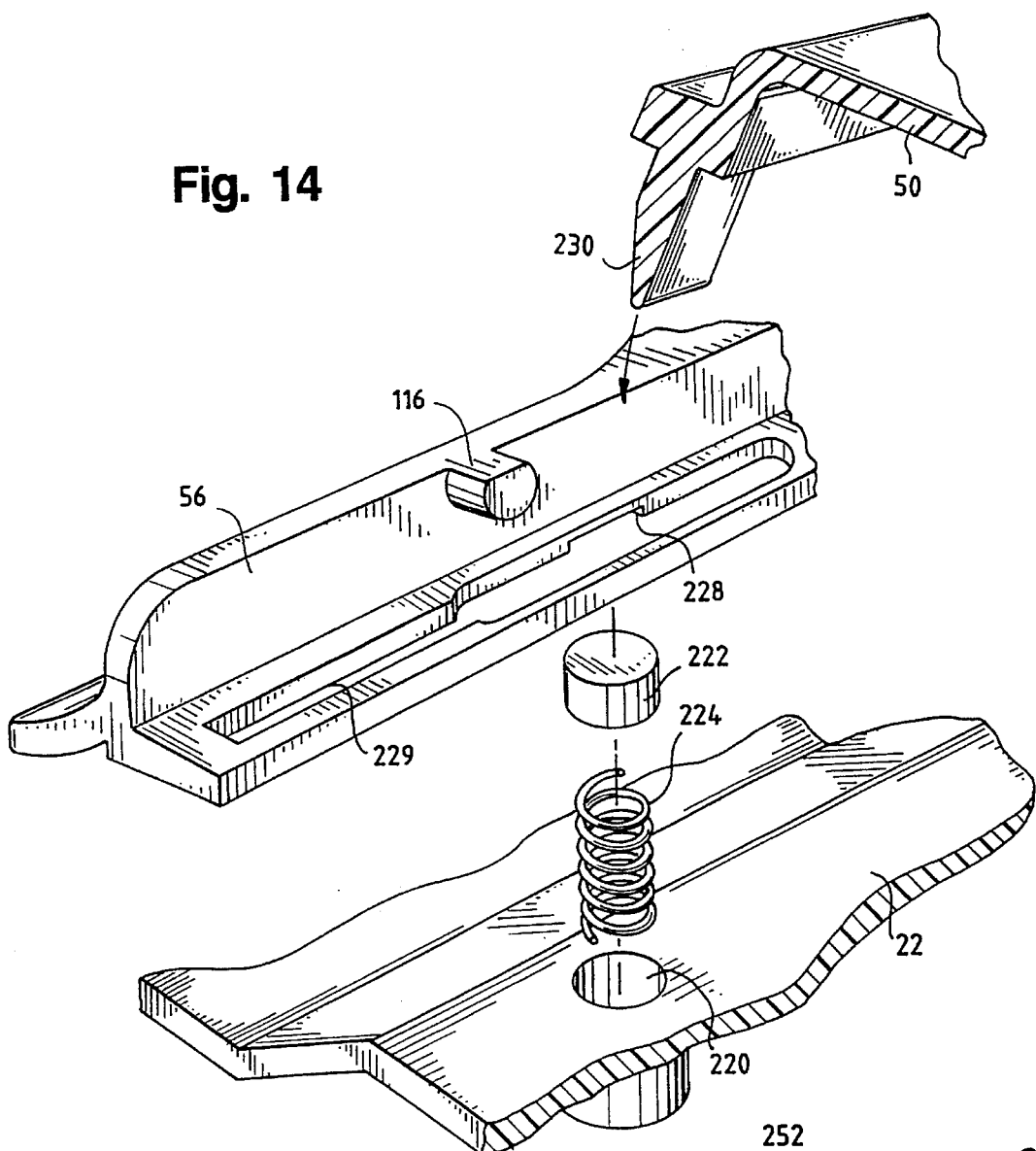
FIG. 14 is an exploded sectional perspective view illustrating interaction of the sliding latch, latch detent and spike.

Referring to FIGS. 13 and 14, the ambulatory infusion pump (10) includes a detent assembly (219) for user convenience to position and maintain the latch in an "open" position until the cassette door (50) is closed. As seen in FIGS. 4, 5, and 14, within the pump cassette receptacle (84) a cylindrical hole (220) extends into the rigid housing back (22). As best seen with reference to FIG. 13, a latch detent piston (222) resides in the cylindrical hole (220). The latch detent piston (222) is biased upward by a latch detent spring (224) affixed to the rigid housing back (22) within a reduced diameter portion (226) of the cylindrical hole (220). With the latch (56) slid to an open position, the latch detent piston (222) is received within a cavity (228) in the bottom of the latch (56) as illustrated by the phantom lines in FIG. 13. The cavity (228) of (56) (see FIG. 14) is formed at one end of an elongate slot (229) in the latch (56). With the latch detent piston (222) received in the cavity (228), the latch (56) cannot slide to the left so as to fasten the cassette door (50) closed. A spike (230) extends normally and inwardly from the cassette door (50). As illustrated in FIGS. 4 and 8, with the cassette door (50) closed, the spike (230) is received within the cylindrical hole (220) referring to FIG. 13, the tip of the spike (230) forces the latch detent piston (222) into the cylindrical hole (220) and out of engagement with the cavity (228) in the bottom of the latch (56), allowing the latch (56) to be slid to the left, as illustrated in FIG. 6, with spike (230) received in the slot (229). In this manner the engagement pins (116) come into sliding engagement with the lateral cam surfaces (114) of the cassette door (50) so as to bias the cassette door (50) toward the pump cassette receptacle (84) and to secure the cassette door (50) closed.

Loading of the pump cassette (86) into the pump chamber receptacle (84) is best illustrated with reference to FIGS. 5–8A. To load the pump cassette (86) into the pump cassette receptacle (84), the latch (56) is slid to the right as viewed in FIGS. 6 and 7 (and to the left as viewed in FIG. 14) sufficiently for the latch detent piston (222) to be received within the cavity (228) of the latch (56). This position is illustrated in FIG. 7 and in phantom lines in FIG. 13. As seen in FIG. 7, in this position the lateral cam surfaces (114) of the cassette door (50) clear the engagement pins (116) so that the cassette door (50) may be opened or closed. In addition, in order to insert the pump cassette (86) into the pump cassette receptacle (84), the slider (136) must be fully slid to the right (as seen in FIG. 7) and in the closed position with the ramped stops (208) abutting the ramped bumpers (176). Only with the slider so positioned can the gripper bar (202) be received within the slot (234) of the latch (56). The pump cassette (86) is received within the pump cassette receptacle (84) by aligning the gripper bar (202) with the slot (234) of the latch (56) and by aligning the registration pins (118) with the slots (165) of the support webs (162,164). Alignment of the registration pins (118) with the slots (165) has the desirable effect of precisely positioning the pump chamber/valve assembly with respect to the inlet valve pincher (122), the outlet valve pincher (124), the plunger (120), the pressure transducer button wedge (126) and the ultrasonic air detect (130) to ensure proper conveyance during pumping of fluid through the pump chamber/valve assembly and error detection.

With the pump cassette (86) so loaded, the cassette door (50) can be pivoted downward with the engagement pins (116) received within the gaps (115) at the distal edge of the cassette door (50) proximate the bottom of the lateral cam surfaces (114). At the same time, the spike (230) is received within the cylindrical hole (220) forcing the latch detent piston (222) downward and out of contact with the cavity (228) of the latch (56). With the lid so closed, the latch (56) can then be slid to the left, or toward the "locked" position illustrated in FIG. 6. As the engagement pins (116) ride up the lateral cam surfaces (114) the platen (98) is moved close enough to the inlet and outlet valve pinchers (122,124) to fully occlude the inlet and outlet valve tubes (142,144). Only after the inlet and outlet valve tubes (142,144) are occluded is slider (136) moved sufficiently to reach the "open" position illustrated in FIG. 6 wherein the pincher is in a non-occluding position. As the latch (56) is then moved toward the right as illustrated in FIG. 7, the slider (136) causes the pincher (186) to occlude the outlet valve tube (144) before the inlet or outlet valve pinchers (122,124) cease occluding the inlet and outlet valve tubes. In this manner, free-flow through the cassette is prevented during loading and unloading of the cassette.

As the cassette door (50) is closed, the platen (98) is forced into the inner recess (94) of the cassette door (50) by the registration pins (118). The platen is thereby spaced from the piston (120) so the space between the piston (120) surface and the platen varies between precise select distances with the piston fully extended and the piston fully withdrawn to ensure a uniform discharge and full volume of the pump chamber during a pumping cycle. The floating platen and registration pins cooperate to eliminate "tolerance stacking" between the platen (98) of the cassette door (50) and the pump driving mechanism (250).

The cassette (86) can be inserted into the pump cassette receptacle (84) and the cassette door (50) subsequently closed only with the slider (136) initially in the "closed" position and the outlet valve tube (144) pinched shut, thereby preventing inadvertent free flow of fluid to a patient during loading of the cassette (86). If the slider (136) is not in the closed position upon loading the cassette (86), the cassette door (50) will be prevented from closing because the engagement pins (116) will strike the lateral cam surfaces (114) of the cassette door (50). This feature assures that at least one of the inlet or outlet pincher valve pinchers (122,124) will be occluding the lumen of the inlet or outlet valve tubes (142,144) when the door (50) is closed and the latch (56) is moved from the open to the closed position, again preventing inadvertent free flow of fluids to a patient.

D. Pumping Mechanism

Figure 15:
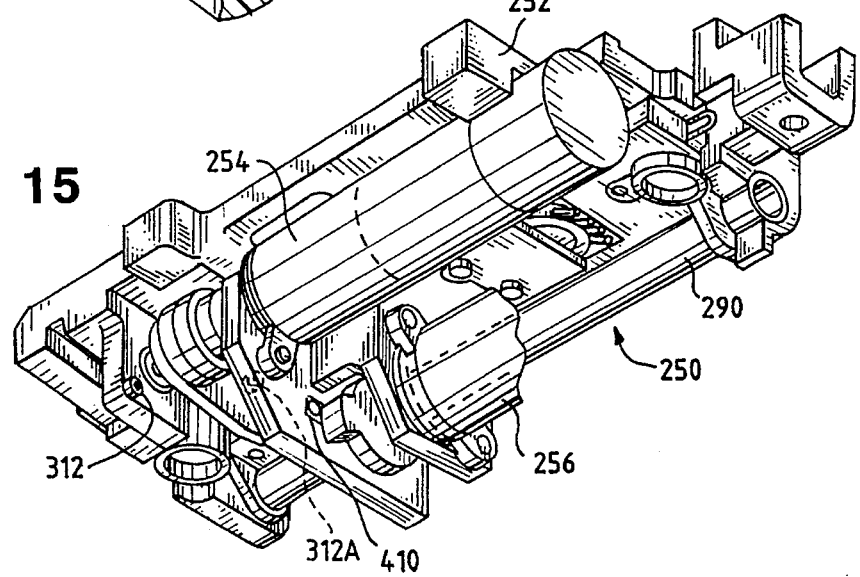
FIG. 15 is a perspective view of a pump driving mechanism of the present invention with a portion of a plunger motor removed for clarity.
Figure 16:
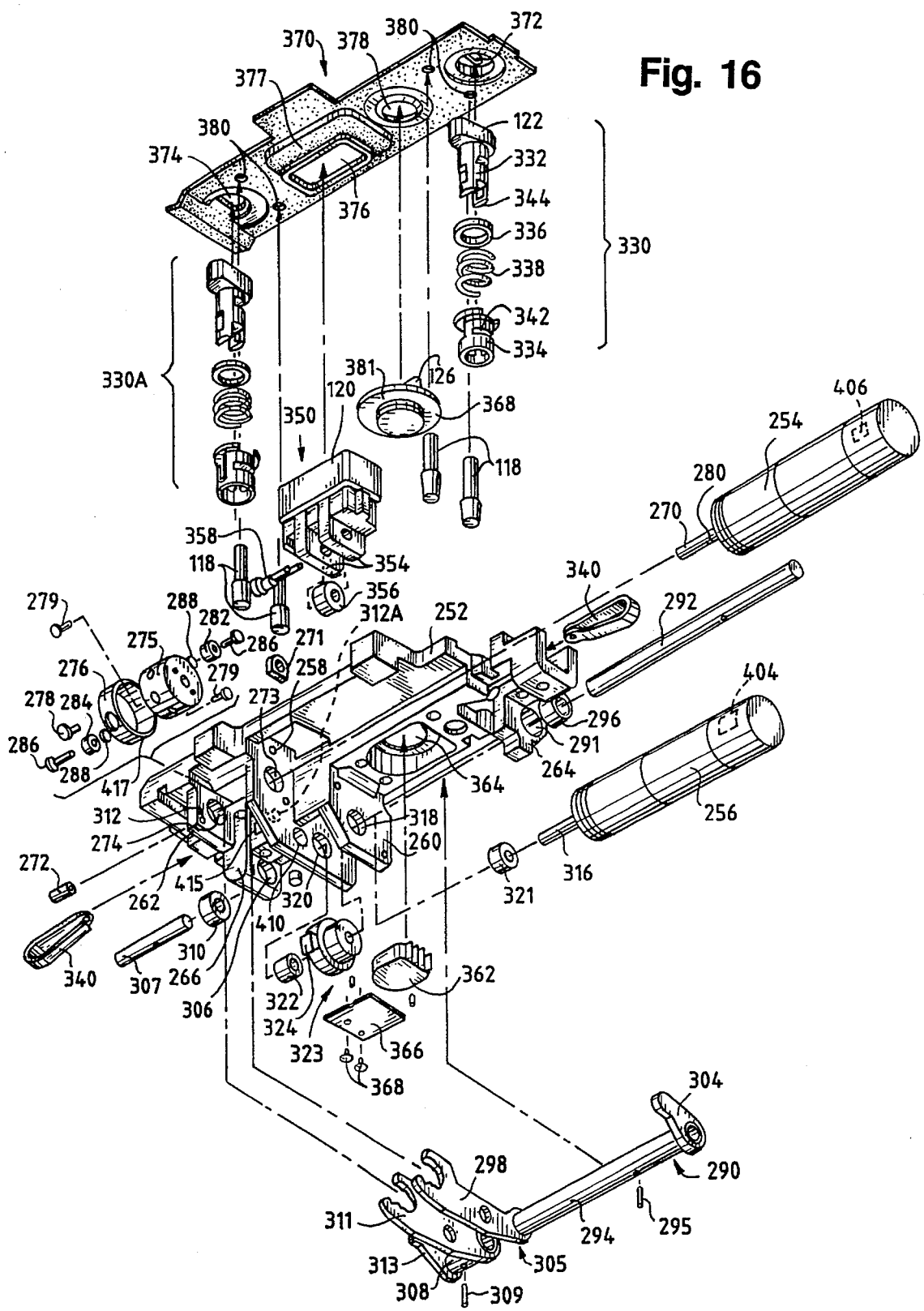
FIG. 16 is an exploded perspective view of the pump driving mechanism.

The ambulatory infusion pump includes a pump driving mechanism (250) generally illustrated in FIGS. 15 and 16 which acts on the pump chamber assembly (132) to propel fluid therethrough. The pump driving mechanism (250) is generally illustrated in FIGS. 15 and 16 and includes an assembly frame (252) to which the valve motor (254) and the plunger motor (256) are attached. The assembly frame (252) includes a central boss (258), a plunger motor support boss (260), a valve drive shaft support boss (262), an inlet valve support boss (264), an outlet valve support boss (266), and an intermediate valve support boss (268).

The valve motor (254) is a DC electric motor secured to the central boss (258) with the valve drive shaft (270) received in bushings (271,272) in axially aligned bores (273,274) in the central boss (258) and the valve drive support boss (262). A crank carrier (275) rides on the valve drive shaft (270) between the central boss (258) and the valve drive support boss (262) and a flag ring (276) having a knurled finish surrounds the outer periphery of the crank carrier (275). A set screw (278) secures the flag ring (276) to the crank carrier (275). A pair of 90° off-set screws (279) secure the valve drive shaft (270) and the tip of the set screws (279) engage corresponding 90° off-set flats (280) on the valve drive shaft (270) to prevent rotation between the drive shaft (270) and the crank carrier (275). An inlet valve bearing (282) and an outlet valve beating (284) are attached to the crank carrier (275) by a pair of press pins (286) and are spaced from the crank carrier (275) by washers (288). In this manner the bearings (282,284) may spin freely about the press pins (286).

An inlet rocker arm (290) is mounted between an orifice (291) in the inlet valve support boss (264) and an orifice (not shown) in the intermediate valve support boss (268) by an inlet valve shaft (292) received within an inlet valve shaft envelope (294) of the inlet rocker arm (290) and is secured thereto against relative motion by the pin (295). Bushings (296,297) in the orifices (291,293) provide for smooth rotation of the shaft (292). An inlet valve cam (298) extends transversely from a front end of the inlet valve shaft envelope (294) with its distal end received around the bearing (282). A valve actuator (304) extends transversely from a second end of the inlet valve shaft envelope (294). An outlet valve rocker arm (305) is mounted between an orifice (306) in the outlet valve support boss (266) and an orifice in the intermediate valve support boss (268) about an outlet valve shaft (307) received in the outlet valve shaft envelope (308) and the outlet valve envelope (308) is secured against rotation relative to the outlet valve shaft (307) by the pin (309). A bushing (310) in the outlet valve support boss orifice and a bushing (not shown) in the intermediate support boss orifice provide for smooth rotation of the shaft (307). An outlet valve cam (311) at a first end of the outlet valve envelope (306) receives the bearing (284) at its distal end. At the second end of the outlet valve envelope (306) is an outlet valve actuator (313).

Figure 17:
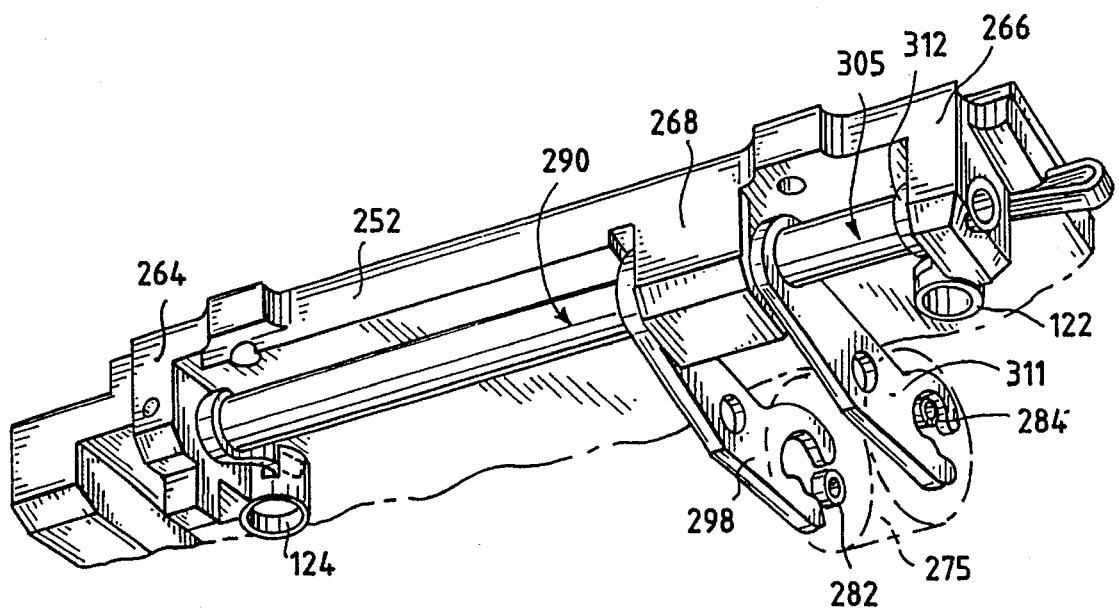
FIG. 17 is a perspective view of the inlet and outlet rocker arms of the pump driving mechanism.

FIG. 17 illustrates the crank carder (275), the valve motor shaft (270), the inlet rocker arm (290) arid the outlet rocker arm (305) in a "neutral" position with the inlet valve pincher (122) and outlet valve pincher (124) biased closed. As seen in FIG. 17, the inlet valve bearing (282) is located on an opposite end of the crank carrier (275) from the outlet valve bearing (284), and the inlet valve bearing and the outlet valve bearing are located on radii extending 180° from each other.

Figure 18A:
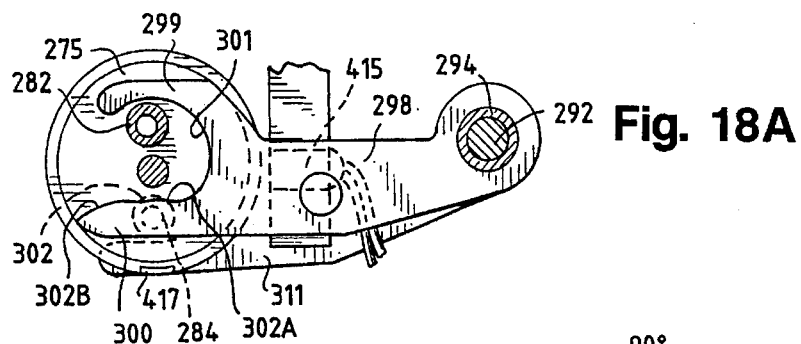
FIG. 18A–18D are left side views with respect to FIG. 17 of the inlet valve cam and the outlet valve cam in engagement with the crank carder connected to the valve motor shaft.

FIG. 18A is taken from the perspective of the left-hand side of the inlet valve cam (298) as viewed in FIG. 17. The inlet valve cam (298) includes a first leg (299) and a second leg (300) defining an arcuate surface (301) therebetween. The outlet valve cam (311) is configured identical to the inlet valve cam (298), which simplifies manufacture of the pumping mechanism. The arcuate surface (301) forms a dual cam (302) having a first cam surface (302A) and a second cam surface (302B) proximate the distal end of the first leg (300). The dual cam surface (302) is configured so that as the crank carrier (275) is rotated clockwise from the valve neutral position from the perspective of FIG. 18A, the first cam surface (302A) is engaged by the outlet valve bearing (284) causing the outlet valve cam (311) to lift the outlet pincher valve (124). The arcuate surface (301) proximate the first leg (299) is configured so that the inlet valve beating (282) kisses the arcuate surface (301) without causing movement of the inlet valve cam (298). In a like manner, when the crank carder (275) is rotated clockwise from the valve neutral position from the perspective of FIG. 18A, the second cam surface (302B) is engaged by the inlet valve bearing (282), causing the inlet valve cam (298) to lift the inlet pincher valve (122).

Referring to FIGS. 15 and 16, the plunger motor (256) is a DC electric motor attached to the plunger motor support boss (260) with the plunger drive shaft (316) received within the axially aligned holes (318,320) in the plunger motor support boss (260) and the central boss (158), respectively. Bushings (321,322) facilitate rotation of the plunger drive shaft (316) within the holes (318,320). Mounted about the plunger drive shaft (316) is a plunger cam (323) nested between the central boss (258) and the plunger motor support boss (260) and held in place by a pair of 90° offset screws and corresponding flats (not shown). The plunger cam (323) has a flag or mechanical stop (324) integrally formed between a least diameter portion (325) and a greatest diameter portion (326) of the plunger cam surface. Beginning at a "home" position with the plunger fully retracted, the DC electric plunger motor (256) oscillates approximately 194° in a first direction, thereby engaging the greatest diameter portion (326) of the plunger cam (322) with the plunger (120) to extend the plunger (120) so as to compress the pump chamber (140). The plunger motor can reverse direction and rotate the plunger cam (322) up to 200° in a second direction opposite the first direction until the flag (324) couples the optosensor (410), thereby returning the plunger to the "home position" by engaging the least diameter portion (325) of the plunger cam (322) with the plunger (120), allowing the pump chamber (140) tubing to bias the plunger (120) to its fully retracted position. Runaway is prevented by the mechanical stop (324) of the plunger cam (322) abutting the assembly frame (252) to mechanically stop rotation of oscillating plunger motor (256) in the event of a system failure.

The ambulatory infusion pump (10) uses a separate valve motor (254) and plunger motor (256) to allow for the independent control and timing of the valves and the plunger. In addition to making the fail-safe reciprocating action discussed above possible, the use of two motors allows each motor to be optimized for its own selected task. In this manner, the motors are more energy efficient than attempting to use one motor for both plunger and valve actuation. The use of two motors also allows independent control of the plunger and valves, a feature which is used to perform a number of self-test and self-compensating functions and to facilitate delivery of fluid at different rates through different pump modes employing a number of distinct plunger and valve actuation sequences, all of which will be discussed in greater detail below.

As seen in FIG. 16, inlet and outlet valve assemblies (330, 330A) include a valve pincher mount (332) received within a valve guide (334) with a valve washer (336) and a compression spring (338) axially nested therebetween. The valve guide (334), in turn, is attached to the assembly frame (252) where indicated in FIG. 16. The compression spring (338) biases the mount valve pincher (332) away from the assembly frame (252) to an extended position for occluding the inlet or outlet valve tubes (142,144). In addition, a C-spring or leaf spring (340) is received in a slot (342) of the inlet valve guide (334) and acts on the proximal end (344) of the valve pincher mount (332) to further bias the valve pincher (332) away from the assembly frame (252) to an occluding position. The leading edge of each of the inlet and outlet valve pinchers (122,124) has a small radius of 0.03 inches. This small radius minimizes the energy necessary to occlude the inlet and outlet valve tubes (142,144) while minimizing kinking of the tubing during occlusion. In addition, as most clearly seen in FIG. 10, the stops (131) at opposite ends of the leading edge of the inlet valve pincher (122) (and, though not separately illustrated, on the outlet pincher (124)), maintain a 0.04 inch gap between the pincher valve and the platen which further minimizes tube kinking while the tubes are occluded. Either of the compression spring (338) or the C-spring (340) provides sufficient bias to the valve pinchers (122,124) to occlude the inlet and outlet valves (142,144), thus providing an added margin of safety. Furthermore, this spring bias ensures that if power to the pump is cut off, the valves will return to a neutral position occluding the inlet and outlet valves (142,144) or, if either valve is in the over center position when the power is cut-off, the valve will remain open and the other valve will be biased closed.

A plunger assembly (350) includes the plunger (120) having a back (352) with a pair of bosses (354) which receive a cam follower or ball bearing (356) therebetween, the cam follower (356) being maintained in place by an eccentric (358) for calibration of the plunger position. The plunger cam (323) acts on the cam follower (356) to drive the plunger upward as the plunger cam (323) rotates in a counter-clockwise direction with reference to FIG. 19.

A pressure transducer (362) is received in a stepped hole (364) in the assembly frame (252). A transducer backing plate (366) is fastened to the assembly frame (252) by screws (368) to maintain the pressure transducer (362) in a fixed position. A transducer button (368) is also received within the stepped hole (364) and extends outwardly from the assembly frame (252) opposite of the pressure transducer (362) so that the transducer button wedge (126) can extend between the guide posts (128) into the pump cassette receptacle (84).

A gasket (370) made of a molded silicone rubber has an inlet valve pincher orifice (372), an outlet valve pincher orifice (374), a plunger orifice (376) surrounded by a raised collar (377), a transducer button orifice (278), and four registration pin orifices (380). The transducer button (368) is inserted through the pressure transducer orifice (378) so that the flange (381) is on the frame side of the gasket. The plunger (120) is inserted into the plunger orifice (376) such that the gasket sits in a slot in the frame (252) around the plunger (120). The registration pins (118) are fixedly attached to the bottom of the assembly frame (252) and are received within the registration pin orifices (380) of the gasket (370). The gasket (370) is then stretched so that the inlet and outlet valve pinchers (122,124) are received within the inlet and outlet pincher orifices (372,374) and the gasket is press fit against the frame. The gasket (370) functions as a face seal between the inner surface of the rigid housing back 22 and each component. The raised collar (377) functions to resiliently bias the plunger (120) toward the frame (252) to maintain the cam follower (356) in contact with the plunger cam (323) even if the door (50) is open or no cassette (86) is in the cassette receptacle (84).

FIGS. 18A–D illustrate actuation of the inlet and outlet valve pinchers (122,124) by the valve motor (254). As the crank carrier (275) is rotated counterclockwise with respect to FIG. 18A, the inlet valve beating (282) engages the second cam surface (302B), actuating the inlet valve (298) against the action of the spring (338) and C-spring (340) so as to open the inlet valve tube (142). Although not illustrated, with the valve carrier so rotated, the outlet valve bushing (284) kisses the arcuate surface (301) proximate the first leg (299) of the outlet valve cam (310), thereby exerting no force on the outlet valve cam (311). As the outlet valve bearing (284) disengages the first cam surface (302A), the outlet valve cam (311) is biased upwards by the force of the springs (338) and (340). However, should the outlet valve become stock in an open position contrary to the bias of the springs (338) or (340), the outlet valve bushing (284) will forcibly contact the arcuate surface (301). This may have the effect of dislodging the outlet pincher valve (124) from the non-occluding position or, more likely, it will result in an increased draw of energy on the valve motor, thereby triggering an alarm (see Section F below).

Figure 18B:
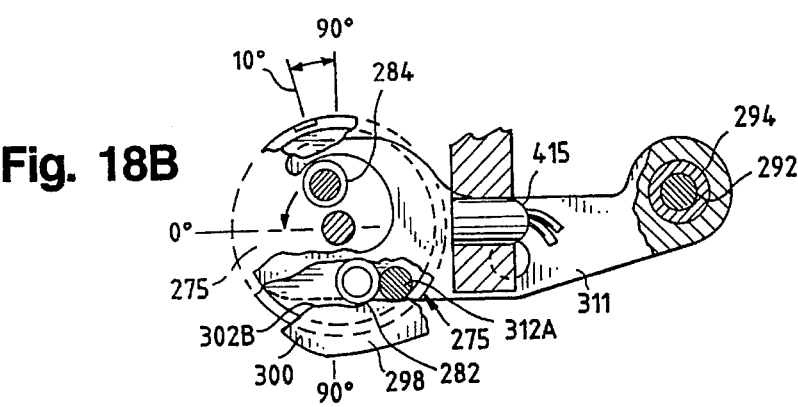
Figure 18C:
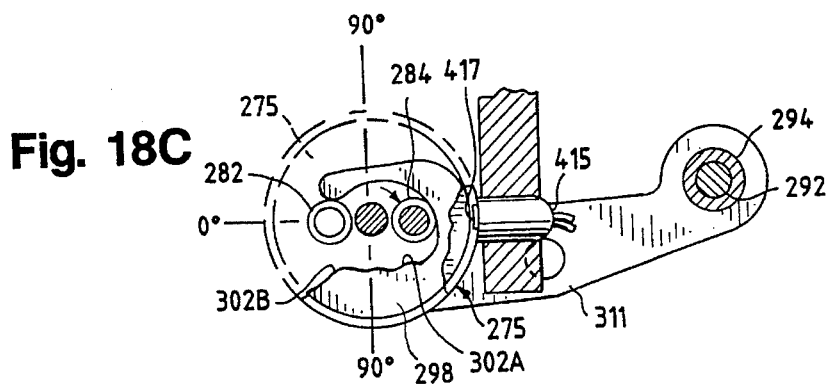
Figure 18D:
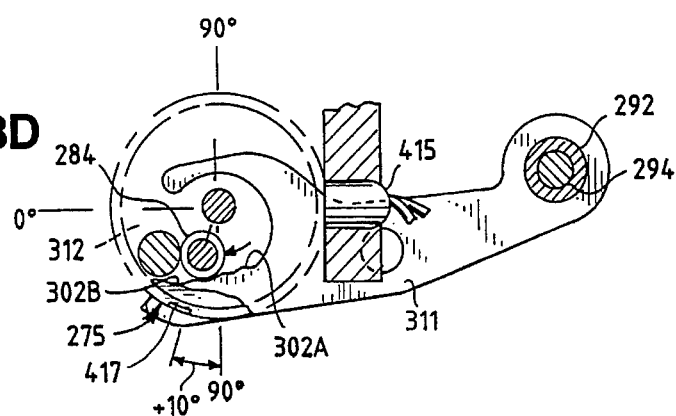

FIGS. 18B–D serve to illustrate an over center feature of the valve driving mechanism. FIG. 18C illustrates the inlet valve cam (298) in the valve neutral position. FIG. 18D illustrates that the crank carrier is rotated clockwise from the valve neutral position of FIG. 18C. The inlet valve bearing (282) kisses the arcuate surface (301) proximate the first leg (299) of the inlet valve cam (298). Concurrently, the outlet valve bushing (284) engages the first cam surface (302A), thereby actuating the outlet valve cam (311) and fully opening the outlet pincher valve (124) after 90° of rotation. The crank carrier (275) is rotatable approximately an additional 10° clockwise to an over center position illustrated in FIG. 284D, whereupon the outlet valve bushing (284) engages the stop (312). At the over center position, the outlet valve cam (311) is "locked" in position against the bias of the springs (338) and (340). The valve motor rotates the crank carrier (275) counterclockwise back to the valve neutral position illustrated in FIG. 18C. Further rotation of the crank carrier (275) 90° counterclockwise will cause the inlet valve bearing (282) to engage the second cam surface (302B), actuating the inlet valve cam. (See FIG. 18B) As with the outlet valve assembly, rotation an additional 10° will "lock" the inlet valve can (298) in an over center position. Accordingly, if power to the valve motor is cut off, three valve positions are possible: 1) crank carrier halted over center with the outlet valve open and the inlet valve closed; 2) crank carrier halted in the valve neutral position with both valves closed; or 3) the valve carrier halted in an over center position with the inlet valve opened and the outlet valve closed. Thus, at least one valve is always closed, preventing unintentional free flow. It should be noted that at high pump rates, the valve motor does not pause with the crank carrier in the valve neutral position.

E. Position Sensor/Magnetic Detent

As will be discussed below with reference to FIG. 32, the pump (10) includes an electronic control (385) which actuates the pumping assembly (250) and receives signals from a variety of sensors to monitor pump performance.

Figure 20:
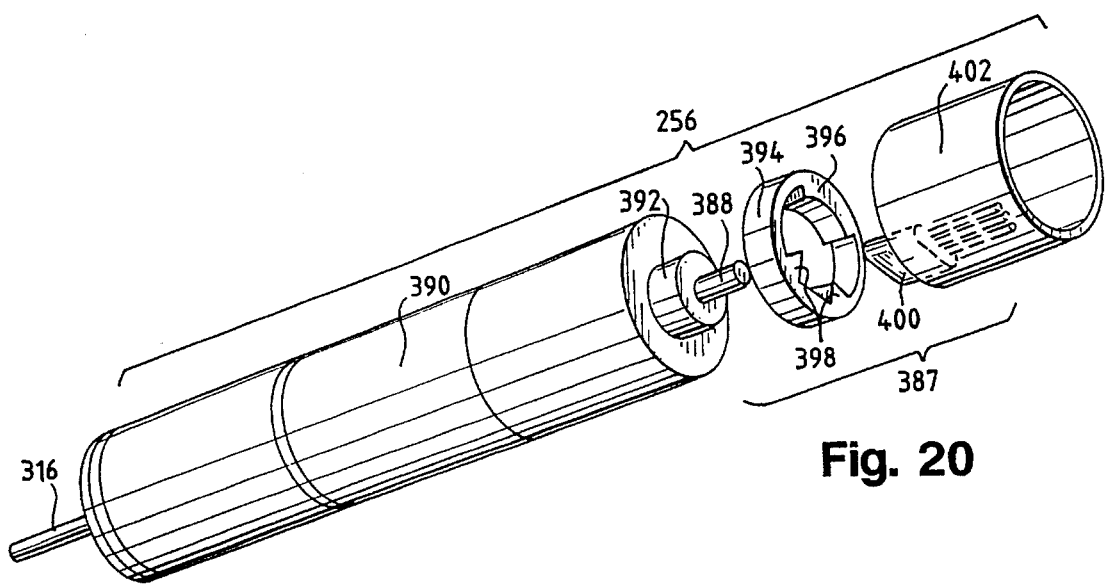
FIG. 20 is an exploded perspective view of a position encoder/magnetic detent of the plunger motor.

The plunger motor (256) is shown in an exploded perspective view in FIG. 20 to illustrate a Hall sensor/magnetic detent assembly (387) for permitting precise monitoring of the plunger position and for maintaining the plunger in a precise position when the plunger motor is not energized. A motor drive shaft (388) extends opposite the plunger drive shaft (316) from the body (390) of the plunger motor (256). Fixed to the motor drive shaft (388) for rotation with the motor drive shaft is a rotary cylindrical Neodymium-Yag magnet (392). Radially spaced about the periphery of the rotary magnet (392) is a ferrimagnetic collar (394), the ferrimagnetic collar being made of soft iron in the present embodiment. Integrally formed in an inner surface of the ferrimagnetic collar (394) is an inwardly extending flux collector (396). Located on the ferrimagnetic collar (394) opposite the flux collector (396) are a pair of spaced bosses (398) extending inwardly from an inner surface of the ferrimagnetic collar, the bosses being spaced to receive a Hall sensor (400) therebetween. A shell (402) is provided for encasing the Hall sensor/magnetic detent assembly (387). As generally understood by those skilled in the art, the Hall sensor (400) is used to sense the position of the motor drive shaft (388) so that the corresponding position of the plunger (120) can be precisely monitored. More particularly, the Hall sensor (400) sends a signal to the control (385), once each revolution of the shaft (388), so that the control (385) can track the precise location of the plunger (120).

The flux collector (396) cooperates with the magnet (392) to function as a magnetic detent. More particularly, when the motor (256) is deenergized, rotation of the motor shaft (388) will be resisted by attraction of the poles of the magnet (392) to the flux collector (396). This attraction or detent feature provides sufficient resistance to rotation of the shaft (388) that the plunger (120) can be maintained in a selected position notwithstanding the pump chamber (140) biasing the plunger (120) to retract. That is, the detent provides sufficient holding torque with the motor turned "off" during a sleep sequence to prevent back driving of the plunger. In this manner, the DC electric motor (256) functions like a stepper motor in that its shaft can be stopped at precise locations. However, the DC electric motor maintains the advantage of being significantly more energy efficient and lightweight than a stepper motor. In addition, when the shaft (388) is rotated at high speeds, the magnetic detent effect becomes "transparent" in the sense that vibration of the motor is minimized.

F. Other Sensors

As seen in FIG. 16, in addition to the Hall sensor/magnetic detent assembly (387), the plunger motor (256) includes a sensor (404) for monitoring motor current, the sensor (404) producing an electrical signal proportional to the motor current. The control (385) monitors the electrical signal to ensure a high current which indicates a jam or other abnormal condition is not present. If such an abnormal condition is present, the control (385) activates an alarm.

The valve motor (254) also includes a Hall sensor (406) for producing an electric signal with each revolution of the valve motor drive shaft which is similar to the Hall sensor/magnetic detent (287) of the plunger motor, only lacking the flux collector (297) and therefore the magnetic detent feature of the Hall sensor/magnetic detent (387) of the plunger motor (256). In addition, a valve motor sensor (408) produces an electrical signal proportional to the current drawn by the valve motor (254), which is monitored by the control (385) as discussed above with respect to the plunger motor (256).

Figure 19:
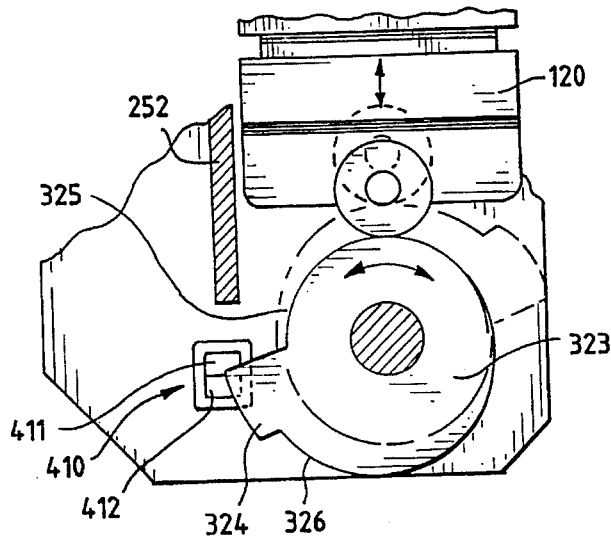
FIG. 19 is a right side view with respect to FIG. 16 of the plunger cam and plunger.

Optical position sensors are also included as part of the plunger and valve drive for the purpose, of monitoring the position of the plunger (120) and the inlet (122) and outlet (124) valves. A plunger optical sensor (410) (see FIGS. 15, 16 and 19) includes a light emitting diode (411) and a photodetector (412) (FIG. 19). With the plunger cam rotated to its "home" position as illustrated in FIG. 13, the plunger cam flag (324) causes a coupling between the light emitting diode (411) and the photodetector (412) which in turn causes the cam position sensor (410) to send an electric signal to the control (385) indicating that the plunger cam (323) is in its "home" position, corresponding to the plunger (120) being in a "retracted" position. As the plunger cam (323) actuates the plunger (120) out of the home position illustrated in FIG. 13, the light emitting diode (411) and photodetector (412) are uncoupled and the LED and photodetector can be turned off to save power. If turned off, the LED and photodetector are repowered when the control (385) determines, by virtue of signals received from the Hall sensor (400), that the plunger cam has returned to the home position.

A valve optical sensor (415) is located where indicated in FIGS. 16 and 18A–D. The flag ting (276) has a black anodized outer surface with a non-coated reflective window (417). The valve optical sensor includes an LED and a photodetector, not separately shown. When the reflective window (417) aligns with the optical sensor, the LED and the photodetector are "coupled", causing generation of an electric signal which is sent to the control (385). The reflective window (417) aligned with the valve optical sensor (415) corresponds to a "neutral" position of the valve motor crank (270), meaning that both valves are closed. When the reflective window is rotated out of alignment with the valve optical sensor, the LED and photodetector are uncoupled and the valve optical sensor is turned off to conserve power. The position of the window (417) is adjusted during calibration of the pump to precisely correspond to the neutral position by loosening of the set screw (278) and rotation of the flag ring (276) relative to the crank carrier (275).

The plunger optical sensor (410) and the valve optical sensor (415) are used in conjunction with the plunger motor Hall sensor (400) and the valve motor Hall sensor (406) to precisely monitor the location of the plunger and the inlet and outer valves relative to their home and neutral positions, respectively. More particularly, the optical sensors are used by the control (385) to define the home and neutral position of the plunger and valve. The Hall sensor provides a much finer resolution for locating the plunger and valve relative to the home and neutral positions. For example, with respect to the plunger, twenty-five revolutions of the motor are required to fully extend the plunger from its home position. Each revolution of the motor results in one signal from the plunger motor Hall sensor (400), therefore counting of the signals from the Hall sensor by the control (385) permits precise location of the plunger. Thus, the plunger and valve optical sensors (410,415) are used by the control (385) to verify the accuracy of the position determined based upon the Hall sensors, to calibrate position of the plunger and valves, by being turned on and off by the control (385), to conserve energy.

Figure 21:
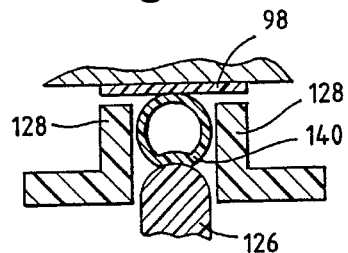
FIG. 21 is a sectional view of the transducer button wedge beating upon the pump chamber.

The pressure transducer (362) is operatively linked to the pump chamber (140) by the button wedge (126), as best seen in FIGS. 4 and 16. The pump chamber (140) is received between the guide posts (128) which ensures that the arcuate leading edge (127) of the button wedge (126) compresses the pump chamber against the platen (98) in the manner illustrated in FIG. 21, thereby minimizing the propagation of "noise" signals which would otherwise effect the accuracy of the transducer (362). Pressure fluctuations within the pump chamber result in a displacement of the button wedge (126) which is detected by the transducer (362). The transducer (362) produces an electric signal representative of the pressure in the pump chamber (140) which is transmitted to the control (385). The control (385) monitors pressure in the pump chamber to check for insufficient pump chamber refill, valve leakage or downstream occlusion, as will be discussed in greater detail in Section N2 below.

A cassette door sensor (420) is illustrated in FIG. 3. It is a magnetic proximity sensor which monitors when the cassette door (50) is properly engaged to the rigid housing back (22). More particularly, the door sensor (420) sends an electric signal to the control (385) when latch (56) is a "closed" position. When such a signal is received, the control (385) permits pump operation.

A front cover sensor (422) (see FIG. 2) is a magnetic proximity sensor which detects when the front cover (24) is slid down to uncover the programmer display (28) and keyboard (30). When the control panel (26) is opened a sufficient distance, the front cover sensor will send an electric signal to control (385), causing the control (385) to energize a programming display (228). When the front cover (24) is closed and the electric signal is no longer received, the control (385) deactivates the programmer display (28) to conserve power.

The ultrasonic air detector (130) (see FIG. 4) is provided for ensuring that excessive air is not delivered with the liquid medication to a patient. The ultrasonic air detector (130) includes a conventional piezoelectric ultrasonic transmitter and receiver spaced apart on both sides of the inlet valve robe (142). The transmitter and receiver are spaced slightly less than the outer diameter of the inlet valve tube (142) to assure that the inlet valve robe (142) fits snugly therebetween. The finger (423) extends from the door (50) and received between the transmitter and receiver (130) to force the inlet valve tube (142) between the transmitter and receiver (13) upon closing the door (50) and to secure the inlet valve tube (142) therebetween. The transmitter produces an ultrasonic signal that is transmitted through an inlet valve tube (142) to the receiver. Liquid present in the inlet valve tube (142) between the transmitter and the receiver conveys the ultrasonic signal much more efficiently than does an air bubble. The receiver produces and transmits to the control (385) an electric signal in response, to the level of the ultrasonic signal it receives, the amplitude of the electronic signal indicating whether an air bubble or liquid is present in the inlet valve robe (142) between the transmitter and the receiver. During refill of the pump chamber, an ultrasonic signal is produced once each motor revolution. Only if the signal received by the control (385) indicates that an unacceptable level of air is present for a select number of consecutive refill revolutions will an alarm indicating air in the pump chamber be triggered. The air detect routine of the control (385) is discussed in further detail in Sec. N2.

G. Soft Pump Case

Figure 22:
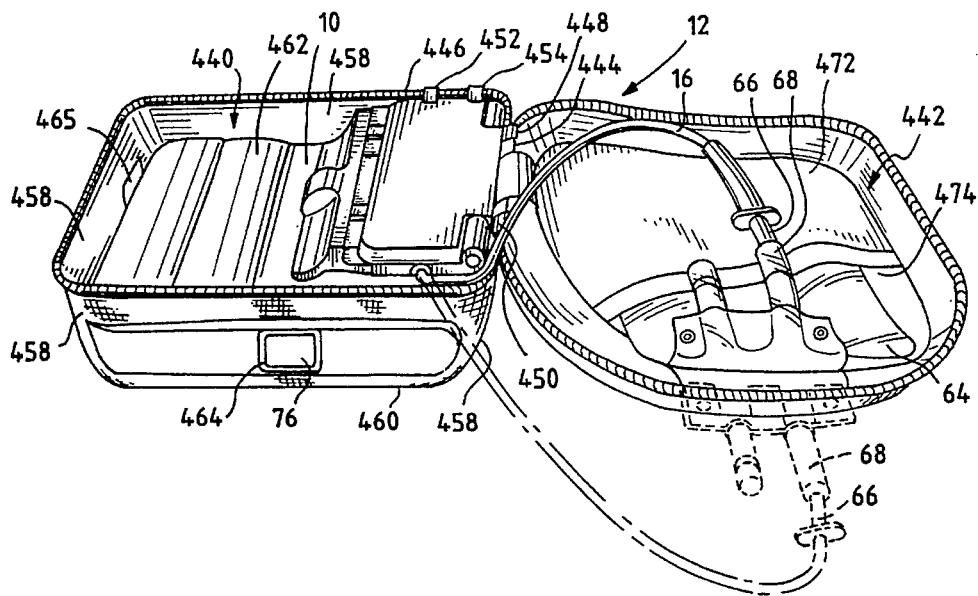
FIG. 22 is a perspective view of the ambulatory infusion pump received in a soft pump case with the case open.
Figure 23:
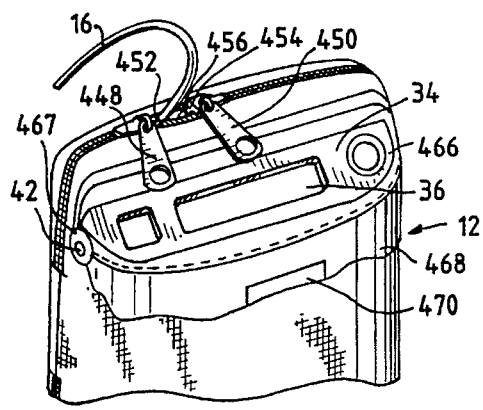
FIG. 23 is a perspective view of the ambulatory infusion pump mounted in the soft pump case with the patient display exposed.

The soft pump case (12) is shown in detail in FIGS. 22 . 24. The soft pump case (12) is made of fabric such as a waterproof nylon and includes a pump receiving chamber (440) and a solution bag receiving chamber (442) joined by an integral hinge (444). The pump receiving chamber (440) and the solution bag receiving chamber (442) are joinable in an abutting and overlying relationship by a zipper (446). The zipper (446) includes a first slider (448) and a second slider (450) and first and second stops (452,454). As illustrated in FIG. 23, with the first and second sliders (448,450) positioned with the zipper teeth engaged, they come into abutment with the first and second stops (452,454) to define a gap (456) through which the IV tube (16) can extend from the soft pump case (12). The second slider (450) causes approximately three-quarters of the zipper teeth to become engaged and disengaged and the first slider (448) causes less than a quarter of the zipper teeth to become engaged and disengaged.

The pump receiving chamber (440) includes four side walls (458) and a bottom wall (460) with the zipper teeth at the distal end of the side walls (458). An elastic retention strap (462) extends across the bottom wall (460) for securing the ambulatory infusion pump (10) within the pump receiving chamber (440). Alternatively, a hook and loop strap could replace the elastic retention strap (462). A variety of holes are provided in the side walls (458) of the pump receiving chamber to allow for access to the pump controls. For example, the hole (464) provides access to the on/off switch (76), a hole (465) provides access to the IR window (70) and a grommet (467) provides access to the remote bolus switch contact (42) (see FIG. 23). A clear plastic membrane preferably covers the hole (464) to protect the ambulatory infusion pump (10) from dirt and moisture. FIG. 23 illustrates a panel (466) which provides for access to the user control panel (32). In one embodiment, the panel (466) is covered with a clear plastic membrane to allow for observation of the patient display (36) as well as access to the control buttons on the beveled front surface (34) of the pump 10. A cover (468) can selectively cover or expose the panel (466) and is preferably secured to the exterior of the pump receiving chamber (440) by a hook and loop connector (470) such as Velcro®.

The solution bag chamber (442) includes a partition (472) defining a pocket (474) for receiving the solution bag (64). A pair of straps (74) are on the exterior of the solution bag chamber (442) for fastening the soft pump case to an upright support such as a patient's belt (see FIG. 1).

Figure 24:
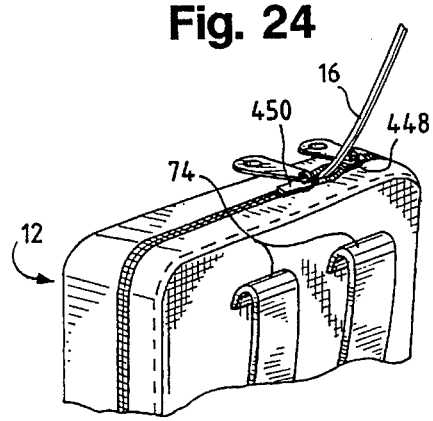
FIG. 24 is a perspective view of the rear of the soft pump case.

As illustrated in FIG. 22, with the solution bag (64) received in the pocket (474), the solution bag outlet orifice (68), including the spike (66), can be folded over the solution bag (64) and the partition (472). The solution bag chamber (442) can then be folded over the pump receiving chamber (440) in a book-like fashion so that the first and second sliders (448,450) can engage the teeth of the zipper (446) to close the soft pump case (12). With the soft pump case so closed, the ambulatory infusion pump (10) can be attached to a patient by the belt loops (74) (see FIG. 24) for convenient travel with the patient. The solution bag is located between the rigid front and back housings (20,22) of the ambulatory infusion pump (10) and a patient's body, thereby protecting the solution bag (64) from damage. In addition, the fluid within the solution bag (64) is maintained at or near the patient's body temperature. This improves pump accuracy because changes in viscosity resulting from changes in liquid temperature are minimized. Furthermore, the solution bag provides padding between the patient and the pump, enhancing patient comfort.

H. Pump Displays and Delivery Profiles

Figure 25:
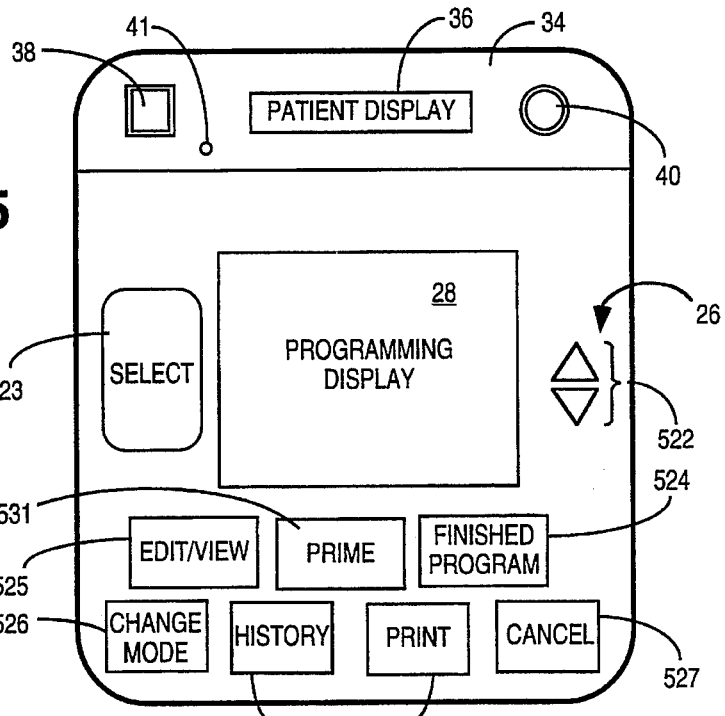
FIG. 25 is a plan view of the control panel and beveled front surface of the ambulatory infusion pump.
Figure 26:
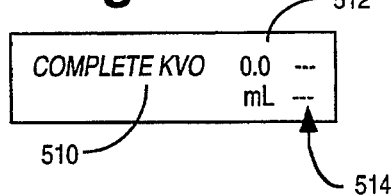
FIG. 26 is a plan view of the patient display.

The control panel (26) and beveled front surface (34) are shown in greater detail in FIG. 25. A sample patient display (36) is illustrated in FIG. 26. The patient display shows user information through fixed segments or icons (510). For example, in FIG. 26 the "COMPLETE KVO" icon means that the current infusion has ended and the pump is now running at the Keep Vein Open (KVO) rate. Volume remaining in a medication supply is shown at (512). Lines (514) are sequentially illuminated to provide a user immediate confirmation that the pump is pumping.

The programming display (28) is used for data entry and displaying status information to a clinician. The three major screens which the clinician will see are the select delivery mode (FIG. 27), set up (FIG. 28) and status (FIG. 29).

Figure 27:
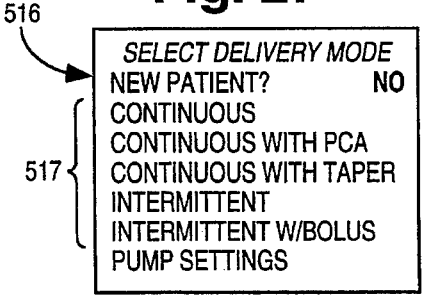
FIG. 27 is a plan view of the program main display with a "select delivery" mode screen.

A sample select delivery mode screen (516) is illustrated in FIG. 27. Each of the five delivery profiles (517), which are discussed in this section below, are listed: 1) continuous; 2) continuous with patent controlled analgesia (PCA); 3) continuous with taper; 4) intermittent; and 5) intermittent with bolus.

Figure 28:
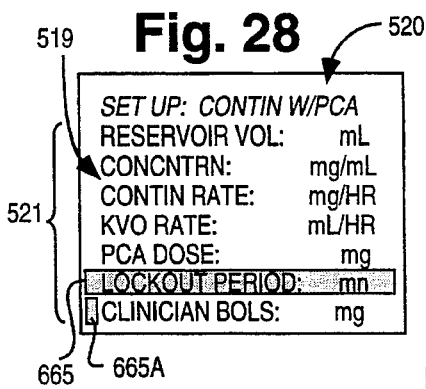
FIG. 28 is a plan view of the programming display with a sample "setup" screen.

A sample setup screen (519) is illustrated in FIG. 28. A distinct setup screen is displayed for each delivery profile (517). An icon (520) indicates the appropriate delivery profile. Here, the setup screen is for continuous infusion with a PCA. Using the keyboard (30), a clinician can enter values for each of the input options (521), as discussed in greater detail below. For example, the reservoir volume, medication concentration, the rate at which the drug is to be infused based upon the concentration rate, the PCA dose, and the lockout period and an authorized clinician bolus can all be entered.

Figure 29:
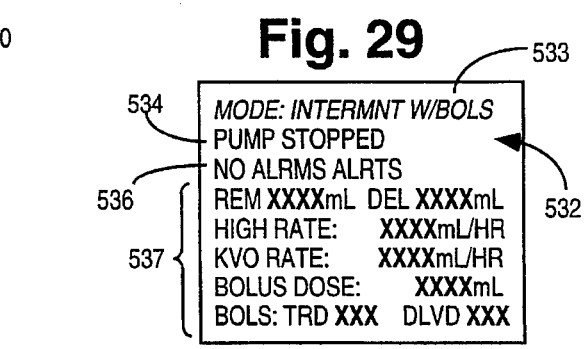
FIG. 29 is a plan view of the programming display with a sample "mode" screen.

A sample programming display screen for the mode status (532) is illustrated in FIG. 29. An icon (533) illustrates the selected pumping mode. There the icon (533) stands for intermittent administration with bolus. Current pump operating status is shown at (534). The status of any alarms or alerts is shown at (536). The volume of solution remaining, volume of solution delivered, the dose rate, the keep vein open (KVO) rate, the bolus dose and the number of bolus doses tried and delivered are displayed at (537). It should be understood that the particular parameters displayed in the setup and status screen vary with the pump mode which is currently selected.

FIGS. 37A–E illustrate the five delivery profiles. Particularly, FIG. 37 A illustrates the "continuous" flow profile. A continuous flow rate entered at the setup screen is administered for a time selected at the setup screen. Following the selected continuous flow, the pump delivers the KVO rate until the infusion ends.

Figure 37A:
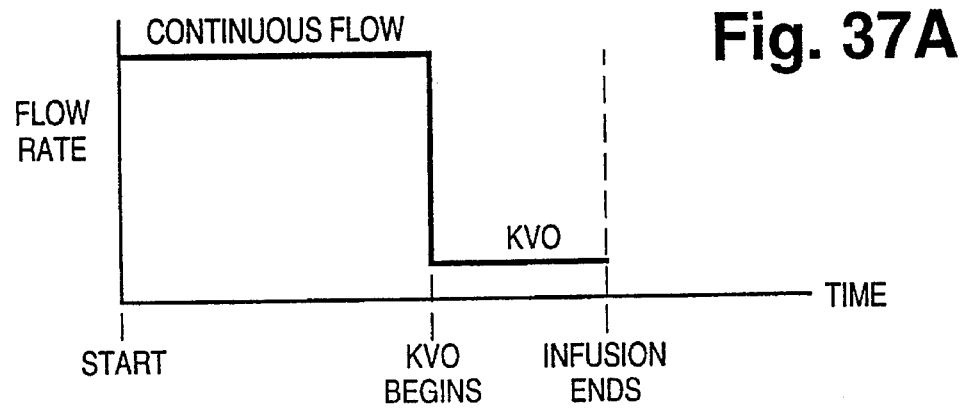
FIGS. 37A–E illustrate the five pump delivery profiles.
Figure 37B:
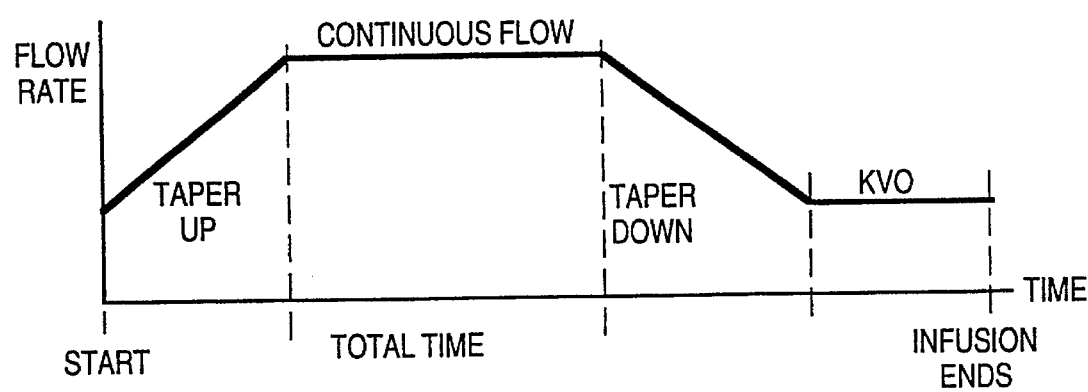

FIG. 37B illustrates the "continuous" flow with taper profile. The setup screen requires entry of the reservoir volume, total time of delivery, the taper up time, the taper down time, and the continuous rate of infusion. The monitor microprocessor calculates the taper up and taper down rates as follows. First, the continuous flow ram established between the taper up and taper down operations is calculated. The difference between the continuous flow rate and the KVO rate is divided by the number of minutes in the taper operation to obtain an amount that the rate will change each minute. For example, if the continuous flow rate is 140 ml/hr, the KVO rate is 20 ml/hr arid the taper rate is sixty minutes, then the rate will change by (140–20)/60 or two ml/hr for each minute. For taper up operation, the first minute the pump will deliver 22 ml/hr. At the end of the first minute, the pump will switch to a rate of 24 ml/hr., et cetera. This minute by minute rate stair step will continue until sixty minutes has elapsed and the continuous flow rate of 140 ml/hr. has been obtained. In a similar manner, the rate changes each minute to stair step down from the steady state flow rate to the KVO rate over the taper down time period. During each minute the rate is delivered in the manner normal for that rate within the pump. That is, one of flow modes 1–5, which corresponds to the required flow rate (see Section N below), is called by the main control routine.

Figure 37C:
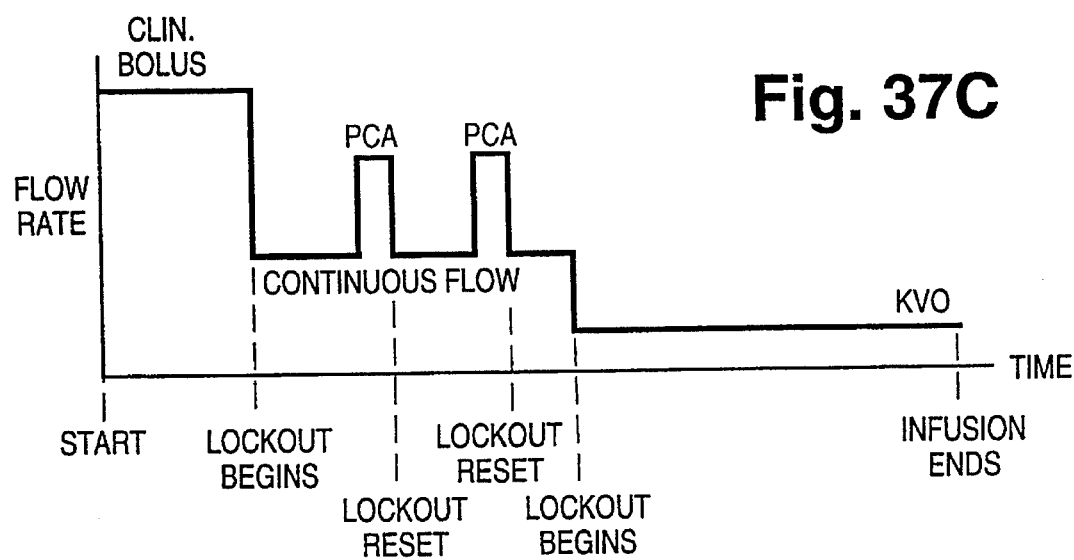

FIG. 37C illustrates the "continuous flow with PCA". At the setup screen, the user enters reservoir volume, concentration units, concentration rate, PCA dose, lockout period and clinician bolus. As seen in FIG. 37C, the clinician bolus is administered. Thereafter, a continuous flow is administered in accordance with the selected rate. During continuous flow, the patient may administer PCA dose through either the remote PCA button (44) or the PCA button (40) on the patient panel. Following administration of the PCA, the flow rate returns to the continuous flow rate and the lockout is reset. The patient is again prevented from administering PCA until the conclusion of the lockout period. The clinician bolus, continuous flow and PCA rates are delivered in accordance with the pump mode dictated by the required rate of flow. At the conclusion of the continuous flow period, delivery returns to the KVO rate.

Figure 37D:
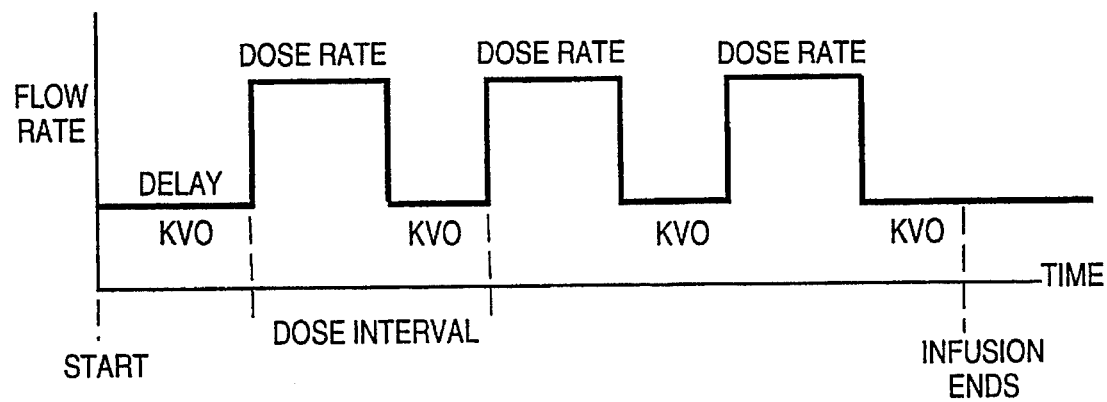

FIG. 37D illustrates the "intermittent delivery" profile. The setup screen requires entry of the reservoir volume, the dose rate, the time at dose rate, the KVO rate, the dose interval, the delay before start of the first dose administration and the start time. Between dose rates, the pump returns to the select KVO rate.

Figure 37E:
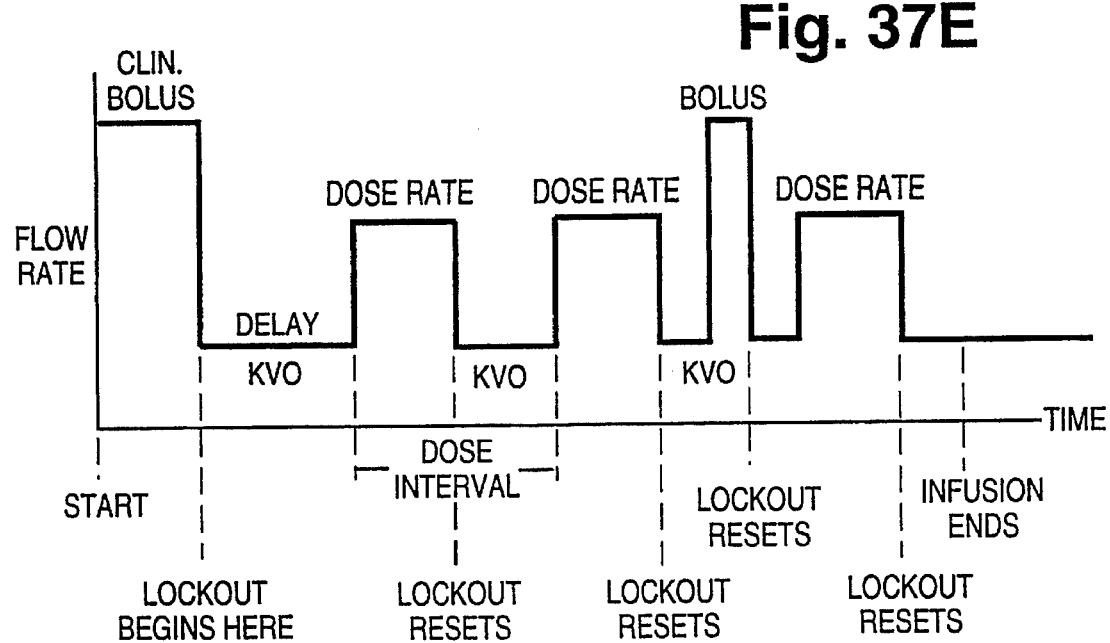

FIG. 37E illustrates the "intermittent with bolus" delivery profile. The intermittent with bolus delivery profile requires entry of the reservoir volume, the dose rate, the time at dose rate, the KVO rate, the dose interval, the allowed bolus dose, the lockout period, the delay period and, if desired, the clinician bolus. As illustrated in FIG. 37E, following the clinician bolus, the pump delivers at a KVO rate and a lockout period begins. At the conclusion of the lockout period, which can be of variable length, including zero, a bolus may be administered. The dose rate is administered after a set interval, following which the lockout period is again reset and a delivery is conducted at the KVO rate. Once the lockout period has again elapsed, a bolus dose may be again administered.

I. Programmer Controls

Figure 30:
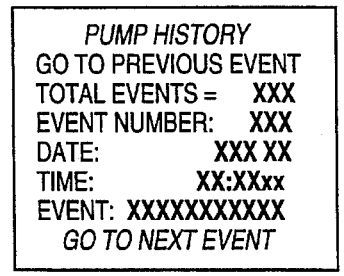
FIG. 30 is a plan view of the programming display with a sample "pump history" screen.

The keyboard (30) includes up/down buttons (522) which are used for scrolling between various delivery modes in the select delivery mode screen (516) illustrated in FIG. 27, scrolling between different input option (521) of a set-up screen (519) illustrated in FIG. 2 and for scrolling through values for each of the input option (521). A select key (523) allows selection of a delivery mode (517) scrolled to using the up and down keys (522), selection of an input option (521) for entry of a value or to deselect and enter a given value scrolled to using the up down keys (522) for a given input option (521). The finished program key (524) is used to enter a completed set-up screen (520) after entry of values for each selected input option. The edit/view key (525) allows a user to go from a mode status screen (532) of FIG. 29 to the setup screen (520) illustrated in FIG. 28. A Change Mode button (526) enables a user to go from the mode status screen (532) to the select delivery mode screen (516) of FIG. 27. The cancel key (527) cancels editing of a set-up screen (520) for a selected delivery mode and returns the programming display (28) to the last mode status screen. The history button (529) allows the clinician to view the history while the pump is in the standby state. A sample pump history screen (539) is contained in FIG. 30. The pump history displays such information as the total number of pumping events currently in the history log, an event number indicating what pump event is currently being viewed, date and time fields to indicate the date and time of the occurrence of the currently viewed event, and a description of the currently viewed event. The print button (530) can be actuated only when the pump is in the standby stage. The entire pump history can be printed by pressing the "print" button (530) once. Pushing the "print" button twice will cancel the print. The prime button (531) can be pressed following loading of the pump cassette into the pump for priming the pump. Pressing the prime button causes pumping of approximately 3.0 ml of fluid through the pump chamber.

J. Pumping

Operation of the plunger and valves to pump fluid through the pump chamber/valve assembly is best understood with reference to FIGS. 31 A–D. Each of FIGS. 31 A–D includes the pump platen (98); the pump/valve assembly (132), consisting of the pump chamber (140) and the inlet and outlet valve tubes (142), (144); the inlet valve pincher (122); the outlet valve pincher (124); and the plunger (120). As discussed in Sections N2–6, combinations of movement of the plunger (120) and inlet and outlet valves (122,124), as illustrated in FIGS. 31A–D, provide a great degree of flexibility in delivery rates (0.1 ml/hr–390ml/hr) and delivery profiles.

Figure 31A:
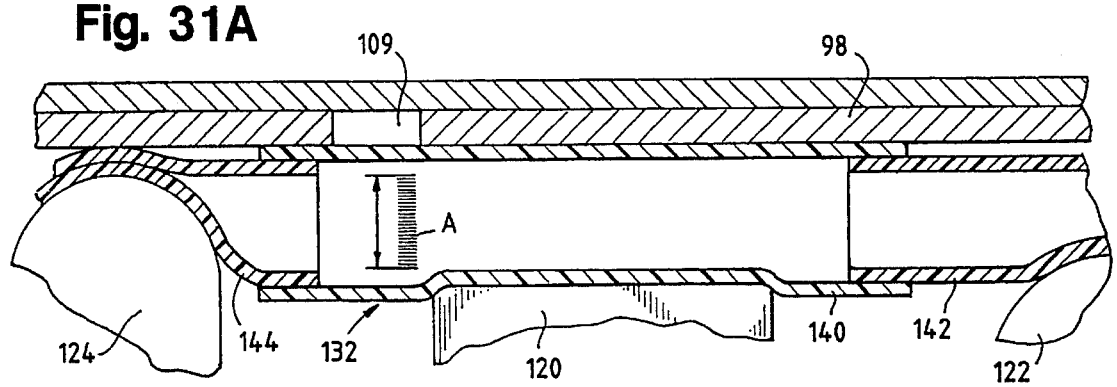
FIGS. 31A–D are sectional views illustrating the pumping action of the pump valves and plunger on the pump chamber/valve assembly.

FIG. 31A illustrates the pump chamber/valve assembly in a refill position with the outlet pincher valve (124) occluding the outlet valve to (144) and the inlet valve (122) open. The plunger (120) is in a fully retracted position, or position "–1". While fully retracted, the plunger (120) partially compresses the pump chamber (140). A scale "A" is included in FIG. 31A to represent 26 incremental advancements of the plunger (120), each advancement resulting from a revolution of the plunger motor (256).

Figure 31B:
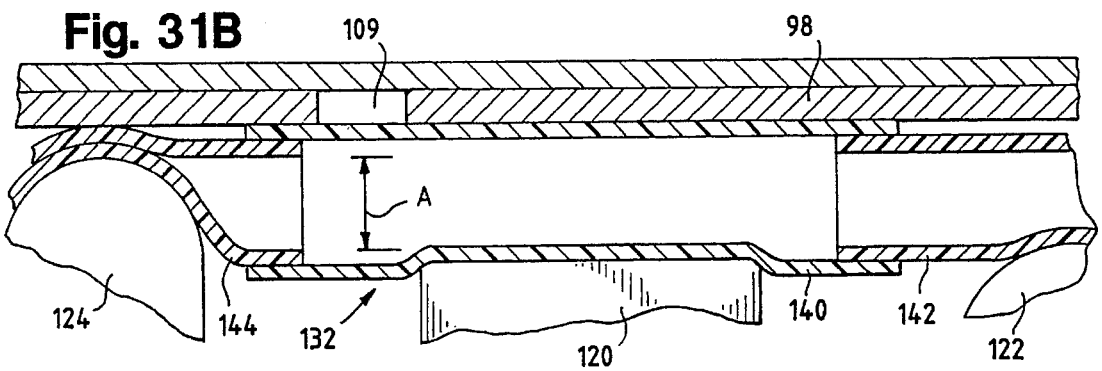

FIG. 31B illustrates the plunger advance one increment to position "0". Advancement of the plunger between the positions illustrated in FIG. 31A and FIG. 31B is known as a compensation step which is used to ensure that at position "0" the pump chamber is filled with a precise select amount of fluid.

Figure 31C:
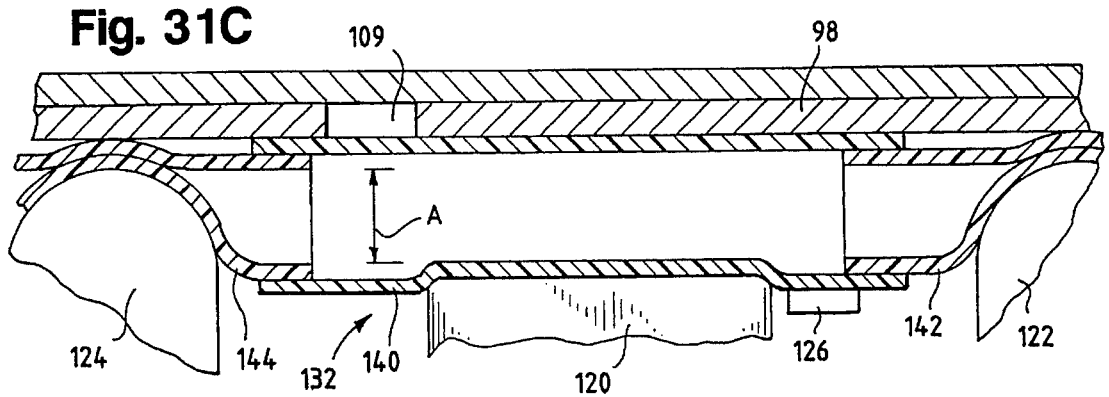

FIG. 31C illustrates a position of the valves and the plunger during a fill and valve leak test sequence. In this configuration, both the inlet and outlet pincher valves (122), (124) are extended to occlude the inlet and outlet valve tubes (142), (144) and the plunger (120) is advanced three motor revolutions so that pressure within the pump chamber can be measured by the transducer button wedge (126). The fill and valve leak test is described in greater detail in Section N.7.

Figure 31D:
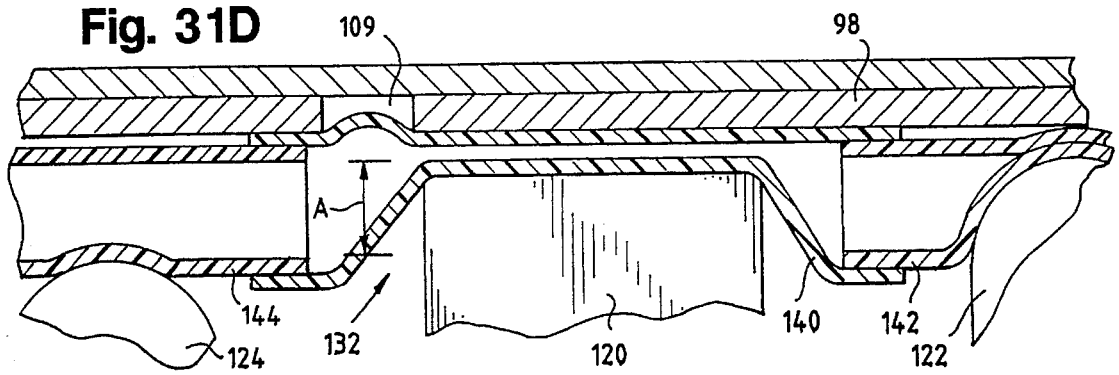

FIG. 31D illustrates the discharge of the pump chamber (140) with the outlet pincher valve (124) open and the inlet pincher valve (122) closed. In FIG. 31D the plunger (120) is illustrated at position "25", extended 25 increments or motor revolutions from the "0" or home position. With the plunger (120) fully extended, the pump chamber (140) is not fully compressed. As also viewed in FIG. 31D the pump chamber in FIG. 31D expands somewhat into the lengthwise hole (109) in the platen (98) so as to assure a more consistent pump discharge volume.

K. Pump Electronics

Figure 32:
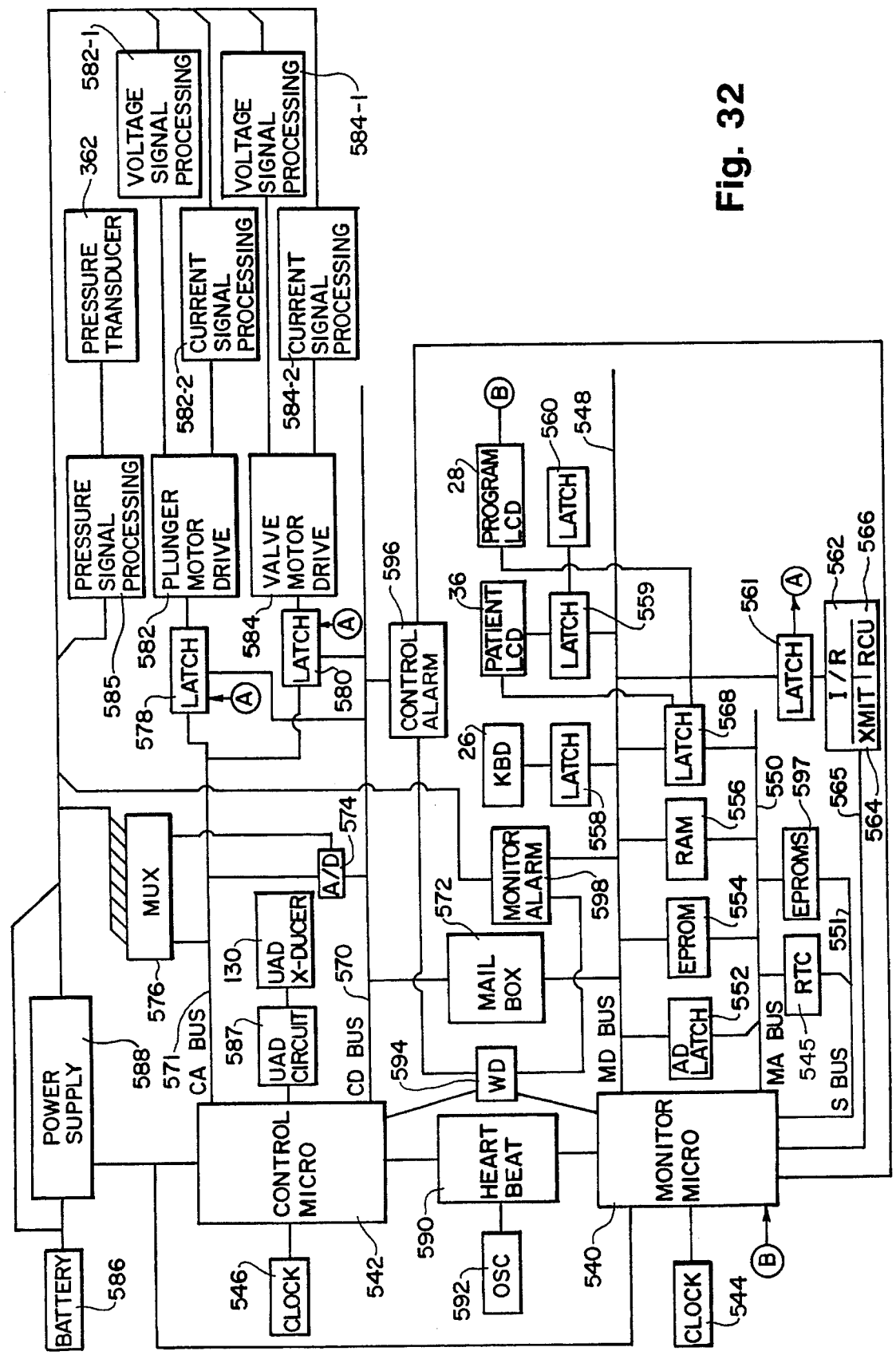
FIG. 32 is a block diagram of an electrical circuit for the ambulatory infusion pump.

With reference to FIG. 32, a block diagram illustrates an electrical circuit for the pump (10) of FIG. 1.

The pump incorporates a dual microprocessor design. The use of two microprocessors provides a great deal of design flexibility in structuring two different software packets to check and balance critical functions, and splits the work assignments on non-critical functions. The two processors have segmented functions, and different software, and are not running the same software in parallel. Their clocks are run at different frequencies to avoid errors related to single time base calculations. Critical functions, such as cam position timing signifying end of stroke, are predicted and checked by two different algorithms and software routines. The results must match, and serial communication must occur appropriately between the microprocessors to continue operation. Each microprocessor can stop the motors and sound an alarm if communications cease, are in error, or a fault condition is detected.

The two microprocessors comprise a monitor microprocessor (540) and a control microprocessor (542). Both microprocessors (540) and (542) may comprise, for example, type 87C528 single-chip eight bit microcontrollers. The monitor microprocessor (540) is connected to a clock circuit (544) operating at approximately 14.7 KHz. The control microprocessor (542) is connected to a clock circuit (546) operating at approximately 3.6 KHz.

The monitor microprocessor drives a monitor data bus (548), labeled "MD BUS", and a monitor address bus (550), labeled "MA BUS". An address decoder latch (552) connected to the MD BUS (548) develops additional addressing signals on the MA BUS (550). Memory circuits in the form of an EPROM (554) and RAM (556) are connected to both monitor buses (548) and (550).

A real time clock circuit (545) is connected to the MA BUS (550) and to the monitor microprocessor (540) via a serial bus (551) labeled S BUS and EEPROM circuits (597) are connected between the MA BUS (550) and the S BUS (551).

Four latch circuits (558), (559), (560) and (561) are connected to the MD BUS (548). The first latch circuit (558) may be a type 74HC541 latch circuit and is connected to the pump keyboard (26). The second latch circuit (559) may be a type 74H273 latch circuit connected to the patient LCD (36). The third latch circuit (560) may be a type 74HC541 latch circuit connected to the program LCD (28). The LCD (28) provides an LCD ready signal to the monitor microprocessor (540) via a node B. The fourth latch circuit (561) is connected to an infrared circuit (562). The infrared circuit (562) includes a transmit circuit (564) and receive circuit (566). The transmit circuit (564) includes an LED and conventional drive circuit for transmitting a carrier signal received on a line (565) from the monitor microprocessor (540) for remote communications. The receive circuit (566) receives infrared signals.

A further latch circuit (568) is connected to the MA BUS (550) for providing enable signals to the patient LCD (36) and program LCD (28).

The control microprocessor (542) drives a control data bus (570), labeled CD BUS, and a control address bus (571), labeled CA BUS. Communications between the control microprocessor (542) and monitor microprocessor (540) are implemented through a mailbox circuit (572) connected to the CD BUS (570) and MD BUS (548). The mailbox circuit (572) may comprise, for example, a type 74HC662 integrated circuit chip and associated logic circuits for implementing communication. Particularly, one of the microprocessors can send a message to the other microprocessor by sending the appropriate message to the mailbox circuit (572), where it will subsequently be read by the other of the microprocessors.

A conventional analog to digital (A/D) converter, such as a type MAX153 circuit, (574) is connected to the CD BUS (570) and CA BUS (571). The A/D converter (574) is connected to an analog multiplexer (576) such as a type 74HC4051 multiplexer circuit which is also connected to the CA BUS (571). The multiplexer (576) is connected to I/O devices as discussed below.

Additional latch circuits (578) and (580) are connected to the CD BUS (570) and CA BUS (571). The latch circuit (578) is connected to a plunger motor drive circuit (582). The latch circuit (580) is connected to the valve motor drive circuit (584). The latch circuits (578) and (580) may comprise, for example, type 74HC564 integrated circuits. The latch circuits (578) and (580) are also connected to the monitor latch circuit (561) for receiving an enable signal from the monitor microprocessor (540), as discussed below.

Each of the plunger motor drive circuit (582) and valve motor drive circuit (584) includes a conventional pulse width modulation (PWM) generator circuit for converting digital signals to a suitable pulse width modulated signal for driving the respective plunger motor (256) and valve motor (254), see FIG. 15. Particularly, the digital signal represents a duty cycle of motor input voltage on a zero to five volt scale. The operating frequency is approximately 68 KHz. Each PWM generator circuit in turn drives an H-bridge circuit for controlling voltage to the plunger motor (256) and valve motor (254). A voltage signal processing circuit (582-1) is connected to the plunger motor drive circuit (582) for detecting plunger motor voltage. A current signal processing circuit (582-2) is also connected to the plunger motor drive circuit (582) for detecting current drawn by the plunger motor (256). Similarly, a voltage signal processing circuit (584-1) is connected to the valve motor drive circuit (584) for detecting valve motor voltage. A current signal processing circuit (584-2) is also connected to the valve motor drive circuit (584) for detecting current drawn by the valve motor (254). The processing circuits (582-1,582-2, 584-1 and 584-2) condition the detected signals which are input to the control microprocessor (542) via the multiplexer (576).

The pressure transducer (362), see FIG. 16, is connected via a pressure signal processing circuit (585) to the multiplexer (576) for providing input of sensed pressure. The ultrasonic air transducer (130) is connected via a processing circuit (587) to the control microprocessor (542).

Power for the pump (10) is provided by a 9V battery (586) connected to a power supply circuit (588). The power supply circuit (558) includes suitable voltage regulator circuits for maintaining desired level of power to the control microprocessor (542) and monitor microprocessor (540) and other related circuits, as is well known. The battery (586) and power supply circuit (588) are also connected to the multiplexer (576) for feedback.

Because the pump (10) is powered solely by a battery (586), it is important that energy management schemes be used, as discussed above. In accordance with the invention, the microprocessors (540) and (542) include an idle mode and a power-down mode. In the idle mode, the processor puts itself to sleep while all of the on-chip peripherals stay active. Instruction to invoke the idle mode is the last instruction executed in the normal operating mode before the idle mode is activated. In the power-down mode, the oscillator is stopped and the instruction to invoke power-down is the last instruction executed. Each mode is terminated by an external interrupt received from a heartbeat circuit (590) connected to an oscillator (592). The processors (540) and (542) also wake themselves up from the idle mode by using internal timer interrupts. The heartbeat circuit (590) is configured to provide a pulse or heartbeat signal every 7.8125 msec. Upon receiving the heartbeat signal, each of the microprocessors (540) and (542) returns to the normal operating mode.

A watchdog circuit (594) is connected to each of the microprocessors (540) and (542). The watchdog circuit (594), as described below, operates with a sequence that verifies that the monitor microprocessor (540) produces a "monitor OK" pulse and subsequently the control microprocessor (542) produces a "control OK" pulse, then followed by a "monitor OK" pulse, etc., and that these pulses are at the correct time intervals.

The watchdog circuit (594) is also connected to each of a control alarm (596) and monitor alarm (598). The control alarm (596) is connected to the CD BUS (570). The monitor alarm (598) is connected to the MD BUS (548). The control alarm (596) provides a control alarm feedback signal to the monitor microprocessor (540). The monitor alarm (598) provides a monitor alarm feedback to the control microprocessor (542) via the multiplexer (576).

Figure 33:
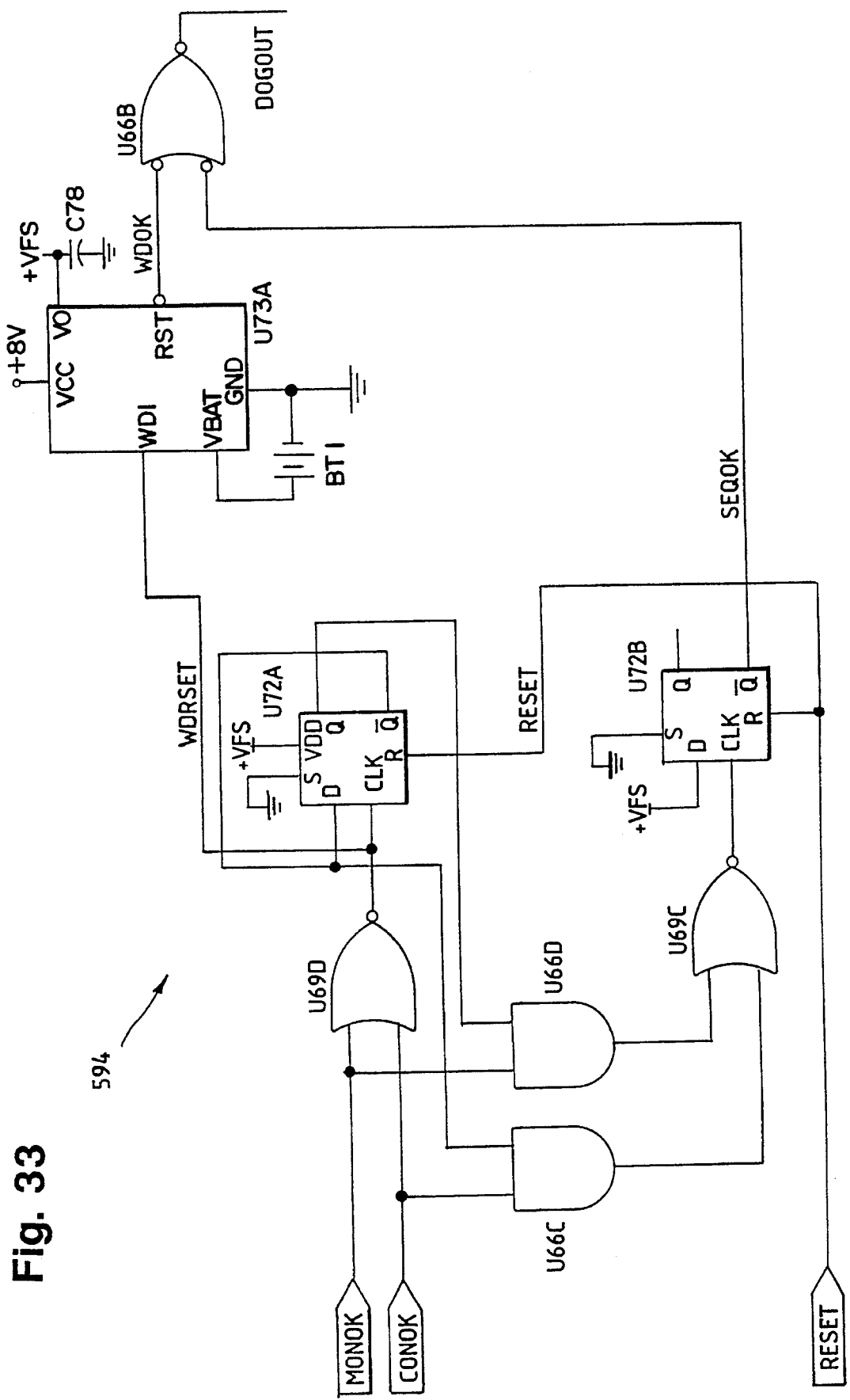
FIG. 33 is an electrical schematic for a watchdog circuit of the ambulatory infusion pump.

With reference to FIG. 33, an electrical schematic for the watchdog circuit (594) is illustrated. The watchdog circuit (594) receives a monitor watchdog reset, or OK signal, labeled MONOK from the monitor microprocessor (540), a control watchdog reset, or OK signal from the control microprocessor (542), labeled CONOK, and a reset signal from the power supply (588). Each of the CONOK and MONOK signals are connected to inputs of a negative OR (NOR) gate U69D. The MONOK signal is also supplied to one input of an AND gate U66D. The CONOK signal is also applied to one input of an AND gate U66C. The output of the NOR gate U69D is the clock input of a flipflop U72A. The inverted output of the flipflop U72A is fed back to its data input as well as the second input of the AND gate U66C. The non-inverted output of the flipflop U72A comprises the second input of the AND gate U66D. The output of the AND gates U66C and U66D comprise inputs to a NOR gate U69C, the output of which is connected to the clock input of a flipflop U72B. The data input of the flipflop U72B is connected to a plus voltage failsafe input. The inverted output of the flipflop U72B comprises a sequence OK signal coupled to an inverted input of an AND gate U66B.

The watchdog circuit 594 also includes a timer circuit U73A in the form of a monostable multivibrator, such as a type MAX 690A integrated circuit. The timer U73A, at a WDI input, receives a watchdog reset signal from the output of the NOR gate U69D. An inverted RST output of the timer U73A is coupled to the second inverted input of the AND gate U66B.

The watchdog circuit (594) operates as a state machine having three states—waiting for a MONOK signal, waiting for a CONOK signal and sequence violated. The circuit (594) alternates between the waiting states unless the alternating sequence is violated or unless the alternating sequence did not begin with the MONOK signal. In that case, the circuit enters the sequence violated state.

The operation of the watchdog circuit (594) is as follows. As long as the output of the AND gate U66B is high, then the microprocessors (540) and (542) are indicated to be operating properly. A watchdog trip occurs either if no OK signal is received within 3.2 seconds, or the OK signals are out of sequence. Particularly, the OK sequence must alternate between the MONOK and the CONOK signal.

At startup, the inverted output of each flipflop U72A and U72B is high due to reset. Similarly, the output of the timer circuit U73A is high, so that the output of the AND gate U66B is high. With the inverted output of the flipflop U72A high, the AND gate U66C is enabled. Because the non-inverted output of the flipflop U72A is low, the AND gate U66D is disabled. The first pulse received should be the MONOK signal from the monitor microprocessor (540). Assuming the pulse is received, the pulse is applied to the second AND gate U66D, which has been disabled. The output of the NOR gate U69D clocks the flipflop U72A so that the outputs alternate. This has the effect of enabling the AND gate U66D and disabling the AND gate U66C. Assuming the next pulse received is the CONOK pulse, then the pulse is applied to the NOR gate U69D, which again clocks the flipflop U72A and is also applied to the disabled AND gate U66C. If consecutive pulses are received from the same processor, then such occurrence will be detected by one of the AND gates U66C or U66D. For example, if the AND gate U66C is enabled, indicating that the last pulse received was the CONOK pulse, and another CONOK pulse is received, then the output of the AND gate U66C goes high, causing the NOR gate U69C to clock the flipflop U72B so that its inverted output goes low, causing the output of the AND gate U66B to go low to indicate a watchdog error condition. Similarly, if two consecutive MONOK pulses are received, then the output of the AND gate U66D goes high to clock the flipflop U72B through the NOR gate U69C.

The watchdog circuit (594) otherwise detects a failure if no pulse is received every 3.2 seconds. Particularly, when either the MONOK or CONOK signal pulses the NOR gate U69D, that pulse is used to reset the timer circuit U73A. If no pulse is received for 3.2 seconds from either the MONOK or CONOK inputs, then the timer U73D output to the AND gate U66B goes low, so that the DOGOUT output of the AND gate U66B goes low to indicate a watchdog failure. A watchdog failure results in a reset signal being sent to the microprocessors (540) and (542). Also, a watchdog failure disables the plunger motor drive (582) and the valve motor drive (584), via the respective latch circuits (578) and (580). Disabling the motors stops all pumping action, leaving one of the pump chambers tube ends pinched.

L. System Peripherals

Figure 39:
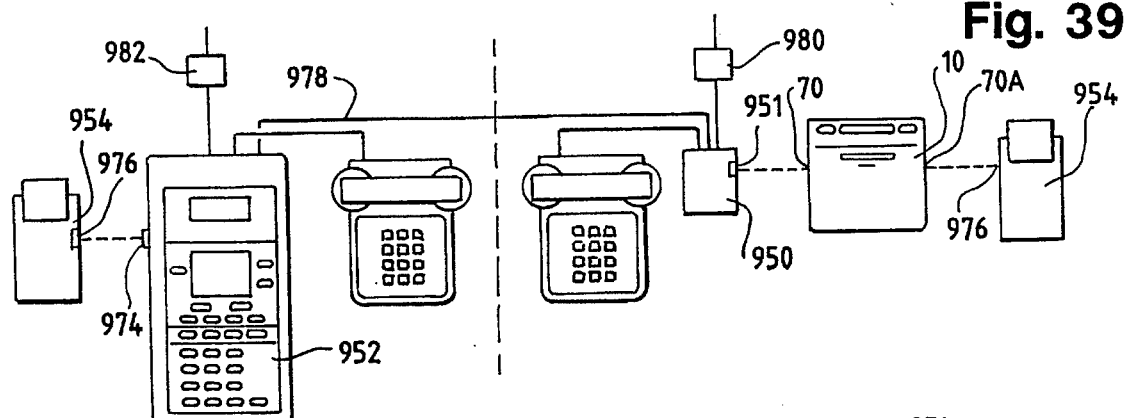
FIG. 39 is a schematic representation of the pump peripherals communicatingly associated.
Figure 40:
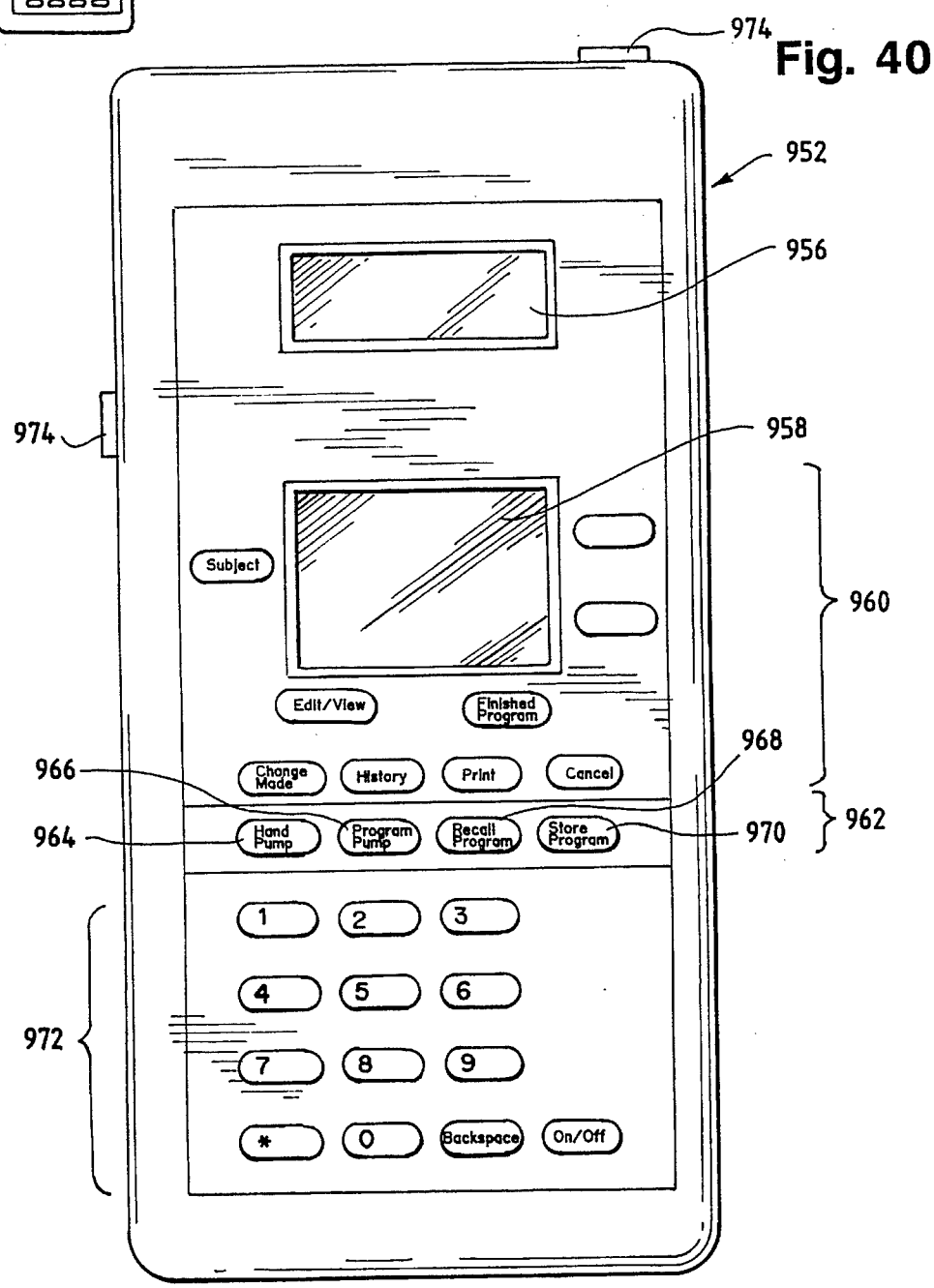
FIG. 40 is a plan view of the remote programmer unit.

The ambulatory infusion pump (10) is part of a system illustrated in FIG. 39 which includes, in addition to the soft pump case (12), the solution bag (64), the pump cassette (86) and the PCA switch (44), a remote communication interface unit (950), remote programmer (952) and a printer (954).

Figure 41:
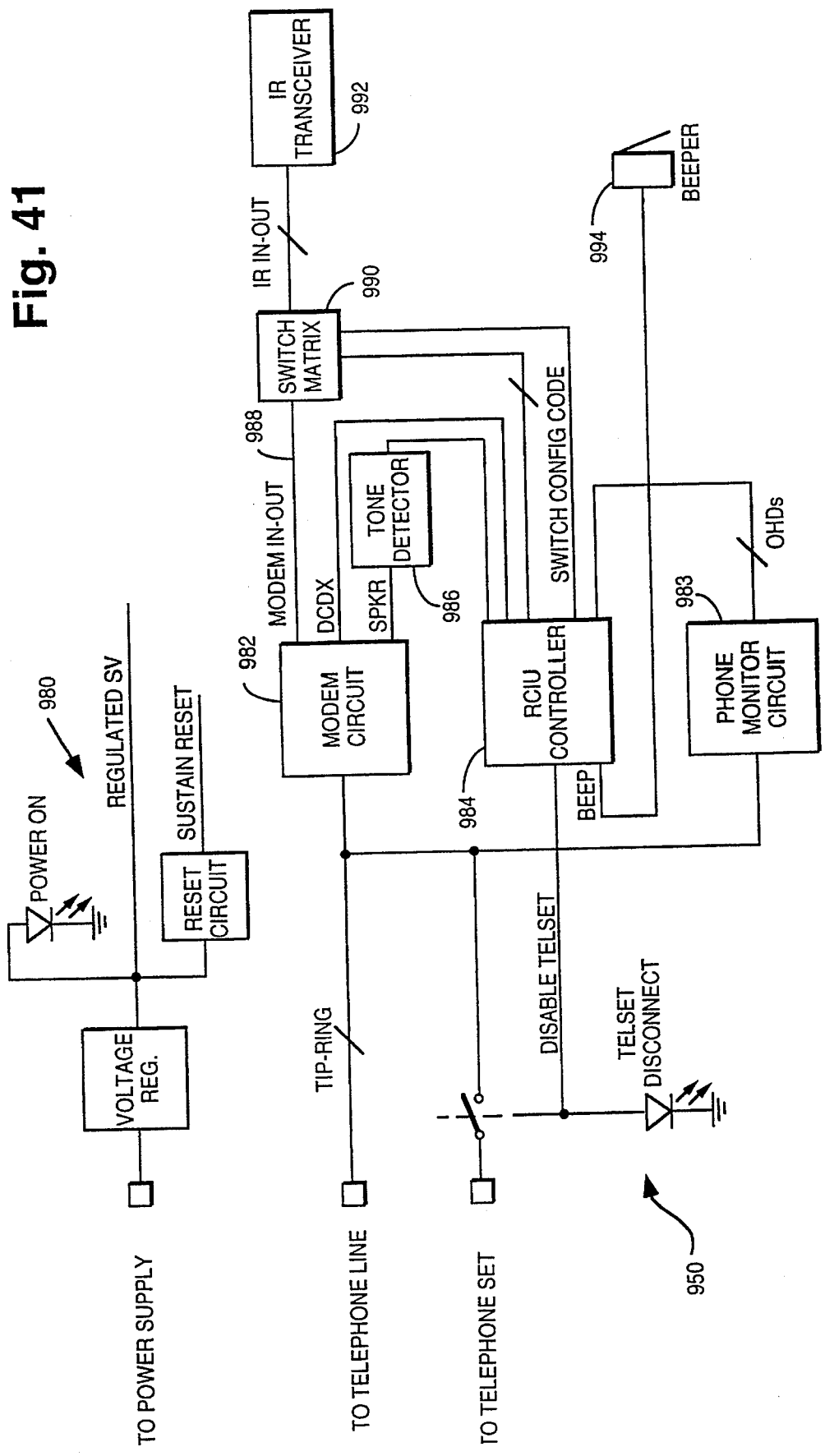
FIG. 41 is a block diagram of an electrical circuit for a remote communication interface unit for use with the ambulatory infusion pump.

The RCIU (950) consists of a telephone modem and an IR input/output (951). A block diagram of the RCIU is illustrated in FIG. 41. With reference to FIG. 41, a block diagram illustrates a circuit for the RCIU (950), see FIG. 39. The RCIU is a telephone to modulated infrared transceiver acting as an interface between a local pump (10) and remote programmer (952), as illustrated in FIG. 39. Particularly, the pump (10) is adapted to receive infrared signals for remote programming. When the remote programmer (952) is physically remote, it cannot directly transmit IR signals to the pump (10). In that instance, the programmer (952) transmits programming information over commercial phone lines to the RCIU (950), which converts the information to infrared signals to the pump (10), and vice versa.

The RCIU (950) includes a power supply circuit (980) for powering the various circuit components. A modem circuit (982) is connected to the telephone line, as is a phone monitor circuit (983). The modem circuit (982) is connected to a tone detector (986) which provides an answer tone detected signal to an RCIU controller (984). The modem circuit (982) has a data line (988) connected to a switch matrix (990). The switch matrix 090) is also connected to an IR transceiver circuit (992) and to the RCIU controller (984). The RCIU controller is also connected to a beeper (994).

The specific circuitry for the RCIU (950) is conventional in nature and therefore is not described in detail herein. Particularly, the RCIU controller acts as a conventional modem to initiate or receive "phone calls" to a remote programmer (952), see FIG. 39. Communication is established in a conventional manner. Once communication is established, then the RCIU controller (984) controls operation of the switch matrix (990) to receive data either over the phone line via the modem circuit (982) or via the IR transceiver circuit (992), converts the received data to the other format, i.e., IR to modem or vice versa, and then transmits the received data in the converted format via the opposite media from which it was received.

The remote programmer (952) includes a status LCD (956) and a program LCD (958). The program LCD (958) is identical to the program LCD (28) of the ambulatory infusion pump (10). The remote programmer also includes a keyboard (960) which is identical to the keyboard (30) of the ambulatory infusion pump (10). In addition, the remote programmer includes a number of numeric entry controls (962) which simplify programming via the remote programmer. An IR input/output device (964) is provided for communication with the IR window (70) of the ambulatory infusion pump (10) and the IR input/outputs of the RCIU (950).

Figure 34:
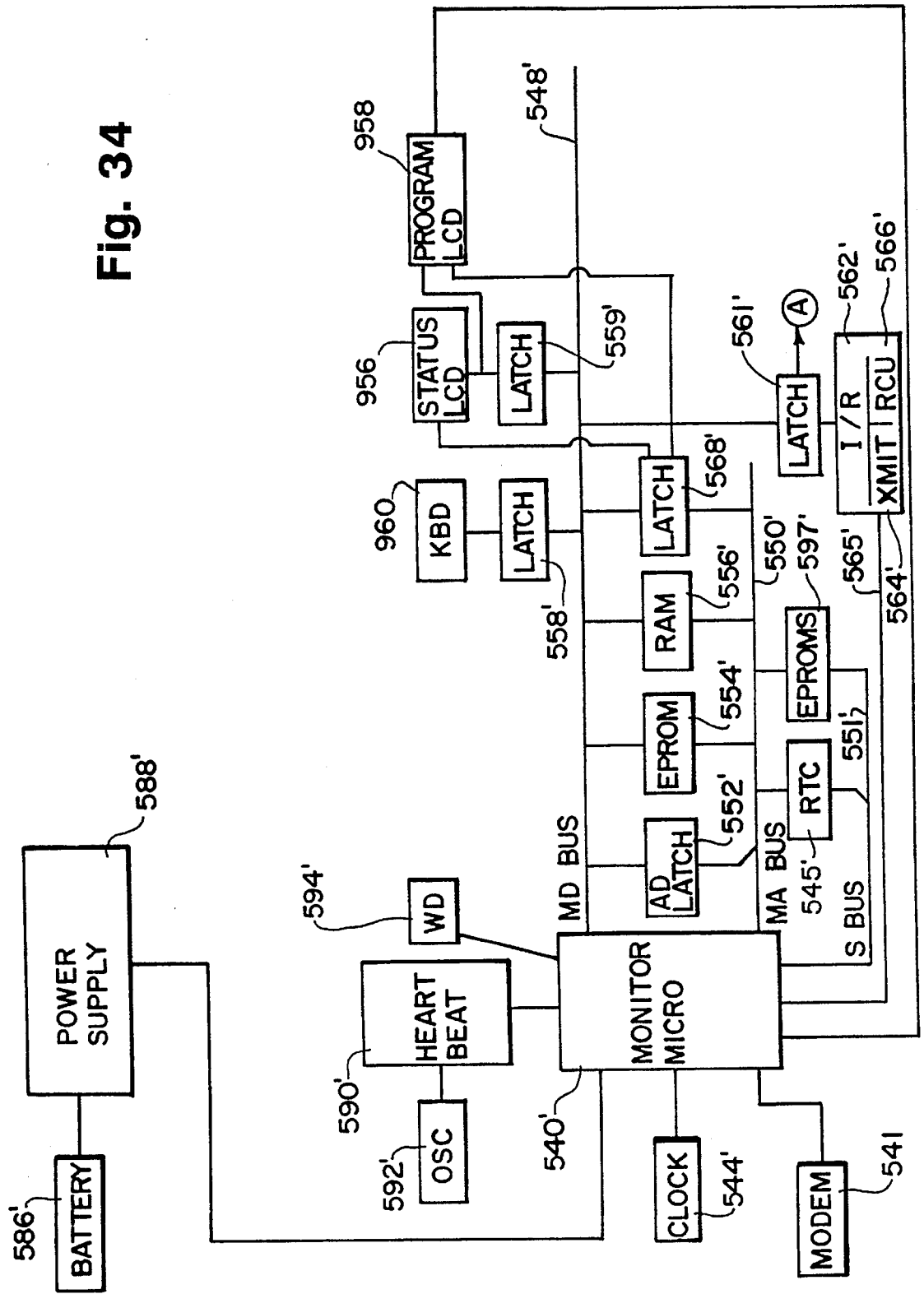
FIG. 34 is a block diagram of an electrical circuit for the remote programmer.

With reference to FIG. 34, a block diagram illustrates an electrical circuit for the remote programmer (952). The circuit is essentially a duplicate of the circuit associated with the monitor microprocessor (540), see FIG. 32. Therefore, the circuit is not described in detail herein. For simplicity, like elements are indicated with like, primed reference numerals. Among the differences are the addition of an internal modem circuit (541) connected to the monitor microprocessor (540'). The modem circuit (541) may include, for example, a type CH1782 modem circuit module. Also, the patient LCD is replaced with the status LCD (956). Both the status LCD (956) and program LCD (958) are connected to the latch circuit (559'). Also, a conventional microprocessor watchdog (594') is used.

The printer (954) is a standard printing device having an IR input/output (966).

FIG. 39 illustrates remote programming use of the remote programmer (952) and the RCIU (950). Communication may be transmitted over commercial phone line (966). The RCIU (950) is located in the immediate vicinity of the pump and is powered by an AC adaptor (970). An IR window (70) of the pump is maintained within approximately six inches of an IR input/output (951) of the RCIU (950). The printer (966) may be linked to a second IR window (70A) of the pump (10). At the remote location, the remote programmer (952) is connected directly to the commercial phone line (968). It is powered by an AC adaptor (972). A printer (954) having an IR input/output (966) is maintained in infrared communication with an IR input/output (964) of the remote programmer (952). The programmer (952) can be used for direct wireless programming of the pump by positioning the programmer with its IR input/output (964) in direct IR communication with the IR window (970) of the pump (10) and programming and access to pump data can be conducted in the manner discussed below in Section M4 with respect to FIG. 35D.

M. Monitor Microprocessor Software

As set forth ,above, the ambulatory infusion pump includes a monitor microprocessor (540) and a control microprocessor (542). The monitor microprocessor and its software generally supports programming, user interface, communication and peripheral hardware with execution of the pumping sequence by the control microprocessor. The flow diagram of FIG. 35A comprises a generalized flow diagram representing the main routine of the monitor microprocessor software. FIGS. 35B–D represent sub-routines called by the monitor microprocessor main routine.

1. Main Monitor Routine

The monitor microprocessor main routine begins at block (620), which represents a user powering on the pump, at which time initialization of the monitor main routine and self-test routines are performed. The self-tests includes RAM test, ROM test, integrity of delivered program, communication between the control and monitor microprocessors and test of the pump beeper and visual alarms. Block (622) represents a routine for supporting the programmer display and the programmer controls. A detailed flow diagram of block (622) is provided in FIG. 35B. Supports for the patient display and the patient controls is provided at block (624). This includes drawing of the patient display such as that illustrated in FIG. 26 and support for the on/off control (38) and the bolus dose control (40) shown in FIG. 25. At block (626) support is provided for the beeper and patient LED which provide both indication of normal pump operation and, under circumstances described below, error notification. Communication with the control microprocessor is conducted at block (628) which shown in greater detail in the flow diagram of FIG. 35C.

At block (630) the routine determines whether or not the pump is currently delivering a therapy. If not, printer support is provided at block (632). The printer support controls printing of historical data and other operating parameters. Communication with the remote programmer is supported at block (634). A detailed flow diagram of the substantive controlling communication support with the remote programmer is contained in FIG. 35D. The monitor microprocessor is put to sleep at (636). The monitor microprocessor remains asleep until block (638), whereat the next heartbeat awakens the monitor microprocessor and the main routine continues.

Returning to decision block (630), if the pump is delivering a therapy, decision block (640) is reached and a determination is made whether the program entered at block (622) has been mapped by the monitor microprocessor. If it has not, the program is mapped at block (642). At block (642), the monitor microprocessor generates two program maps: a monitor program map and a control program map. The monitor program map contains a series of operations necessary to administer the delivery profile entered at block (622) in the manner described with reference to FIG. 35B. Following compilation of the monitor and control program maps, the monitor program map is executed at block (644). Of course, if the program maps have already been compiled, block (644) is reached directly following decision block (640). If the monitor program map requires actuation of the pump mechanics, an appropriate command is generated and flagged at block (644). The flag is subsequently detected at block (628) and communication with the control microprocessor is conducted in the manner discussed with reference to FIG. 35C. In a like manner, if a control program map is constructed in block (642), it is flagged and communicated to the control microprocessor at block (628).

2. Support Programmer Display and Controls Routine

With reference to FIG. 35B, a flow diagram illustrates the support programmer display and programmer controls of block (622). In describing the support programmer display and programmer control, typical programming sequences are discussed. It should be noted, however, that at those blocks described below where the user is assumed to have taken action, such as block (654) where the user positions the cursor with the "up" and "down" keys, the user may instead press the "cancel" button, thus returning to the previously selected mode screen or the user may do nothing at all, essentially leaving the pump in limbo.

At block (648) the current mode screen is drawn, such as the "intermittent with bolus" mode screen shown in FIG. 29. As discussed with reference to FIG. 27, five delivery modes (517) are available: "continuous", "continuous with PCA", "continuous with taper", "intermittent" and "intermittent with bolus". These delivery modes are discussed in greater detail in Section H above with reference to FIG. 37A–E.

At decision block (650) determination is made whether or not a user has depressed the "change mode" button (526). If the "change mode" button (526) has been pressed, SELECT DELIVERY MODE screen illustrated at FIG. 27 is drawn at block (652). At block (654), the user positions the cursor with the up and down keys (522) to highlight with the cursor the intended delivery mode. The user presses the "select" button (523) at block (656) when the desired delivery mode has been highlighted by the cursor. The mode screen for the selected mode is then drawn at block (658), following which the main routine is resumed.

If at decision block (650) the "change mode" button (526) has not been pressed, at block (660) the routine determines whether the "edit/view" button (525) has been pressed. Pressing of the "edit/view" button allows the user to enter new parameters for the selected delivery mode. At block (662) the "setup" screen is drawn for the selected delivery mode. A sample "setup" screen is illustrated at FIG. 28. At block (664) the user positions the cursor with the "up" and "down" keys (522) for the purpose of entering or altering one of the input options (521).

The program includes a lockout feature to prevent unauthorized or inadvertent alteration of selected input options. A clinician can prevent alteration of selected input options without input of a selected password or code where restricted access to an input option is necessary for patient safety. The feature is controlled by a clinician entering a selected lock level which tells the program whether a particular input option can be altered. If the input option can be altered, the input option line, including the input valves, is highlighted when the cursor is positioned at the particular input option. This highlighting is known as a "regular cursor" and is illustrated at (665) of FIG. 28. If the input option cannot be altered, only a vertical line or "edge cursor" to the immediate left of the input option will be highlighted when the cursor is positioned at that particular input option, as illustrated at (665A) of FIG. 28.

At decision block (666) the routine determines whether the user is in lock level "0", which allows unrestricted access. If the user is in lock level "0", the regular cursor is drawn at block (668). If the user is not in lock level "0", at decision block (669) the routine determines whether the new cursor position or input option is lock level protected. If it is not, at block (668) the regular cursor is produced. If the cursor position or input option is lock level protected, at block (670) the edge cursor is produced.

Returning m block (668), if the regular cursor is produced at block (672), the routine inquires whether the user has pressed the "select" key (523). If not, the user may reposition the cursor with the "up" and "down" keys (522) at block (664). If the user has pressed the "select" key (523), the user may then modify the input value parameter with the "up" and "down" keys (522) at block (674). When a desired value is arrived at block (674), the user presses the "select" key (523) at (676). The routine then simultaneously "deselects" the input option retracting the cursor, and "enters" the modified value. Block (678) represents three user options. The user may return to block (664) and reposition the cursor with the "up" and "down" keys (522). Or, the user may press the "cancel" key (527), block (679), deleting the new program. The previous "mode" screen will then be drawn at block (680) with the input option values unchanged. The main routine is then rejoined at block (624). The third option shown at block (682) is for the user to press "finished program". The new "mode" screen with the newly selected values is then drawn at (684). The main routine is then rejoined at block (624).

3. Support Communication with Control Microprocessor Routine

Figure 35A:
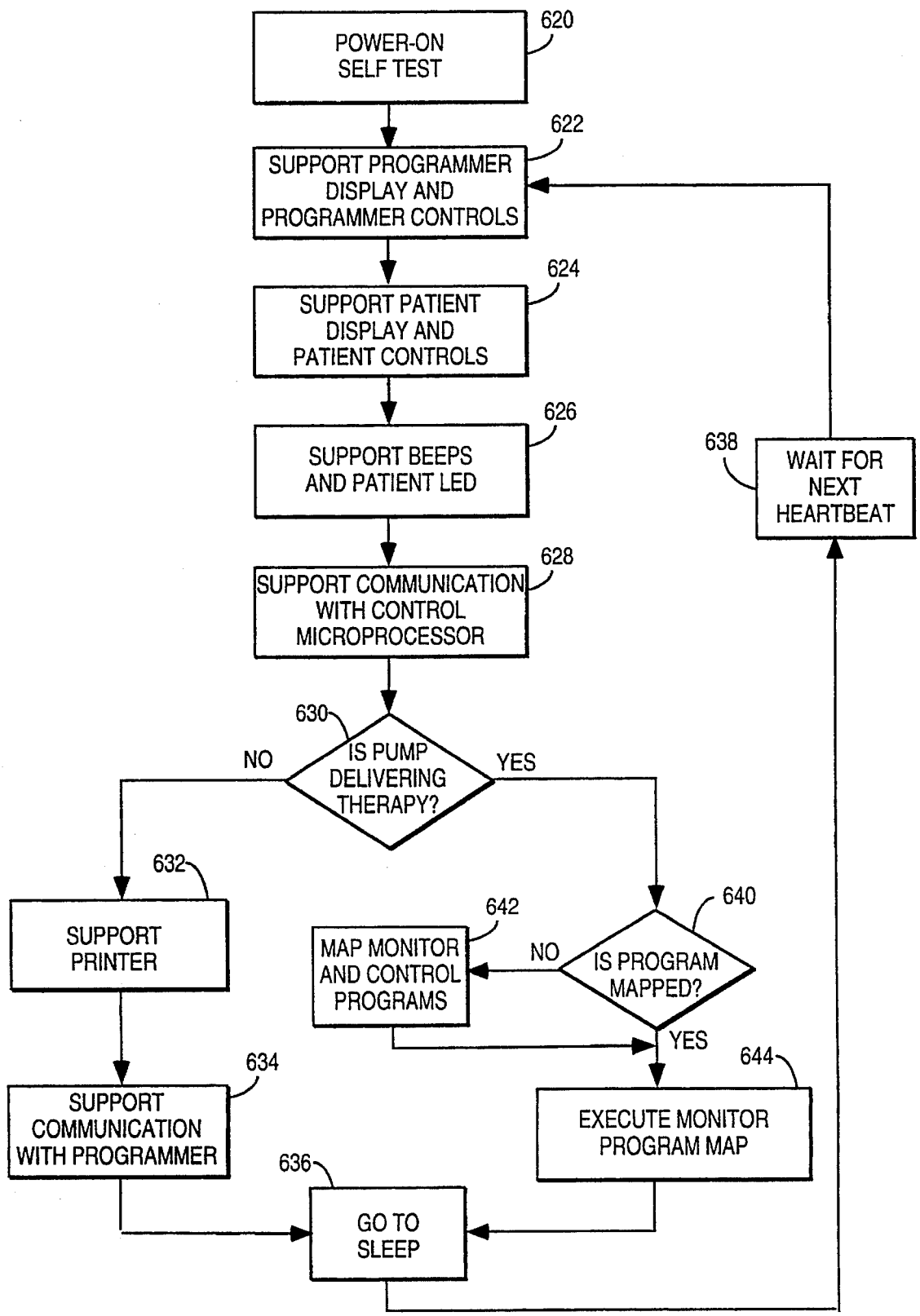
FIG. 35A is a flow diagram of the main routine of the monitor microprocessor software for use with the ambulatory infusion pump.
Figure 35B:
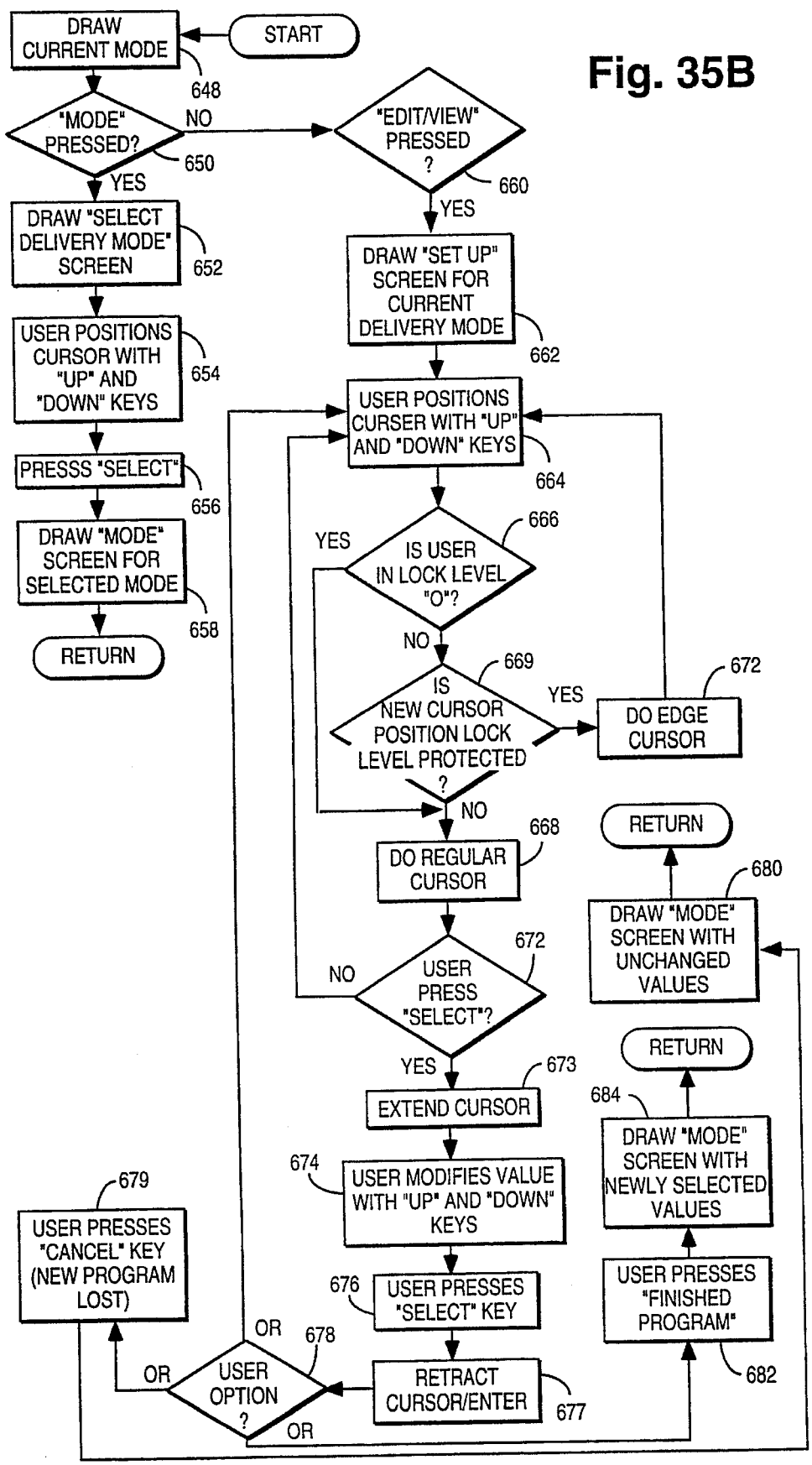
FIG. 35B is a flow diagram of the "support patient display and patient controls" subroutine of FIG. 35A.
Figure 35C:
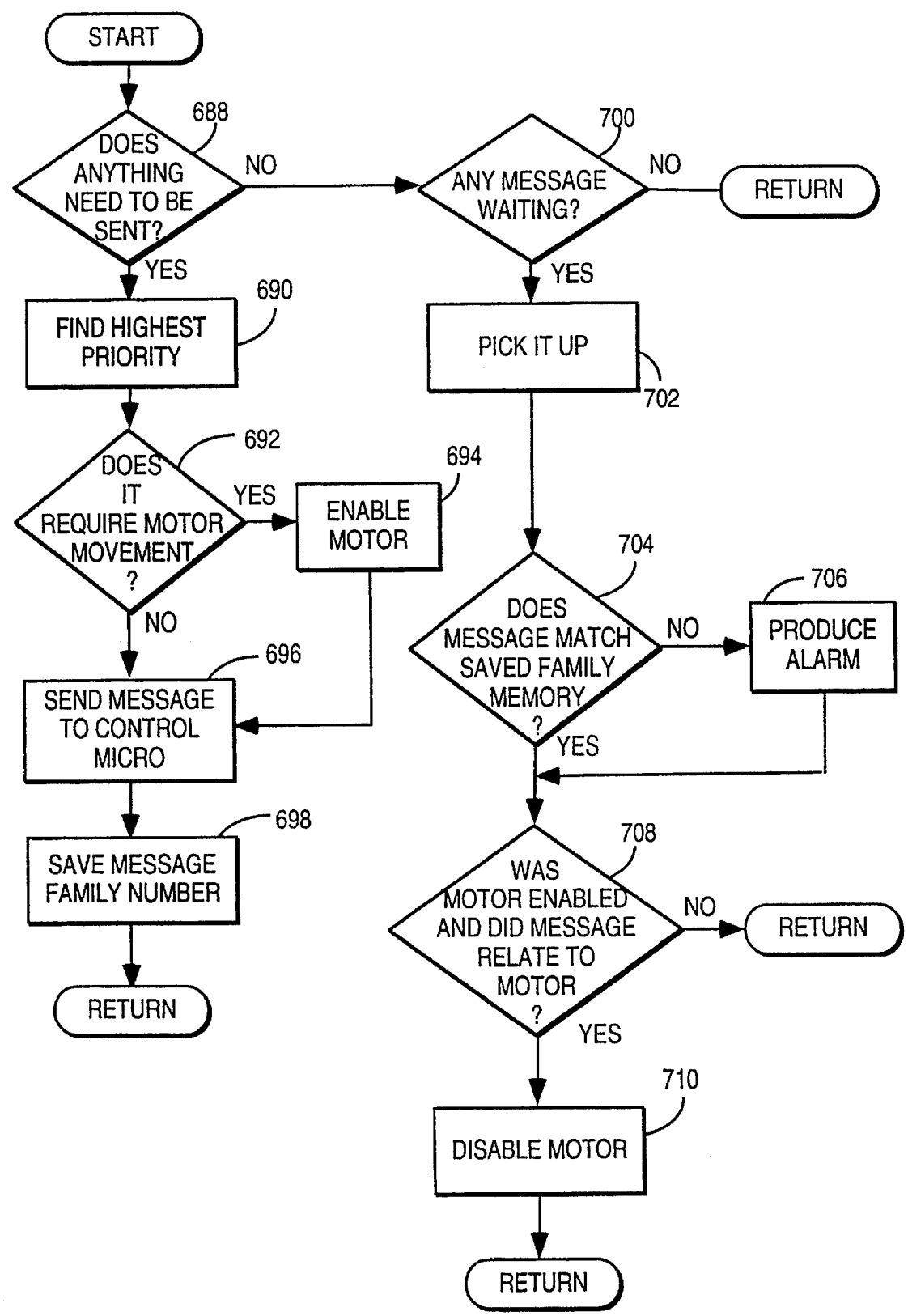
FIG. 35C is a flow diagram of the "support communication with control microprocessor" subroutine of FIG. 35A.
Figure 35D:
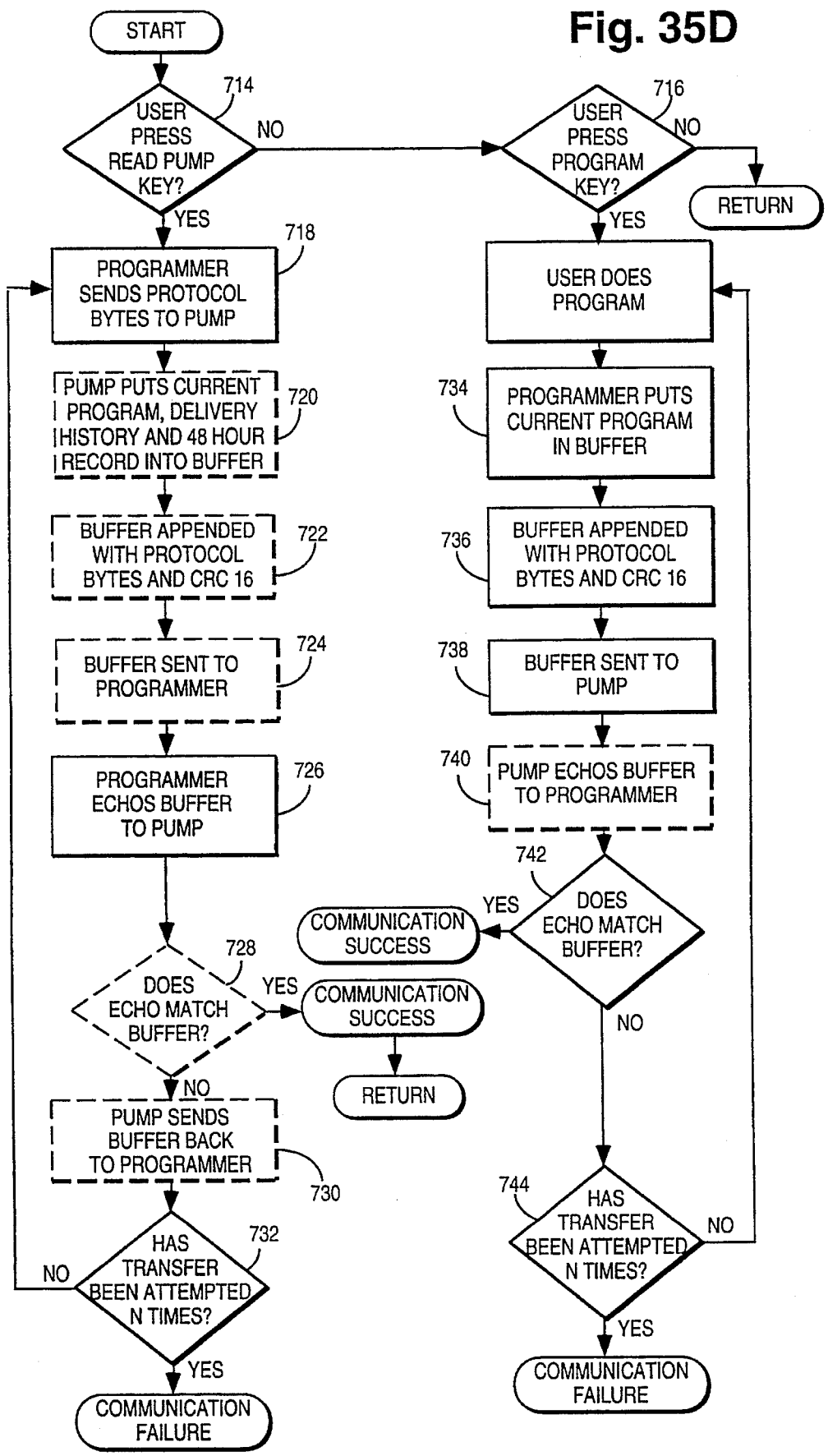
FIG. 35D is a flow diagram of the "support communication with the remote programmer" subroutine of FIG. 35A.

FIG. 35C is a flow diagram illustrating in detail block (628) of FIG. 35A, "support communication with control microprocessor". Communication begins at control block (688), where the routine determines whether a flag or flags have been raised at the "execute monitor program map" block (644) or the "program map" block (642) of the main monitor routine, FIG. 35A. If such a flag has been raised, then the highest priority message will be found at block (690). At decision block (692) determination is made whether the message to be sent requires movement of either the plunger motor or the valve motor. If the answer is yes, the appropriate motor is enabled at block (694). At block (696), the message is then sent to the control microprocessor. At block (698), the message family number is stored. The family number will subsequently be compared with a confirming message conveyed by the control microprocessor as discussed below.

If at decision block (688) there is no message to be sent, at decision block (700) the routine determines whether any message is waiting from the control microprocessor. If no message is waiting, the main monitor microprocessor routine simply continues. If a message is waiting from the control microprocessor, the message is picked up at block (702). At decision block (704) it is determined whether the message picked up matches the message saved at block (698). If the message does not match, an alarm is produced at block (706). Whether the motor had been enabled and whether the picked up message relates to the motor is determined at block (728). If the answer to both questions is yes, the motor is disabled at block (710) and the subroutine returns to the main routine. If the answer is no, the subroutine returns directly to the main routine.

4. Support Communication with Remote Programmer Routine

FIG. 35D is a flow diagram illustrating the "support communication with the remote programmer" subroutine of block (634) of the main monitor routine. Those steps being performed by the remote programmer (952) are shown in solid lines, and those being performed by the monitor microprocessor are shown in dotted lines. Communication between the remote programmer and the pump is conducted in one of three ways detailed in Section L above: 1) directly by infrared linkage; 2) through the remote communication interface unit (RCIU); or 3) by linkage to the remote programmer through a local RCIU, an RCIU at the remote programmer location and phone lines. At decision block (714) the routine determines whether the user has pressed the "Read Pump" key (964) of the remote programmer. If not, at decision block (716) determination is made whether the user has pressed the "Program Pump" key (966). If the answer is no, the routine returns to the main monitor routine and the monitor microprocessor is put to sleep at block (636) (see FIG. 35A).

If at decision block (714) the user has pressed the "Read Pump" key (964), the remote programmer sends protocol bytes to the pump at (718). The protocol bytes include, for example, the respective serial numbers of the pump and remote programmer. At block (720), the monitor microprocessor puts the current program, delivery history and previous forty-eight hour record into a buffer. At block (722), the monitor microprocessor appends the protocol bytes and CRC 16 to the buffer. At block (724), the buffer is sent by the monitor microprocessor to the remote programmer. At block (726), the remote programmer echoes the buffer to the remote microprocessor. At decision block (728), the monitor microprocessor determines whether the buffer echoed at box (726) matches the buffer sent to the remote programmer at box (724). If the answer is yes, the communication is a success and the monitor microprocessor continues the main routine at block (636) of FIG. 35A. If the echo does not match the buffer, at block (730) the pump monitor microprocessor sends the buffer back to the remote programmer. At decision block (732) the remote programmer determines whether the transfer has been attempted a select number, or n times. If it has and the echo fails to match the buffer sent by the monitor microprocessor of the pump, them is a communication failure and an alarm is sounded. If at decision block (732) the remote programmer microprocessor determines the transfer has not been attempted n times, the routine returns to block (718) and is repeated until the echo matches the buffer or transfer has been attempted unsuccessfully n times.

If the user has pressed the "Program Pump" key (966) at decision block (716), the remote programmer puts the current programmer in a buffer. At block (736), the buffer is appended with the protocol bytes (e.g., pump and programmer serial numbers) and CRC-16. At block (738), the buffer is sent to the pump. At box (740), the pump monitor microprocessor echoes the buffer to the remote programmer. At decision block (742), the remote programmer determines whether the echo matches the buffer sent to the pump. If the answer is yes, the communication is a success, and the main routine of the monitor microprocessor is continued, with the new program being implemented in the same manner as if the program had been entered directly at the pump. If the echo does not match the buffer, at decision block (744) the determination is made whether the transfer has been attempted a select number or n times. If it has not, the routine continues at box (734) and repeats itself until the echo does match the buffer or the transfer has been attempted a n number of times, at which time communication is a failure and an alarm is sounded.

N. Control Microprocessor Software

Figure 36A:
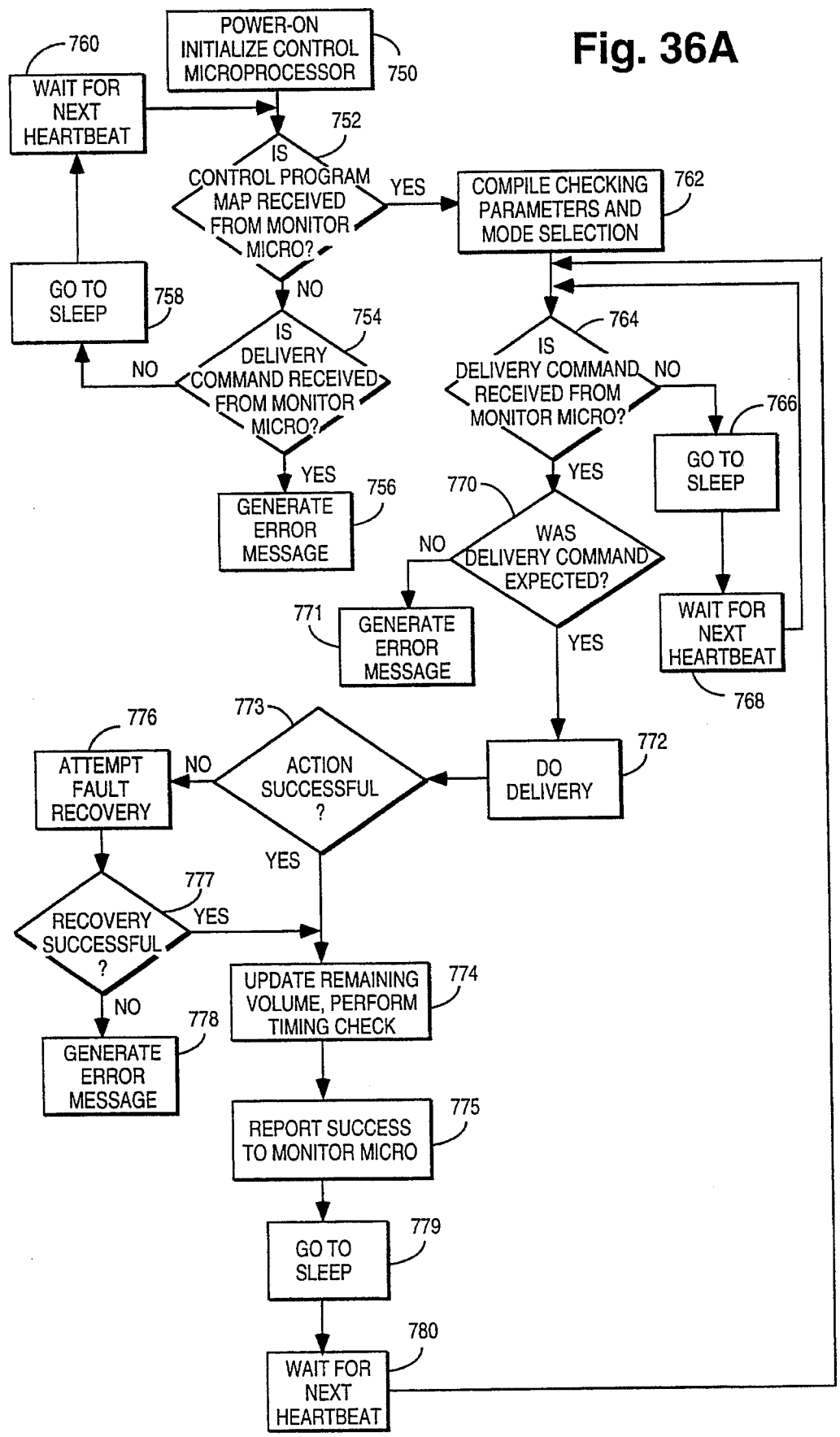
FIG. 36A is a flow diagram of the main routine of the control microprocessor software.

FIG. 36A is generalized flow diagram representing the major operational routine of the control microprocessor (542). The primary function of the control microprocessor (542) is to execute the plunger and valve motion control algorithms which are intended to provide variety of delivery profiles within acceptable predefined accuracy standards while minimizing energy consumption and further while continuously monitoring the pump mechanics to provide prompt notification of any failure conditions. FIGS. 36B–I are flow diagrams of subroutines called by the main control routine.

1. Main Control Routine

The main control routine begins at block (750) of FIG. 36A, wherein the main control microprocessor program is initialized. At decision block (752) it is determined whether the program map complied by the monitor microprocessor (540) at block (642) of FIG. 35A has been received from the monitor microprocessor through execution of the support communication with control microprocessor block (628) of FIG. 35A. If a program map has not been received from the monitor microprocessor, at decision block (754) it is determined whether a delivery command has been received from the monitor microprocessor. If a delivery command has been received, at block (756) an error message is generated because a system error has occurred if a delivery command is received by the control microprocessor without having first received a program map. The error message generated at block (756), like all error messages discussed in FIGS. 36A–I, is sent to monitor microprocessor (540), which activates an appropriate alarm. The control microprocessor verifies the activation of an appropriate alarm by the monitor microprocessor. If the control microprocessor is unable to verify that the appropriate alarm has been activated, the control microprocessor will directly activate an alarm. If at block (754) a delivery command is not received from the monitor microprocessor, the control microprocessor is put to sleep at block (758) and at block (760) the control microprocessor is awakened by the next heartbeat and decision block (752) is again entered.

If at decision block (752) a program map has been received from the monitor microprocessor (540), the program map is compiled at block (762) to set forth checking or verification parameters and further to determine which of the five pump operation modes is required to fully execute the program map. A determination is made at decision block (764) whether a delivery command has been received from the monitor microprocessor. If no delivery command has been received, the control microprocessor (542) is put to sleep at block (766) until it is awakened at the next heartbeat at block (768) and the control microprocessor then again executes decision block (764).

If a delivery command has been received from the monitor microprocessor, at decision block (770) it is determined whether the delivery command was expected. If a delivery command was received and was not expected, an error message is generated and conveyed to the monitor microprocessor (540). If the delivery command was expected at decision block (770), a delivery is executed at block (772). Delivery commands from the monitor microprocessor only specify whether the infusion is to be 5, 25 or 125 microliters. The delivery at block (772) is conducted in accordance with the mode selection configured at block (762) to satisfy the delivery profile. Delivery is executed through one of five delivery routines which are discussed in greater detail with reference to FIGS. 37B–F. Inquiry is made at decision block (773) whether the delivery task has been successfully completed. If the action has been successfully completed, at block (774) the volume remaining in the reservoir is updated and the acceptability of the flow rate is confirmed. That is, when a select volume of liquid has been delivered, the routine determines if the time to deliver the select volume provides an acceptable flow rate. If the flow rate is acceptable, the routine is reset. At block (775) successful completion of the delivery sequence is reported to the monitor microprocessor. Although not illustrated in FIG. 36A, if the timing check performed at block (774) does not confirm proper operation of the pump, an error message is sent to the monitor microprocessor (540).

Returning to decision block (773), if a pumping action has not been successfully completed, at block (776) fault recovery is attempted. The fault recovery routine is shown in detail in FIG. 36I and will be discussed below. At decision block (777) the routine determines whether the recovery was successful. If the recovery was successful, the routine continues at block (774). If the recovery was not successful, an error message is generated at block (778) and conveyed to the monitor microprocessor (540). Continuing with block (775), following report of a successful delivery action to the monitor microprocessor (540), the control microprocessor (542) is put to sleep at block (779) until the next heartbeat at (780), wherein the control microprocessor (542) is awakened and the main routine returns to decision block (764).

As discussed above with reference to blocks (762) and (772), the main control routine includes five subroutines, FIGS. 36B–F, for executing pump modes 1–5. The subroutines actuate the plunger and valve motors so as to discharge the desired volume of medication at the desired rate for the desired time period. An overview of modes 1–5 is contained in FIG. 38. Many of the details set forth in FIG. 38 will be apparent following discussion of FIGS. 36B–F below. For the present purpose, it is only necessary to know that mode 1 delivers fluid at a rate of between 0.1–0.4 ml/hr.; mode 2 delivers liquid at a rate of 0.5–7.9 ml/hr.; mode 3 delivers medication at a rate of 8–49.9 ml/hr.; mode 4 delivers medication at a rate of 50–249 ml/hr.; and mode 5 delivers medication at a rate of 250–390 ml/hr. Determination is made which one of modes 1–5 is executed at the "do delivery" block (772) in accordance with the selected delivery profile delivered to the control microprocessor as the control program map. See FIG. 36A, block (752,762).

2. Mode "1" Delivery Routine

Figure 36B:
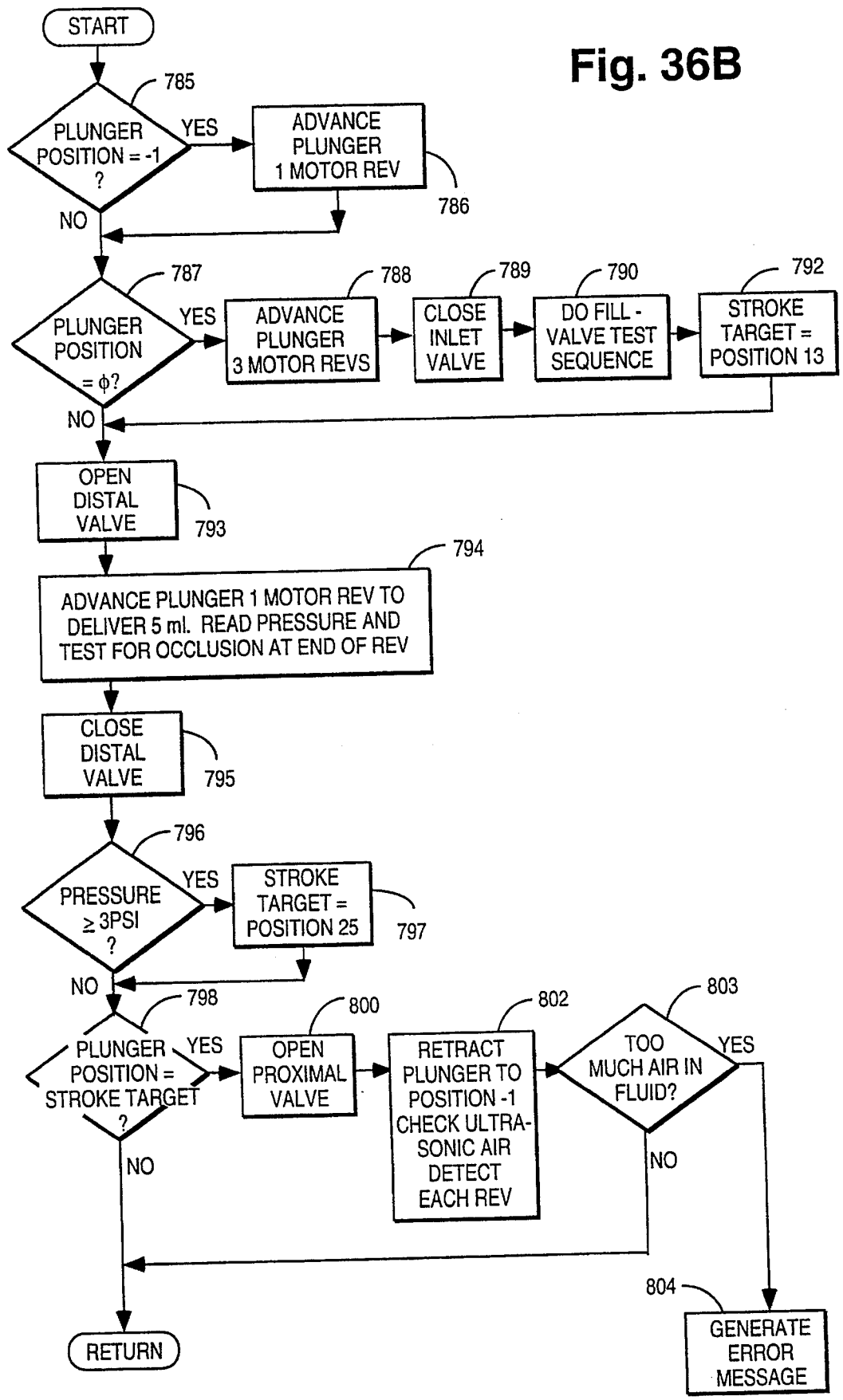
FIG. 36B is a flow diagram of the mode "1" delivery routine.

FIG. 36B is a flow diagram illustrating a routine for executing mode 1 delivery. At decision block (785) it is determined whether the plunger is at position "–1". If it is, at block (786) the plunger motor (256) is advanced one revolution. Thus, block (785–786) constitute a refill condensation sequence which ensures that when the plunger (120) is at position "0", the pump chamber (140) is at the expected volume. If the plunger position is not equal to "–1" at block (785) or following advancement of the plunger one motor revolution at (786), at decision block (787) it is determined if the plunger is at position "0". If the plunger is at position "0", the plunger motor is advanced three motor revolutions to advance the plunger to position "3" at block (788). Advancing the plunger three motor revolutions at block (788) negates any tolerance stacking between the position of the plunger and the platen, and thereby improves pump accuracy. At block (789) the proximal or inlet valve (122) is closed. Next, at block (790) a fill and valve leak test sequence is executed. A flow diagram of block (790) is shown in FIG. 36G and is discussed below. Following execution of the fill and leak test sequence (790), at block (792) the stroke target is set to position "13". "13" is the preferred target position so that the pump chamber is compressed only a total of thirteen revolutions to prevent the pump chamber from acquiring a "memory" of less than the full refill volume as a result of occupying a compressed position for extended periods of time. At block (793) the distal or outlet valve (124) is opened. If at decision block (787) the plunger position is not equal to "0", the routine continues at block (793) with the opening of the distal valve. At block (794) the plunger is advanced one motor revolution to deliver five microliters of medication. Concurrently, the pressure within the pump chamber (140) is measured by the pressure transducer (362) for the purpose of detecting a downstream occlusion by comparison of the read pressure with a predetermined reference pressure. If the predetermined reference pressure is exceeded, a downstream occlusion error message is generated by the control microprocessor and conveyed to the monitor microprocessor. If no downstream occlusion is detected, at block (795) the distal valve (124) is closed. If it is, at decision block (796) it is determined whether the pump chamber pressure is greater than or equal to three psi above the inlet line pressure. If it is, at block (797) the stroke target position is set to "25". The stroke target position is set to "25" at block (797) in order to ensure that the pump chamber will be subject to sufficient compression during the pumping sequence to generate a pump chamber pressure greater than the reference pressure so as to ensure any downstream occlusion is detected. If at block (796) the pump chamber pressure is less than three psi above the inlet line pressure, or following setting of the stroke target to "25" at block (797), at decision block (798) the routine determines whether the plunger has attained the stroke target position. If so, at block (800) the inlet or proximal valve (122) is opened. At (82) the plunger is then retracted by reverse rotation of the plunger motor to position "–1". Also at block (802), at each revolution of the plunger motor the ultrasonic air detect (130) transmitter produces an ultrasonic signal which is received by the air detect receiver. This procedure is discussed above in Section F. The receiver then transmits a signal to control microprocessor (542), the amplitude of which indicates whether an air or liquid is present in the tube segment between the transmitter and receiver. More particularly, the ultrasonic air detect takes a snap shot of a tube segment between the transmitter and receiver of the ultrasonic air detect (130) containing on the order of 25 microliters of liquid each revolution of the plunger motor. If the amplitude of the signal received from the ultrasonic air detect indicates that greater than 50% of the volume of the tube segment is filled with air, the microprocessor stores an "air in tube" signal. As the plunger motor completes the next revolution, a new 5 microliters is introduced into the tube segment as 5 microliters leaves the tube segment and another pulse is transmitted by the transmitter. If the amplitude of the signal dictates, the microprocessor stores an "air in tube" signal. At decision block (803) the routine determines if the sum of the "air in tube" signals exceeds a select number for any two consecutive refill cycles. The select number is preferably 15. If the select number is exceeded, pump operation is halted and an error message is generated at block (804). If the select number is not exceeded, the routine returns to block (773) of FIG. 36A. Likewise, if at block (798) it is determined that the plunger is not at the stroke target position, the routine returns to block (773) of FIG. 36A.

3. Mode "2" Delivery Routine

Figure 36C:
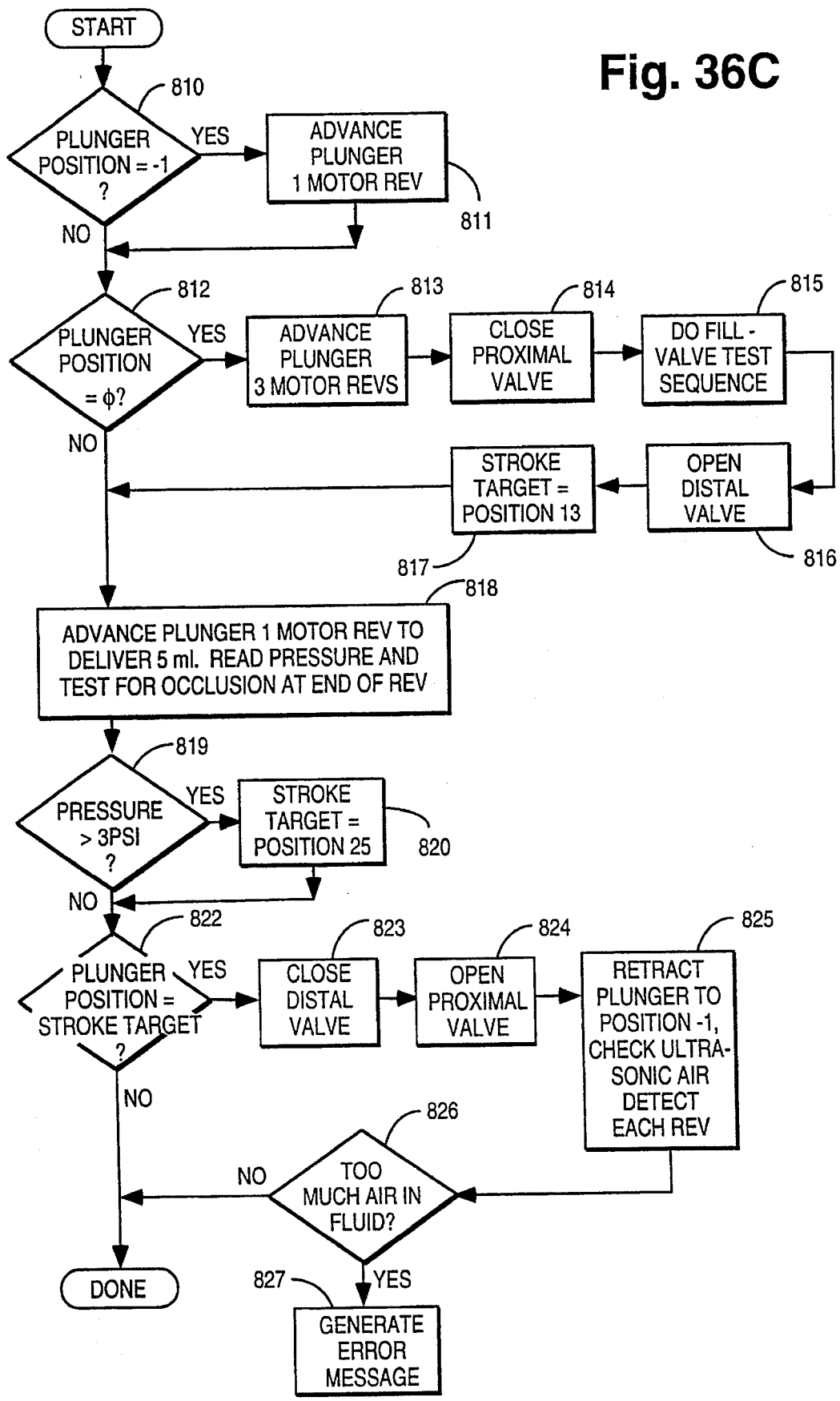
FIG. 36C is a flow diagram of the mode "2" delivery routine.

The routine for executing delivery mode (2) is illustrated in the flow diagram of FIG. 36C. At decision block (810) the routine determines whether the plunger is in position "–1". If the plunger is in position "–1", the plunger is advanced one motor revolution to position "0" at block (811), the "refill compensation sequence" discussed above with reference to blocks (785–786) of FIG. 36B. If the plunger is not in position "–1", or following block (811) at decision block (812) it is determined whether the plunger is in position "0". If the plunger is in position "0", at block (813) the plunger motor is advanced three revolutions, thereby advancing the plunger to position "3", as discussed above with respect to block (788) of FIG. 36B. At block (814) the proximal or inlet valve (122) is closed. Next, at block (815) the fill valve and leak test sequence is executed. A flow diagram of block (815) is shown in FIG. 36G, and is discussed below. Following execution of the fill valve and leak test sequence at block (815), at block (816) the outlet or distal valve (124) is opened. At block (817) the stroke target is set to "13" and the routine continues at block (818) in the same manner as if the plunger position had not been equal to "0" at decision block (812). At block (818) the plunger motor is advanced one revolution to deliver five microliters of medication. Concurrently, pressure within the pump chamber (140) is measured by the pressure transducer (362) for the purpose of detecting a downstream occlusion. The pressure within the pump chamber (140) is compared with a predetermined reference pressure. If the predetermined reference pressure is exceeded, an error message is generated. If the predetermined reference pressure is not exceeded, the routine continues at decision block (819). At decision block (819) it is determined whether the pump chamber pressure is greater than or equal to three psi above the inlet line pressure which is determined during the valve test sequence at block (815) and is designated in FIG. 36G as (A). If it is, the stroke target position is set to "25" at box (820) for the reasons set forth above with respect to block (797) of FIG. 36B. If the pump chamber pressure is found not to be greater than or equal to three psi above the inlet line pressure at decision block (819), or following setting of the target stroke position at blocks (820), it is determined whether the plunger is at the stroke target position. If it is, at block (823) the outlet or distal valve (124) is closed. Thereafter, at block (824) the inlet or proximal valve (122) is opened. At block (825) the plunger motor is reversed and the plunger is retracted to position "–1" while the ultrasonic air detect (130) is actuated after each plunger motor revolution. At decision block (826) the routine determines whether excessive air has been detected in the incoming fluid as discussed above with reference to block (803) of FIG. 36B and, if so, an error message is generated at block (827). If the amount of air in the fluid is not excessive, the routine returns to block (773) of the main control routine illustrated in FIG. 36A. Likewise, if at decision block (822) the plunger position is not equal to the stroke target, the routine returns to block (773) of FIG. 36A.

4. Mode "3" Delivery Routine

Figure 36D:
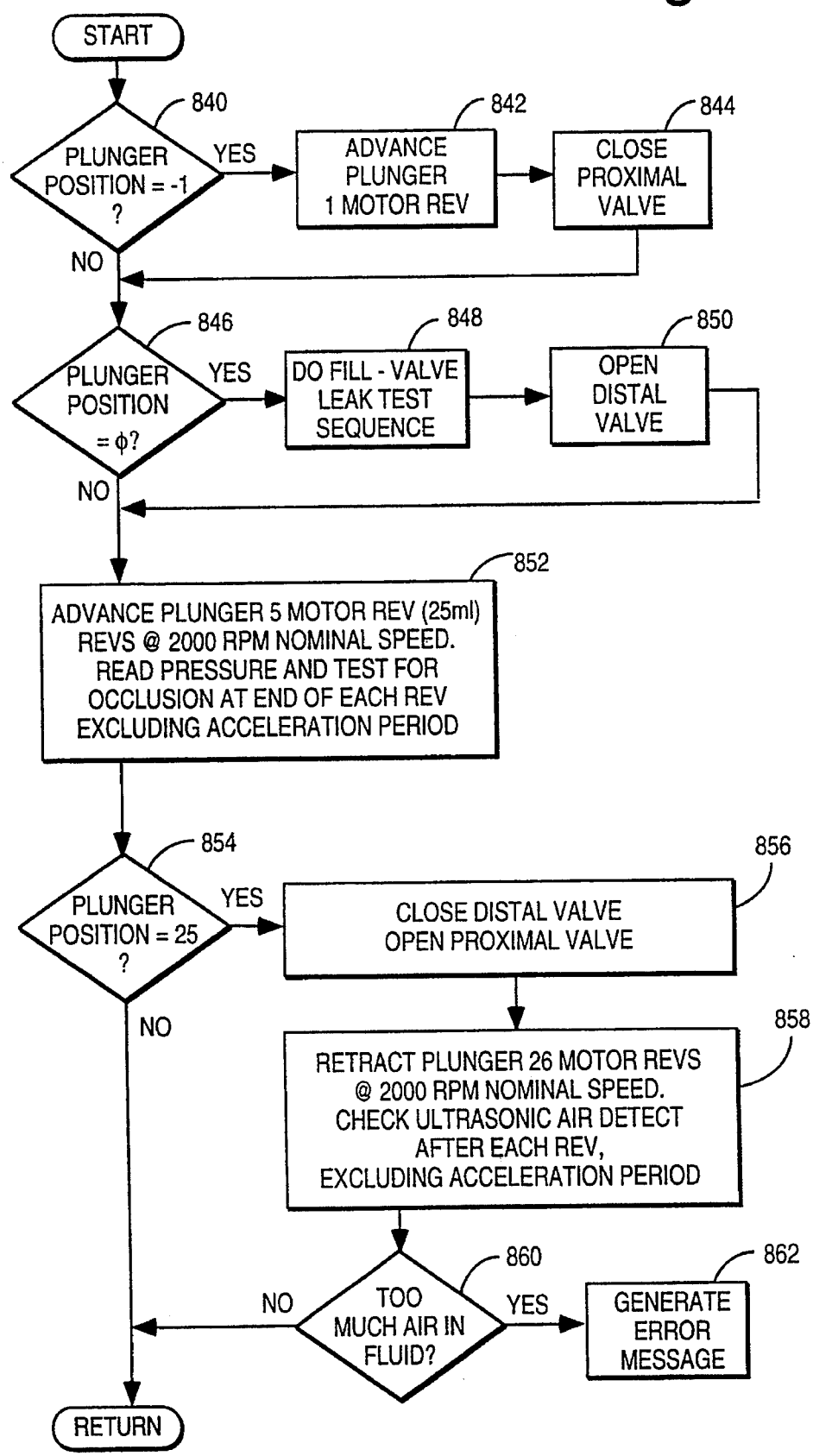
FIG. 36D is a flow diagram of the mode "3" delivery routine.

FIG. 36D illustrates the subroutine for executing delivery mode three. Determination is made at decision block (840) whether the plunger position is equal to "–1". If the plunger position is equal to "–1", the plunger is advanced one motor revolution at block (842). At block (844) the proximal or inlet valve is closed. If the plunger position is not equal to "–1" at block (840), or following closure of the proximal valve at block (844), at decision block (846) it is determined whether the plunger position is equal to "0". If the answer is yes, the fill and valve leak test sequence described in detail with respect to FIG. 36G is performed at block (848). Thereafter, at block (850) the distal or outlet valve is opened. If the plunger position is not equal to "0", or following opening of the distal valve at block (850), at block (852) the plunger motor is advanced five motor revolutions at 2000 rpm nominal speed so as to discharge twenty-five microliters of medication. At the end of each motor revolution, except during the acceleration period, the pump chamber pressure is monitored to check for downstream occlusions. At decision block (854) it is determined whether the plunger (120) is at position number "25". If it is not, the routine returns to block (774) of FIG. 36A. If the plunger position is equal to "25", at block (856) the distal or outlet valve (124) is closed and the proximal or inlet valve (122) is opened. At block (858) the plunger (120) is retracted 26 motor revolutions at a 2000 rpm nominal speed. At the conclusion of each revolution of the plunger motor (256), excluding the acceleration period, ultrasonic air detection takes place. At decision block (860) it is determined whether too much air has entered the pump chamber. If so, an error message is generated at block (862). If the amount of air is acceptable, the routine returns to block (773) of FIG. 36A.

5. Mode "4" Delivery Routine

Figure 36E:
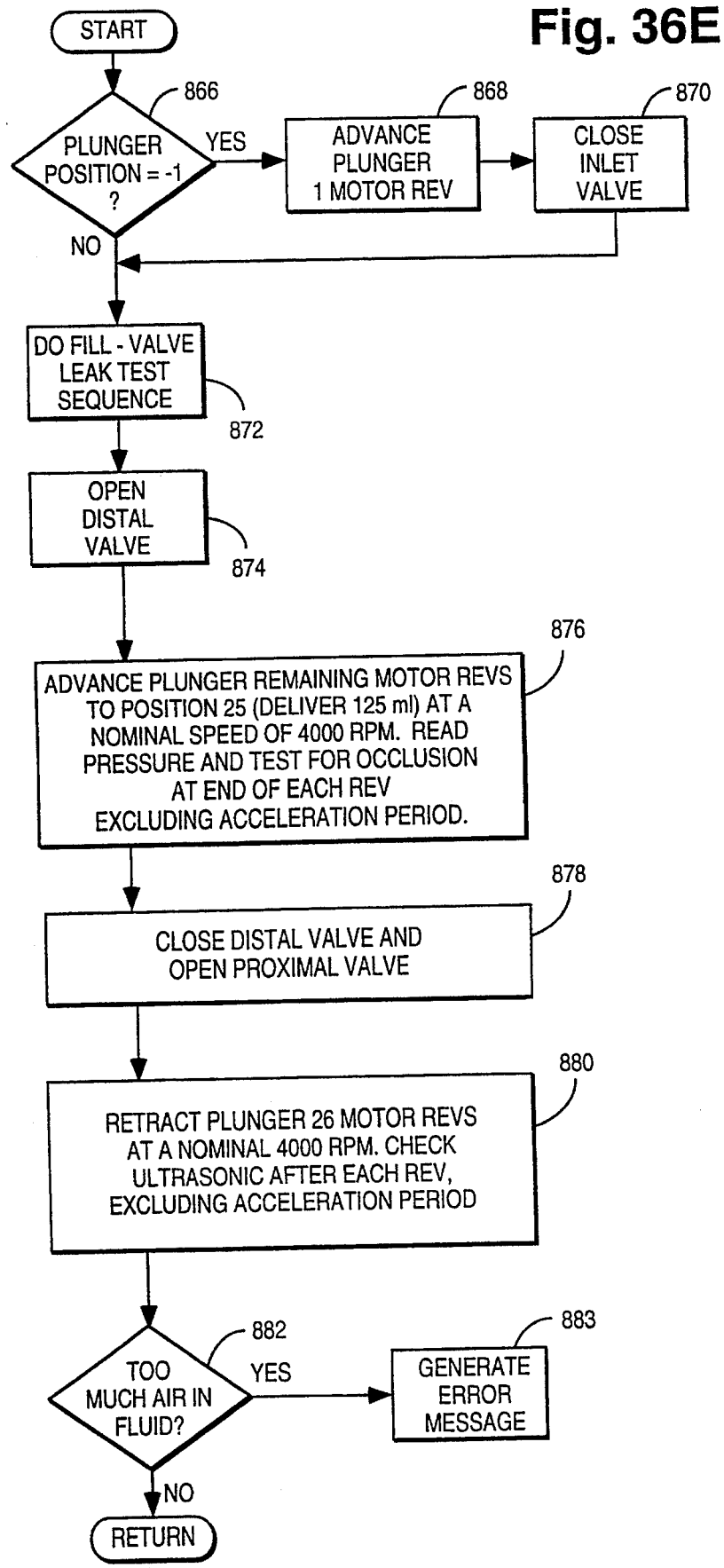
FIG. 36E is a flow diagram of the mode "4" delivery routine.

FIG. 36E illustrates the routine for executing delivery mode four. Determination is made at decision block (866) whether the plunger is at position "–1". If it is, the plunger is advanced one motor revolution at block (868) and the outlet valve (124) is closed at block (870). If the plunger position was not equal to "–1" at decision block (866), or following execution of block (870), at block (872) fill and valve leak test sequence described below with reference to FIG. 36G is conducted. At block (874) the distal valve is opened. At block (876) the plunger is advanced to position "25" at a nominal speed of 4000 rpm, delivering 125 microliters of medication. Pump chamber pressure is read at the end of each revolution, excluding the acceleration period, to test for downstream occlusions. If a downstream occlusion is detected, an alarm signal is generated. At block (878) the outlet valve is closed and the inlet valve (122) is opened. At block (880) the plunger (120) is retracted 26 motor revolutions at a nominal speed of 4000 rpm. At the end of each revolution of the plunger motor (256), excluding the acceleration period, the ultrasonic air detect (130) detects any air in the fluid entering the pump chamber (140). At decision block (882) it is determined whether too much air has entered the pump chamber. If excess air has entered the pump chamber, an error message is generated at block (883).

If the amount of air is acceptable, the routine returns to block (773) of FIG. 36A.

6. Mode "5" Delivery Routine

Figure 36F:
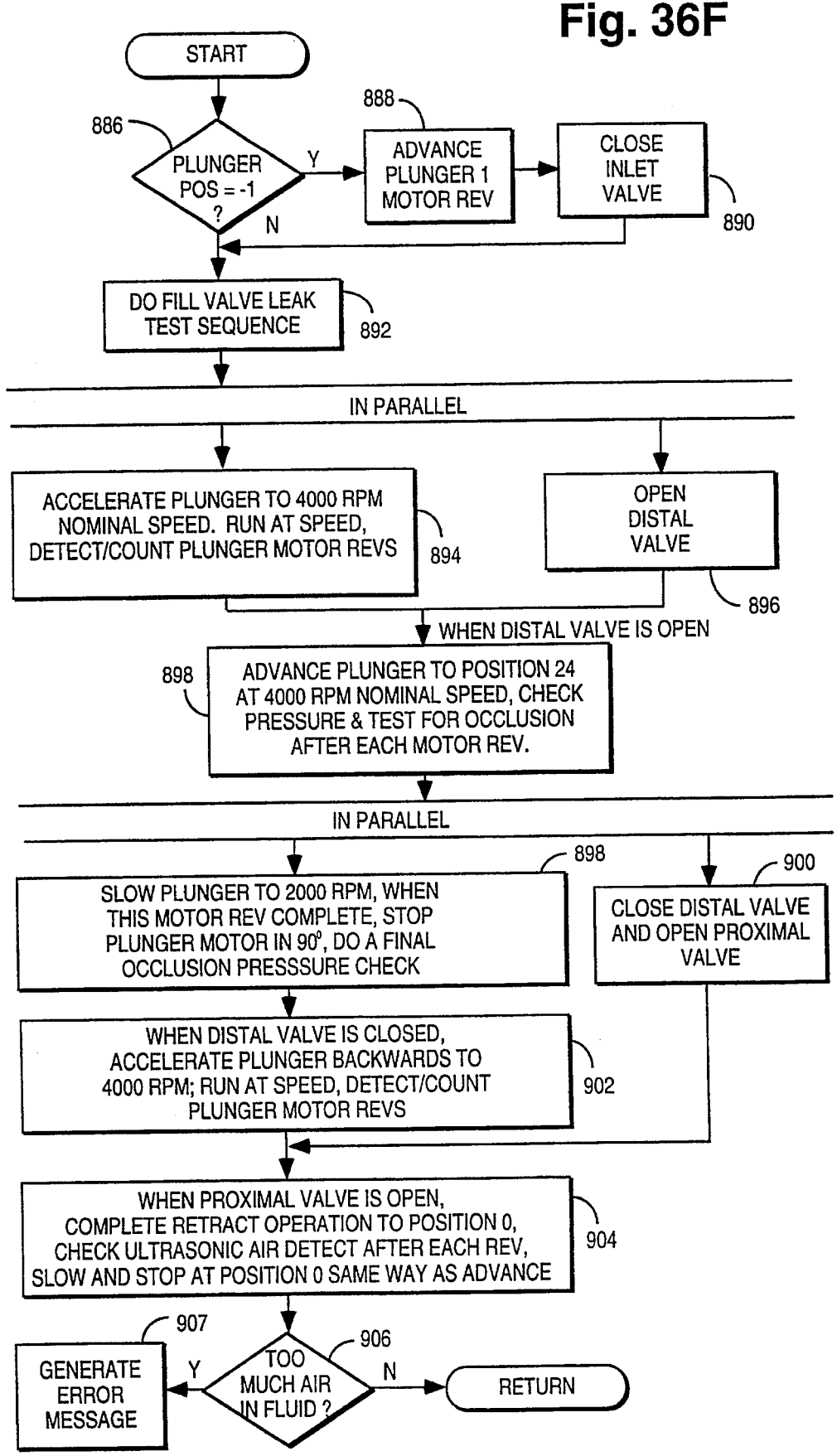
FIG. 36F is a flow diagram of the mode "5" delivery routine.
Figure 36G:
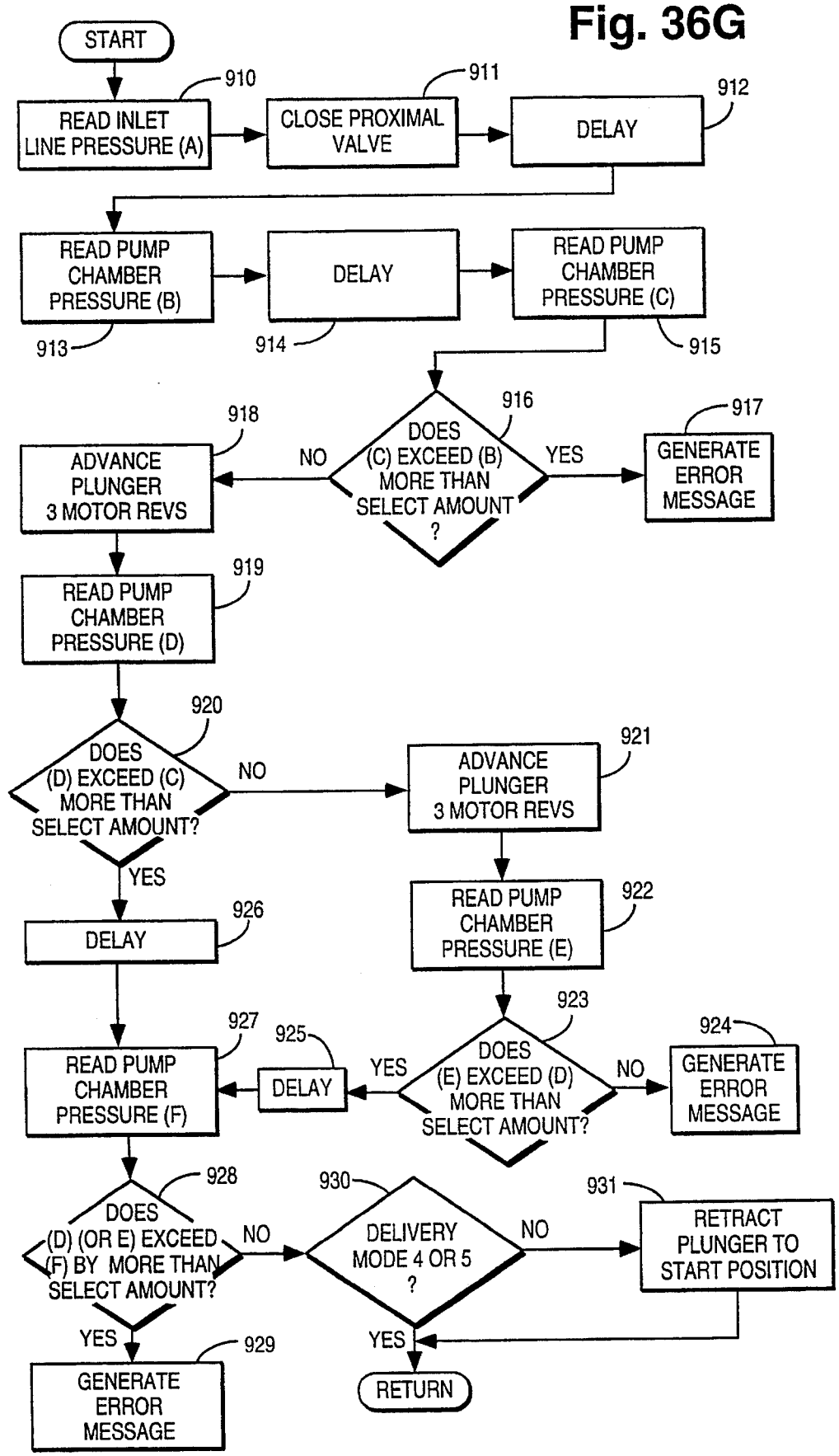
FIG. 36G is a flow diagram of the "fill and valve leak test" sequence of FIG. 36A.

FIG. 36F is a flow diagram illustrating execution of delivery mode 5. It is determined at decision block (866) whether the plunger (120) is in position "–1". If the plunger is in position "–1", the plunger is advanced one motor revolution of plunger motor (256) at block (888). At block (890) the inlet valve (122) is closed. The fill and valve leak test sequence described in detail with reference to FIG. 36G is performed at block (892). Block (894) and block (896) are then performed in parallel. More particularly, at block (894) the plunger motor (256) is accelerated to 4000 rpm nominal speed. The plunger motor revolutions are monitored by means of the Hall sensor (400) on the plunger motor (256). Concurrently, at block (896) the outlet valve (124) is opened so as to discharge fluid from the pump chamber (140). Upon opening of the outlet valve (124) at block (896), at block (898) the plunger motor (256) is advanced to position "24" at 4000 rpm nominal speed. Pressure is checked after each motor revolution for downstream occlusion. Blocks (898) and (900) are then performed in parallel. More particularly, at block (898) the plunger motor is slowed to 2000 rpm for its 25th revolution. When this revolution is complete, the plunger motor is stopped by the magnetic detent following 90 degrees of additional rotation and a final occlusion pressure check is conducted. Concurrently, at block (900) the outlet valve (124) is closed and the inlet valve (122) is opened. Upon closure of the outlet valve (124), at block (902) the plunger motor (256) is accelerated backward to 4000 rpm, with the revolutions being counted by monitoring of the Hall sensor (400). At block (904) the plunger motor (256) operates at 4000 rpm until the plunger (120) is in position "1", at which time the plunger motor is slowed to 2000 rpm and is brought to rest at position "0" in the same way it is advanced at block (898). Ultrasonic air detection occurs after each revolution, excluding acceleration and deceleration. The results of the ultrasonic air detect are evaluated at block (906). If excessive air is detected, an error message is generated at block (907). If the amount of air is acceptable, the routine returns to block (773) of FIG. 36A.

7. Fill and Valve Leak Test Sequence Routine

The "fill and valve leak test sequence" routine described in each delivery mode subroutine of FIGS. 36B–F is illustrated in the flow diagram of FIG. 36G. At block (910) the inlet line pressure designated herein as "A" is read using the pressure transducer (362). The inlet or proximal valve (122) is then closed at block (911). Following a short delay at block (912), the pump chamber pressure is read again at block (913) and is designated herein as "B". At block (914) a delay occurs which is a function of the rate of delivery at the particular mode. That is, the higher the rate of delivery, the shorter the delay at block (914). At block (915) the pump chamber pressure is read again and is designated herein as "C". At block (916) it is determined whether pressure "C" exceeds pressure "B" by more than a select amount. That is, at decision block (96) it is determined whether the inlet pincher valve (122) is leaking, which may be the case where the inlet line pressure "A" exceeds the pump chamber pressures "B". If pressure "C" exceeds pressure "B" by more than the select amount, an error message is generated at block (917). If it does not, at block (918) the plunger (120) is advanced three revolutions of the plunger motor (256). At block (919) the pump chamber pressure is again read and the read pressure is designated herein as "D". At decision block (920) it is determined whether pressure "D" exceeds pressure "C" more than a select amount. If pressure "D" does not exceed pressure "C" more than a select amount, this is an indication that one of the inlet or outlet pincher valves (122,124) is leaking. The test is then repeated at block (921), where the plunger (120) is advanced three more revolutions of the pump motor. At (922) the pump chamber pressure is again read, and designated "E" herein. At decision block (923) it is determined whether pressure "E" exceeds pressure "D" more than a select amount. If it does not, this confirms a leak at one of the inlet and outlet pincher valves (122,124) and an error message is generated at block (924). If "E" does exceed "D" by more than a select amount, at block (925) a delay is instituted. Likewise, if at decision block (920) it is determined that pressure "D" does exceed pressure "C" by more than a select amount, at block (926) a delay is instituted. Following the delays at blocks (925), (926), at (927) the pump chamber is again read and designated herein as "F". At decision block (928) it is determined whether pressure "D" (or, if at decision block (920) "D" does not exceed "C" by more than a select amount, pressure "E") exceeds "F" by more than a select amount. If it does, this again indicates that one of the inlet or outlet pincher valves (122,124) is leaking, and an error message is generated at block (929). If it does not, at block (930) it is determined whether the routine is in delivery mode "4" or "5". If it is not, at block (931) the plunger motor is retracted to the start position. Following retraction of the plunger at block (931), the routine returns to block (792), (816) or (850) of delivery modes 1–3 illustrated in FIGS. 36B–36D, respectively. If at decision block (930) the routine is in delivery mode 4 or 5, the routine returns to block (874) or block (894) of FIGS. 36E and 37F, respectively.

8. Sleep Routine

Figure 36H:
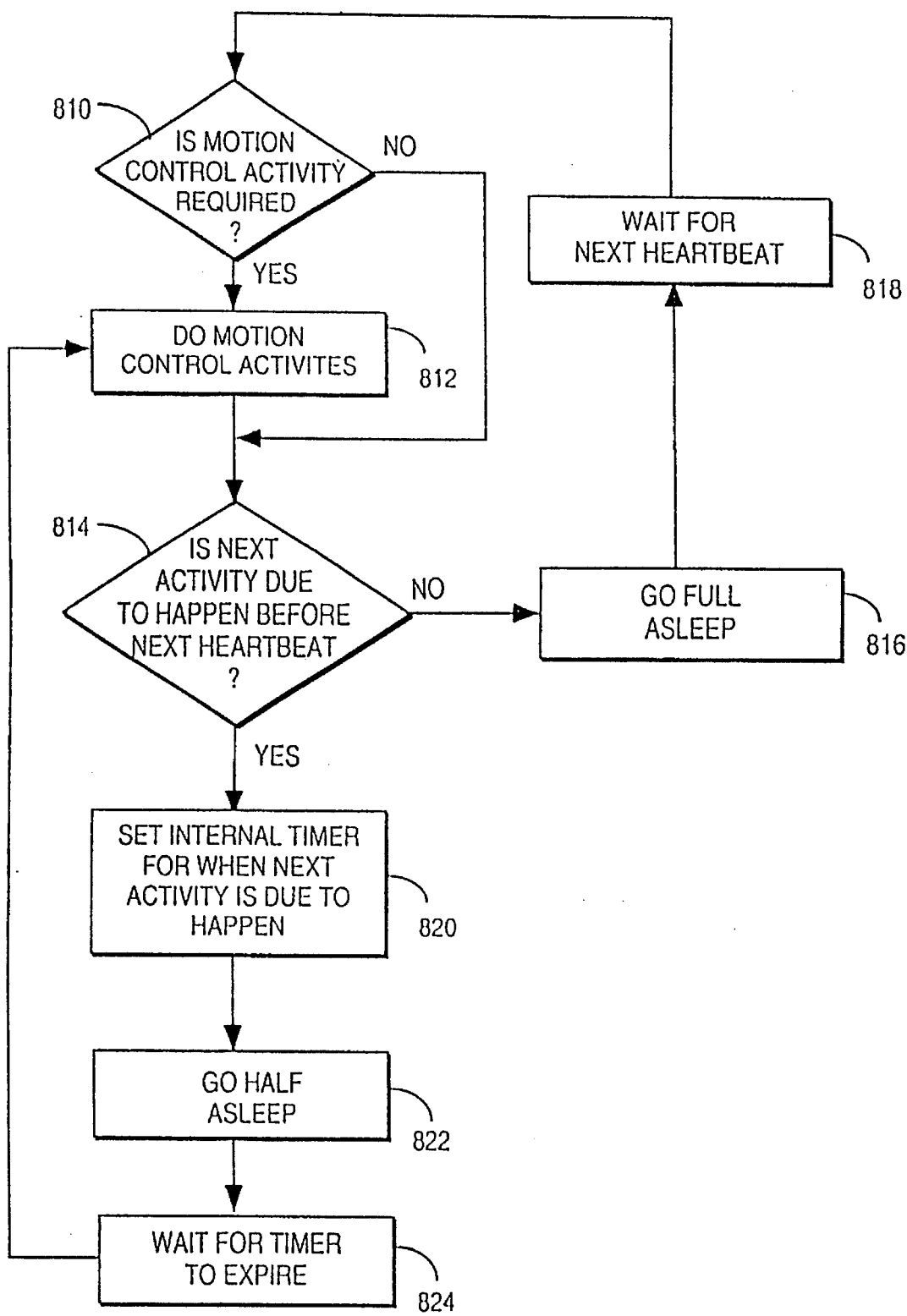
FIG. 36H is a flow diagram of the "sleep" routine.
Figure 36:
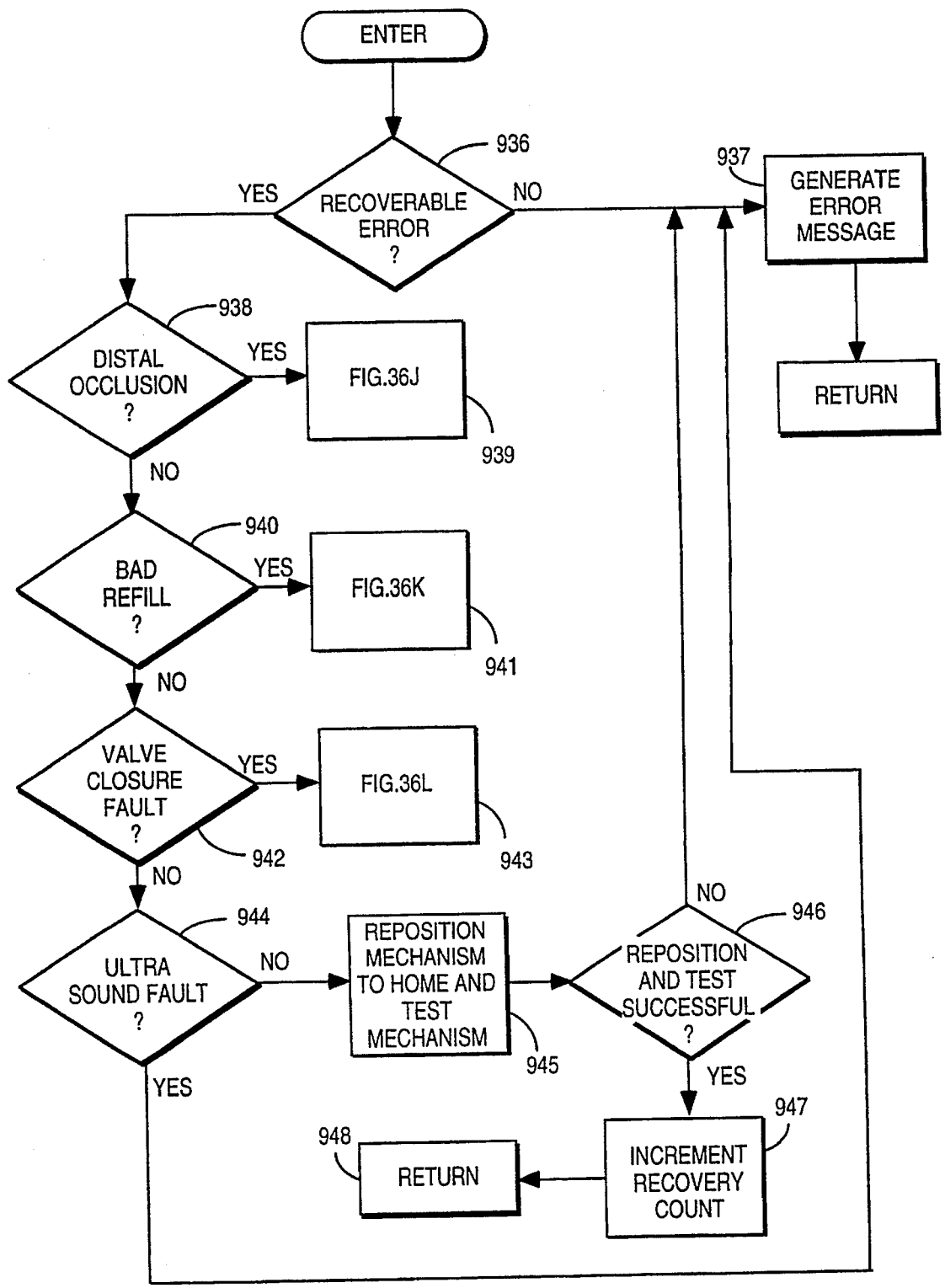
FIG. 36I–L is a flow diagram of the "fault recovery attempt" routine.

Between each of the blocks of the routines illustrated in FIGS. 36B–F is interposed an electronic sleep feature which, in conjunction with a heartbeat generator (590), see FIG. 31, minimizes power consumption by causing the control microprocessor (542) to power down when no control activity is required. The operation of the electronic sleep feature is illustrated in FIG. 36H. At decision block (810) it is determined whether a motion control activity is required. A motion control activity is required when a change in an output related to motion control must be made. If a motion control activity is required, the motion control activity is initiated at block (812). If no motion control activity is required, or after a motion control activity is completed at block (812), at block (814) determination is made whether the next activity is due to be initiated the next heartbeat. If the activity is not due to happen before the next heartbeat, then the control microprocessor (542) is put to sleep. At block (818) the next heartbeat is detected and the routine returns to decision block (810). If it is determined at decision block (814) that the next activity is due to happen before the next heartbeat, an internal timer for when the next activity is due to happen is set at block (820). The control microprocessor (542) then goes into an idle state or a "half asleep sham" at block (822) and at block (824) waits for the timer period to expire. Upon expiration of the timer period, the routine returns to block (812) where the motion control activity is completed.

9. Fault Recovery Routine

The software fault recovery attempts routine, which is called at the block (776) of the main control microprocessor routine illustrated in FIG. 36A, is illustrated in the flow diagram of FIGS. 36I–36L.

Unexpected operating conditions will cause error flags to be set. Within the dual microprocessor software system, detection of fault conditions causes recovery attempts to be made within the constraints of the system. This improves fault tolerance of the pump (10) which in turn improves performance characteristics as it attempts to overcome transient fault conditions such as a patient rolling over on the tubing or a patient pressing against an IV bag.

Referring initially to FIG. 36I, a flow diagram illustrates the fault recovery routine. The routine begins at a decision block (936) which determines whether the error detected at the decision block (773) of the main control microprocessor routine of FIG. 36A is a recoverable error.

Non-recoverable errors include an absence of a plunger home signal, absence of a valve neutral signal, a feedback circuitry error, and an illegal pump command (e.g., a command disrupted during transmission from the monitor microprocessor to the control microprocessor). If such a non-recoverable error is identified at decision block (936), at block (937) an error message is generated and conveyed to the monitor microprocessor (540). At block (944) the routine returns to block (777) of the main control microprocessor subroutine of FIG. 36A.

Figure 36J:
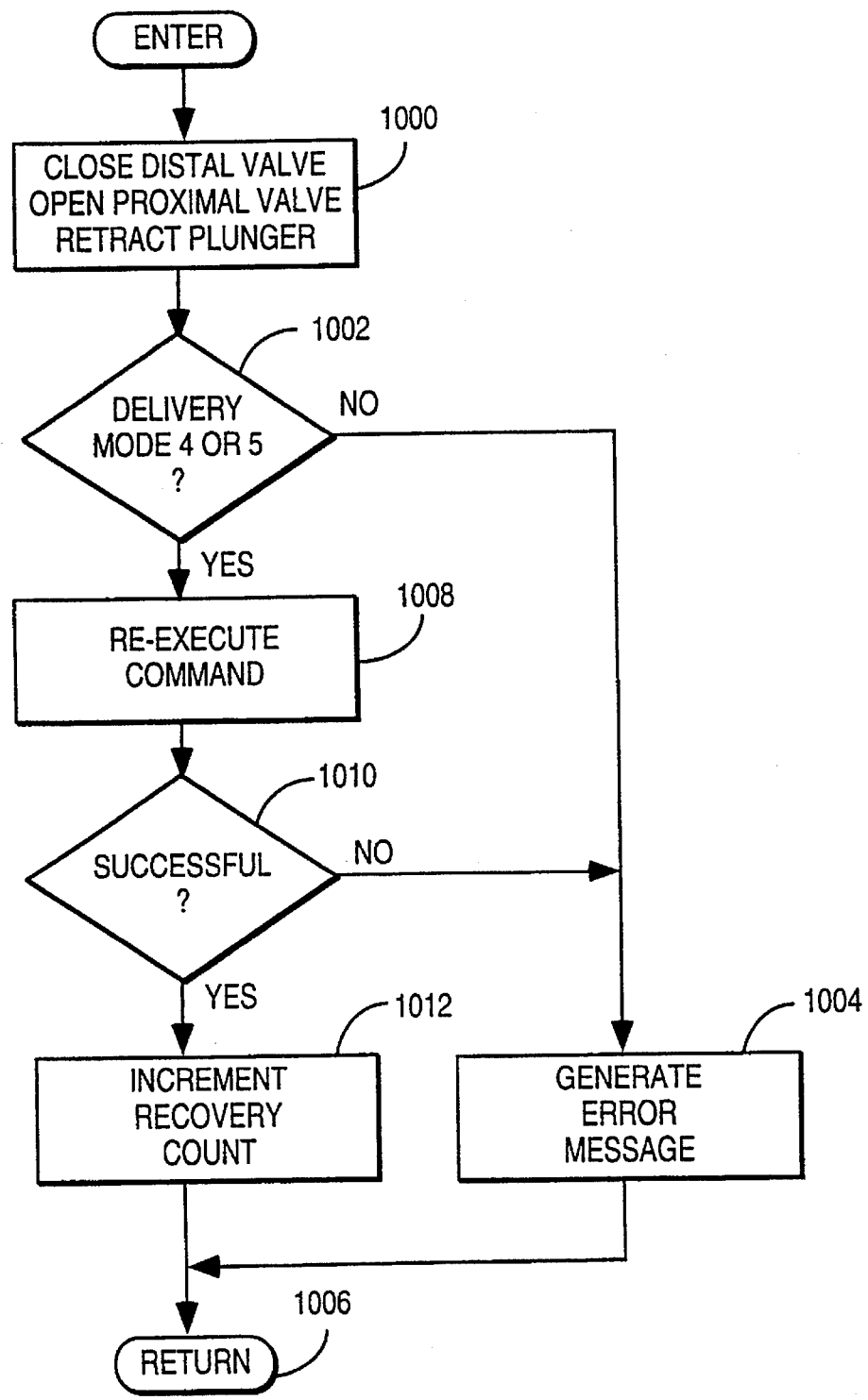
Figure 36K:
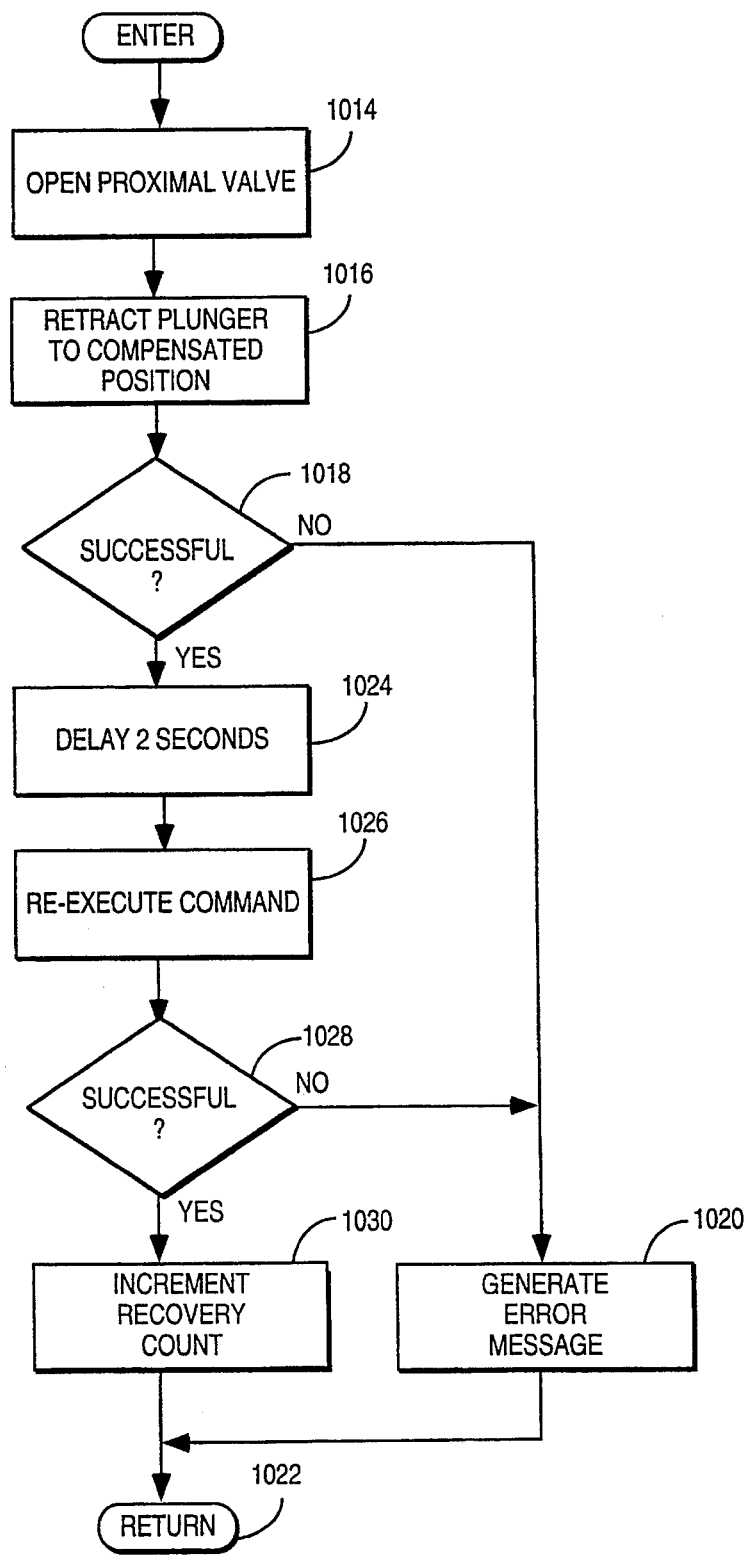

If the error is not identified as a non-recoverable error, the routine continues at decision block (938) where it is determined whether the error message is that a distal occlusion condition is present. If a distal occlusion occurs as determined by an excessive pressure rise, then a recovery routine illustrated in FIG. 36J is implemented. This routine begins at a block (1000) by closing the distal or outlet valve (124), opening the proximal or inlet valve (122) and retracting the plunger (120). A decision block (1002) then determines if either delivery mode 4 or 5 was being executed. If not, then an error message is generated at a block (1004) and the routine ends at a block (1006). If either delivery mode 4 or 5 was being executed, then the original command being acted upon at the time the error occurred is reexecuted at a block (1008). A decision block (1010) determines if the command was reexecuted successfully. If not, then control proceeds to the block (1004). If the command was successful, then a recovery count is incremented at a block (1012) and the routine ends.

The recovery count is used to determine if excessive recovery operations have occurred. If too many recovery operations have occurred, then the delivery action could be impacted negatively, warranting shutting down the pump (10) and generating an alarm.

In the flow diagrams, when the recovery count is incremented it is assumed that recovery is successful. This determination is used at the decision block (777) of FIG. 36A. If, instead, an error message is generated, then it is assumed that recovery was unsuccessful and further operation of the pump driving mechanism is halted.

Returning to FIG. 36I, if the error message is not for a distal occlusion, as determined at the decision block (938), then a decision block (940) determines if the error message is for a bad refill of the pump chamber. This occurs when there is an insufficient indicated pressure rise after advancing the plunger (120) with both valves (122) and (124) closed. If a bad refill error has occurred, then control advances to a block (941) to implement a recovery routine illustrated in FIG. 36K.

The bad refill recovery routine begins at a block (1014) which opens the proximal valve (122). The plunger (120) is retracted at a block (1016) to a compensated position. A decision block (1018) determines if the commands generated at the blocks (1014) and (1016) were executed successfully. If not, then an error message is generated at a block (1020) and the routine ends at a block (1022). If the commands were successful, then a two second delay is implemented at a block (1024) and the original delivery command is reexecuted at a block (1026). A decision block (1028) determines if the original command was reexecuted successfully. If not, then control proceeds to the block (120). If so, then the recovery count is incremented at a block (1030) and the routine ends.

Figure 36L:
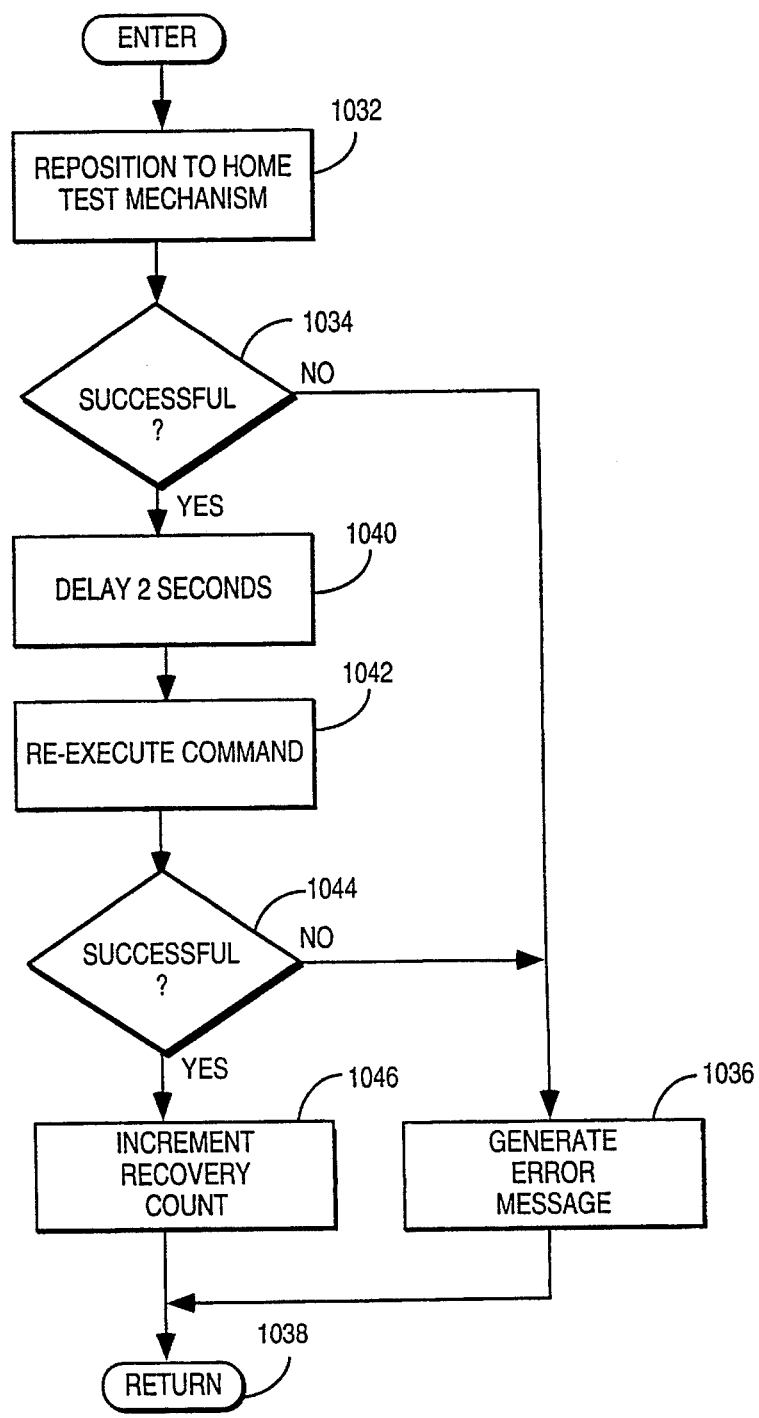

Returning to the flow diagram of FIG. 36I, if the error message was not for a bad refill, as determined at the decision block (940), then a decision block (942) determines if the error was for a valve closure fault. This fault occurs if there is an increase in indicated pressure after closing the proximal valve (122) and delaying for a flow rate dependent period of time. If so, then a recovery routine illustrated in FIG. 36L is implemented at a block (943).

The valve closure fault recovery routine begins at a block (1032) which repositions the mechanism to a "home" position. More particularly, the plunger (120) is returned to its "home" or "zero" position, the distal valve (124) is opened and the proximal valve (122) is closed. Before the mechanism returns to the "home" position, however, each of the inlet valve (122), outlet valve (124) and plunger (120) are tested by actuation to assure they are functioning properly. If they are not, or if the mechanism cannot return to the "home" position, as determined at a decision block (1034), then an error message is generated at a block (1036) and the routine ends at a block (1038). If the repositioning is successful, then a two second delay is implemented at a block (1040). The original command is then reexecuted at a block (142). A decision block (1044) then determines if the original command was reexecuted successfully. If not, then control proceeds to the block (136). If so, then the recovery count is incremented at block (1046) and the routine ends.

Returning to the flow diagram of FIG. 36I, if the error message is not for a valve closure fault, then a decision block (944) determines if the error was for an ultrasound fault. This error occurs if excessive air has been detected by the ultrasonic air detector (130). If so, then an error message is generated at the block (937) and the routine ends. If an ultrasound fault has not occurred, then one of numerous other recoverable errors is assumed. Such errors may include the plunger motor being out of position, or the plunger or valve motor not responding. With such error, control proceeds to a block (945) which repositions the mechanism to the "home" position and tests the mechanism, as done at the block (1032) of FIG. 36L, discussed above. A decision block (946) determines if the repositioning is successful. If not, then control proceeds to the block (937). If so, then the recovery count is incremented at a block (947) and the routine ends.

The fault recovery routine is operable to respond to an error signal indicating error from which the pump driving mechanism can recovery by repositioning the pump driving mechanism to a preselect neutral position prior to continuation of an infusion pumping sequence.

Thus, in accordance with the invention there is illustrated a medical ambulatory infusion pump which accurately and safely administers a wide range of infusion rates.

We claim:

1. An ambulatory infusion pump system for providing a continuous source of liquid medication to an ambulatory patient, the ambulatory infusion pump system comprising:

a liquid medication reservoir;

a conduit for conveying liquid medication from the reservoir to the patient;

an ambulatory infusion pump for pumping liquid medication from the liquid medication reservoir to the patient by manipulation of the conduit; and a case for the ambulatory infusion pump and the liquid medication reservoir, the case comprising:
a first chamber receiving the ambulatory pump;
a second chamber receiving the liquid medication reservoir;
means for maintaining the first chamber juxtaposed to the second chamber;
outlet means through the case for the conduit; and
means on the exterior of one of the first and second chambers for attaching the case to an upright support with the second chamber disposed between the first chamber and the upright support.

2. The ambulatory infusion pump system of claim 1 wherein the attaching means comprises at least one belt loop on an exterior of the second chamber.

3. The ambulatory infusion pump system of claim 1 wherein the first and the second chambers are formed of fabric.

4. The ambulatory infusion pump system of claim 1 wherein the first chamber comprises an open cavity having a bottom wall with four side walls extending transversely therefrom and the second chamber comprises a partition attached about part of its periphery to a backing, the partition dividing the first chamber from the second chamber, the backing being fixedly attached lengthwise to one of the side walls of the first chamber.

5. The ambulatory infusion pump system of claim 4 wherein the maintaining means comprises cooperating zipper teeth about the top of the first chamber side walls and the periphery of the backing, a slider for selectively engaging the teeth to maintain the first and second chambers in the abutting, overlying relationship and disengaging the teeth to allow the first chamber to be opened from the second chamber in a book-like fashion about the fixedly attached portions of the backing and the side wall of the first chamber.

6. The ambulatory infusion pump system of claim 5 wherein the maintaining means further comprises a first zipper segment and a second zipper segment with each zipper segment having a slider associated therewith, there being a stop on each of the first and second zipper segments, the outlet means being a gap defined by the stops between the first and the second zipper segments.

7. The ambulatory infusion pump system of claim 4 wherein the ambulatory pump includes an outer surface having a control panel thereon, the corresponding side wall comprising a clear membrane having a retractable covering attached to the case and means for maintaining the retractable covering over the clear membrane.

8. The ambulatory infusion pump system of claim 1 wherein the liquid medication reservoir comprises a flexible solution bag defining a reservoir having a solution bag outlet connectable to the conduit at one end thereof, the flexible solution bag, when received in the second chamber, having the bag outlet folded over on the reservoir.

\* \* \* \* \*

UNITED STATES PATENT AND TRADEMARK OFFICE
CERTIFICATE OF CORRECTION

PATENT NO. : 5,478,211
DATED : December 26, 1995
INVENTOR(S) : Dominiak, et al.

It is certified that error appears in the above—identified patent and that said Letters Patent is hereby corrected as shown below:

Col. 3, ln. 22, please delete "carder" and insert --carrier--.

Col. 3, ln. 30, please delete "beating" and inset --bearing--.

Col. 5, ln. 22, please delete ",".

Col. 6, ln. 21, please delete "fight" and insert --right--.

Col. 6, ln. 51, please delete "robing" and inset --tubing--.

Col. 7, ln. 16, please delete "tier" and insert --for--.

Col. 8, ln. 26, please delete "robe" and insert --tube--.

Col. 8, ln. 38, please delete "crashed" and insert --crushed--.

Col. 8, ln. 48, please delete "robe" and insert --tube--.

Col. 8, ln. 50, please delete "robe" and insert --tube--.

Col. 9, ln. 10, please delete "vane" and insert --valve--.

Col. 9, ln. 52, please delete "mils" and insert --rails--.

Col. 10, ln. 58, after "cassette", please delete ".".

Col. 11, ln. 4, please delete "fight" and insert --right--.

Col. 11, ln. 26, after "(228) of", please insert --the latch--.

Col. 11, ln. 26, please delete "(see FIG. 14)".

Col. 11, ln. 27, after "(56)", please insert --(see FIG. 14)--.

UNITED STATES PATENT AND TRADEMARK OFFICE
CERTIFICATE OF CORRECTION

PATENT NO. : 5,478,211
DATED : December 26, 1995
INVENTOR(S) : Dominiak, et al.

It is certified that error appears in the above-identified patent and that said Letters Patent is hereby corrected as shown below:

Col. 11, ln. 31, please delete "8" and insert --14--.

Col. 11, ln. 33, after "(220)", please insert ".".

Col. 11, ln. 33, please delete "referring" and insert -- . Referring --.

Col. 11, ln. 46, please delete "fight" and insert --right--.

Col. 12, ln. 23, please delete "fight" and insert --right--.

Col. 13, ln. 15, please delete "beating" and insert --bearing--.

Col. 13, ln. 45, please delete "carder" and insert --carrier--.

Col. 13, ln. 46, please delete "arid" and isnert --and--.

Col. 14, ln. 2, please delete "beating" and insert --bearing--.

Col. 14, ln. 5, please delete "carder" and isnert --carrier--.

Col. 15, ln. 65, please delete "beating" and isnert --bearing--.

Col. 16, ln. 9, please delete "stock" and insert --stuck--.

Col. 17, ln. 54, please delete ",".

Col. 18, ln. 7, please delete "ting" and insert --ring--.

Col. 19, ln. 16, please delete "robe" and insert --tube--.

Col. 19, ln. 18, please delete "robe" and insert --tube--.

Col. 19, ln. 32, please delete "robe" and insert --tube--.

UNITED STATES PATENT AND TRADEMARK OFFICE
CERTIFICATE OF CORRECTION

PATENT NO. : 5,478,211
DATED : December 26, 1995
INVENTOR(S) : Dominiak, et al.

It is certified that error appears in the above—identified patent and that said Letters Patent is hereby corrected as shown below:

Col. 19, ln. 42, please delete "22 . 24" and insert --22-24--.

Col. 21, ln. 28, please delete "ram" and insert --rate--.

Col. 21, ln. 33, please delete "arid" and insert --and--.

Col. 22, ln. 49, after "Pumping", please insert --Action--.

Col. 27, ln. 31, please delete "090)" and insert --(990)--.

Col. 28, ln. 10, please delete "(950) ." and insert --(950).--.

Col. 28, ln. 30, please delete "," before "above".

Col. 30, ln. 27, please delete "m" and insert --to--.

Col. 31, ln. 61, please delete "them" and insert --there--.

Col. 37, ln. 9, please delete "dosed" and insert --closed--.

Col. 37, ln. 57, please delete "(96)" and insert --(916)--.

Col. 38, ln. 53, please delete "sham" and insert --state--.

UNITED STATES PATENT AND TRADEMARK OFFICE
CERTIFICATE OF CORRECTION

PATENT NO. : 5,478,211
DATED : December 26, 1995
INVENTOR(S) : Dominiak, et al.

It is certified that error appears in the above-indentified patent and that said Letters Patent is hereby corrected as shown below:

Col. 38, ln. 53, please delete "sham" and insert --state--.

Signed and Sealed this

Twenty-first Day of May, 1996

Attest:

BRUCE LEHMAN

Attesting Officer

Commissioner of Patents and Trademarks